United States Patent
Fernandez Forner et al.

(10) Patent No.: US 10,588,895 B2
(45) Date of Patent: *Mar. 17, 2020

(54) QUINUCLIDINE DERIVATIVES AND MEDICINAL COMPOSITIONS CONTAINING THE SAME

(71) Applicant: ALMIRALL, S.A., Barcelona (ES)

(72) Inventors: Maria Dolors Fernandez Forner, Barcelona (ES); Maria Prat Quinones, Barcelona (ES); Maria Antonia Buil Albero, Barcelona (ES)

(73) Assignee: ALMIRALL, S.A., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 16/045,333

(22) Filed: Jul. 25, 2018

(65) Prior Publication Data

US 2019/0183867 A1    Jun. 20, 2019

Related U.S. Application Data

(60) Continuation of application No. 15/599,646, filed on May 19, 2017, now Pat. No. 10,034,867, which is a continuation of application No. 15/095,036, filed on Apr. 9, 2016, now Pat. No. 9,687,478, which is a continuation of application No. 14/712,866, filed on May 14, 2015, now Pat. No. 9,333,195, which is a continuation of application No. 14/311,102, filed on Jun. 20, 2014, now Pat. No. 9,056,100, which is a continuation of application No. 13/939,742, filed on Jul. 11, 2013, now Pat. No. 8,802,699, which is a continuation of application No. 13/354,873, filed on Jan. 20, 2012, now Pat. No. 8,513,279, which is a continuation of application No. 13/011,131, filed on Jan. 21, 2011, now Pat. No. 8,129,405, which is a continuation of application No. 12/787,772, filed on May 26, 2010, now Pat. No. 7,897,617, which is a continuation of application No. 12/074,929, filed on Mar. 7, 2008, now Pat. No. 7,750,023, which is a continuation of application No. 11/636,181, filed on Dec. 8, 2006, now Pat. No. 7,358,260, which is a continuation of application No. 11/325,059, filed on Jan. 3, 2006, now Pat. No. 7,196,098, which is a division of application No. 11/116,777, filed on Apr. 28, 2005, now Pat. No. 7,078,412, which is a continuation of application No. 10/740,264, filed on Dec. 17, 2003, now Pat. No. 7,109,210, which is a division of application No. 10/047,464, filed on Jan. 14, 2002, now Pat. No. 6,750,226, which is a continuation of application No. PCT/EP00/06469, filed on Jul. 7, 2000.

(30) Foreign Application Priority Data

Jul. 14, 1999    (ES) .................... 9901580

(51) Int. Cl.

| | |
|---|---|
| A61K 31/439 | (2006.01) |
| A61K 31/4745 | (2006.01) |
| A61K 31/56 | (2006.01) |
| A61K 45/06 | (2006.01) |
| C07D 453/02 | (2006.01) |
| A61K 9/00 | (2006.01) |
| A61K 47/26 | (2006.01) |

(52) U.S. Cl.
CPC .......... *A61K 31/439* (2013.01); *A61K 9/0073* (2013.01); *A61K 9/0075* (2013.01); *A61K 31/4745* (2013.01); *A61K 31/56* (2013.01); *A61K 45/06* (2013.01); *A61K 47/26* (2013.01); *C07D 453/02* (2013.01); *Y10S 514/826* (2013.01)

(58) Field of Classification Search
CPC .................................................... A61K 31/439
USPC ........................................................ 514/305
See application file for complete search history.

(56) References Cited

U.S. PATENT DOCUMENTS

| | | |
|---|---|---|
| 3,091,570 A | 5/1963 | Biel |
| 3,714,357 A | 1/1973 | Gueremy |
| 4,224,332 A | 9/1980 | Gueremy |
| 4,338,931 A | 7/1982 | Cavazza |
| 4,579,854 A | 4/1986 | Iwakuma et al. |
| 4,644,033 A | 2/1987 | Gnanou et al. |
| 4,675,326 A | 6/1987 | Amitai |
| 4,843,074 A | 6/1989 | Rzeszotarski |
| 4,855,290 A | 8/1989 | Fisher et al. |

(Continued)

FOREIGN PATENT DOCUMENTS

| | | |
|---|---|---|
| AU | 2002257587 | 9/2002 |
| AU | 2005202144 B2 | 6/2005 |

(Continued)

OTHER PUBLICATIONS

U.S. Appl. No. 10/047,464, filed Jan. 2002, Fernandez Forner et al.

(Continued)

*Primary Examiner* — Charanjit Aulakh
(74) *Attorney, Agent, or Firm* — Hoxie & Associates LLC

(57) ABSTRACT

Provided is a method for treating chronic obstructive pulmonary disease or chronic bronchitis, or inhibiting bronchospasm, which method comprises use of a powder inhaler to administer to a human patient in need of such treatment an effective amount of a powder inhalant, wherein the powder inhalant comprises 3(R)-(2-hydroxy-2,2-dithien-2-ylacetoxy)-1-(3-phenoxypropyl)-1-azoniabicyclo[2.2.2]octane bromide.

13 Claims, No Drawings

(56) References Cited

U.S. PATENT DOCUMENTS

| | | |
|---|---|---|
| 5,201,308 A | 4/1993 | Newhouse et al. |
| 5,254,330 A | 10/1993 | Ganderton et al. |
| 5,263,475 A | 11/1993 | Altermatt et al. |
| 5,290,539 A | 3/1994 | Marecki |
| 5,290,815 A | 3/1994 | Johnson et al. |
| 5,435,301 A | 7/1995 | Herold et al. |
| 5,507,281 A | 4/1996 | Kuhnel et al. |
| 5,569,447 A | 10/1996 | Lee et al. |
| 5,575,280 A | 11/1996 | Gupte et al. |
| 5,610,163 A | 3/1997 | Banholzer et al. |
| 5,617,845 A | 4/1997 | Poss et al. |
| 5,654,314 A | 8/1997 | Banholzer |
| 5,676,930 A | 10/1997 | Jager et al. |
| 5,685,294 A | 11/1997 | Gupte et al. |
| 5,885,834 A | 3/1999 | Epstein |
| 5,962,505 A | 10/1999 | Bobrove et al. |
| 5,964,416 A | 10/1999 | Jaeger et al. |
| 6,150,415 A | 11/2000 | Hammock et al. |
| 6,299,861 B1 | 10/2001 | Banholzer et al. |
| 6,299,863 B1 | 10/2001 | Aberg et al. |
| 6,402,055 B1 | 6/2002 | Jaeger et al. |
| 6,410,563 B1 | 6/2002 | Deschenes et al. |
| 6,423,298 B2 | 7/2002 | McNamara et al. |
| 6,433,027 B1 | 8/2002 | Bozung et al. |
| 6,455,524 B1 | 9/2002 | Bozung |
| 6,475,467 B1 | 11/2002 | Keller |
| 6,481,435 B2 | 11/2002 | Hochrainer et al. |
| 6,497,373 B2 | 12/2002 | Jaeger et al. |
| 6,521,260 B1 | 2/2003 | Staniforth |
| 6,521,261 B2 | 2/2003 | Sherwood et al. |
| 6,537,524 B1 | 3/2003 | Hassan |
| 6,608,054 B2 | 8/2003 | Meade et al. |
| 6,620,438 B2 | 9/2003 | Pairet et al. |
| 6,680,345 B2 | 1/2004 | Linz et al. |
| 6,686,346 B2 | 2/2004 | Nilsson |
| 6,696,042 B2 | 2/2004 | Pairet et al. |
| 6,706,726 B2 | 3/2004 | Meissner et al. |
| 6,726,124 B2 | 4/2004 | Jaeger et al. |
| 6,749,015 B2 | 6/2004 | Moreau |
| 6,750,226 B2 * | 6/2004 | Forner ............ A61K 31/4745 514/305 |
| 6,756,508 B2 | 6/2004 | Linz et al. |
| 6,814,953 B2 | 11/2004 | Banerjee et al. |
| 6,887,459 B1 | 5/2005 | Haeberlin |
| 6,890,517 B2 | 5/2005 | Drechsel et al. |
| 6,918,547 B2 | 7/2005 | Jaeger et al. |
| 6,919,325 B2 | 7/2005 | Linz et al. |
| 6,924,292 B2 | 8/2005 | Kawano et al. |
| 6,986,346 B2 | 1/2006 | Hochrainer et al. |
| 7,040,311 B2 | 5/2006 | Hochrainer et al. |
| 7,078,412 B2 * | 7/2006 | Fernandez Forner ............ A61K 31/4745 514/305 |
| 7,104,470 B2 | 9/2006 | Jaeger et al. |
| 7,109,210 B2 | 9/2006 | Fernandez Forner et al. |
| 7,122,558 B2 | 10/2006 | Prat Quinones et al. |
| 7,141,671 B2 | 11/2006 | Mammen et al. |
| 7,192,978 B2 | 3/2007 | Quinones et al. |
| 7,196,098 B2 * | 3/2007 | Fernandez Forner ............ A61K 31/4745 514/305 |
| 7,214,687 B2 * | 5/2007 | Fernandez Forner ............ A61K 31/4745 514/305 |
| RE39,820 E | 9/2007 | Banholzer et al. |
| 7,358,260 B2 | 4/2008 | Fernandez Forner et al. |
| 7,569,581 B2 | 8/2009 | Meissner et al. |
| 7,750,023 B2 * | 7/2010 | Fernandez Forner ............ A61K 31/4745 514/305 |
| 7,776,315 B2 | 8/2010 | Pairet et al. |
| 7,897,617 B2 * | 3/2011 | Fernandez Forner ............ A61K 31/4745 514/305 |
| 8,129,405 B2 * | 3/2012 | Fernandez Forner ............ A61K 31/4745 514/305 |
| 8,513,279 B2 * | 8/2013 | Fernandez Forner ............ A61K 31/4745 514/305 |
| 8,802,699 B2 * | 8/2014 | Fernandez Forner ............ A61K 31/4745 514/305 |
| 9,056,100 B2 * | 6/2015 | Fernandez Forner ............ A61K 31/4745 |
| 9,254,262 B2 | 2/2016 | Casado et al. |
| 9,333,195 B2 * | 5/2016 | Fernandez Forner ............ A61K 31/4745 |
| RE46,417 E | 5/2017 | Fernandez Forner et al. |
| 9,687,478 B2 * | 6/2017 | Fernandez Forner ............ A61K 31/4745 |
| 9,737,520 B2 | 8/2017 | Garcia Gil et al. |
| 10,034,867 B2 * | 7/2018 | Fernandez Forner ............ A61K 31/4745 |
| 10,085,974 B2 | 10/2018 | Casado et al. |
| 2002/0025299 A1 | 2/2002 | Lewis et al. |
| 2002/0052312 A1 | 5/2002 | Reiss et al. |
| 2002/0115680 A1 | 8/2002 | Meissner et al. |
| 2002/0119991 A1 | 8/2002 | Meissner et al. |
| 2002/0122773 A1 | 9/2002 | Pairet et al. |
| 2002/0134538 A1 | 9/2002 | Moreau |
| 2002/0137764 A1 | 9/2002 | Drechsel et al. |
| 2002/0151541 A1 | 10/2002 | Pairet et al. |
| 2002/0151597 A1 | 10/2002 | Banerjee et al. |
| 2002/0179087 A1 | 12/2002 | Bozung et al. |
| 2002/0183292 A1 | 12/2002 | Pairet et al. |
| 2002/0189610 A1 | 12/2002 | Bozung et al. |
| 2002/0193392 A1 | 12/2002 | Schmelzer et al. |
| 2002/0193393 A1 | 12/2002 | Pairet et al. |
| 2003/0018019 A1 | 1/2003 | Meade et al. |
| 2003/0018061 A1 | 1/2003 | Ogawa et al. |
| 2003/0085480 A1 | 5/2003 | Yang |
| 2003/0096834 A1 | 5/2003 | Jenkins et al. |
| 2003/0130300 A1 | 7/2003 | Linz et al. |
| 2003/0139369 A1 | 7/2003 | Yeadon |
| 2003/0158196 A1 | 8/2003 | Jung et al. |
| 2003/0199539 A1 | 10/2003 | Germeyer et al. |
| 2003/0199545 A1 | 10/2003 | Grauert et al. |
| 2003/0203925 A1 | 10/2003 | Meade et al. |
| 2003/0216329 A1 | 11/2003 | Robinson et al. |
| 2004/0002548 A1 | 1/2004 | Bozung et al. |
| 2004/0024007 A1 | 2/2004 | Pairet et al. |
| 2004/0058950 A1 | 3/2004 | Meade et al. |
| 2004/0087617 A1 | 5/2004 | Meissner et al. |
| 2004/0151770 A1 | 8/2004 | Pairet et al. |
| 2004/0161386 A1 | 8/2004 | Pairet et al. |
| 2004/0167167 A1 | 8/2004 | Mammen et al. |
| 2004/0176338 A1 | 9/2004 | Pairet |
| 2004/0184995 A1 | 9/2004 | Katsuma et al. |
| 2004/0192675 A1 | 9/2004 | Pairet et al. |
| 2004/0266869 A1 | 12/2004 | Montague et al. |
| 2005/0025718 A1 | 2/2005 | Meade et al. |
| 2005/0026886 A1 | 2/2005 | Meade et al. |
| 2005/0026887 A1 | 2/2005 | Meade et al. |
| 2005/0026948 A1 | 2/2005 | Meade et al. |
| 2005/0147564 A1 | 7/2005 | Drechsel et al. |
| 2005/0175547 A1 | 8/2005 | Maus et al. |
| 2005/0175548 A1 | 8/2005 | Goede et al. |
| 2005/0175549 A1 | 8/2005 | Goede et al. |
| 2005/0209272 A1 | 9/2005 | Fernandez Forner |
| 2005/0244339 A1 | 11/2005 | Jauernig et al. |
| 2005/0256149 A1 | 11/2005 | Linz et al. |
| 2005/0267078 A1 | 12/2005 | Gras Escardo et al. |
| 2005/0267135 A1 | 12/2005 | Escardo et al. |
| 2005/0282875 A1 | 12/2005 | Prat Quinones et al. |
| 2005/0288266 A1 | 12/2005 | Gras Escardo et al. |
| 2006/0030579 A1 | 2/2006 | Park et al. |
| 2006/0057074 A1 | 3/2006 | Meade et al. |
| 2006/0079540 A1 | 4/2006 | Schmidt |
| 2006/0106055 A1 | 5/2006 | Fernandez Forner et al. |
| 2006/0106056 A1 | 5/2006 | Fernandez Forner et al. |
| 2006/0154934 A1 | 7/2006 | Escardo et al. |

(56) References Cited

U.S. PATENT DOCUMENTS

| | | |
|---|---|---|
| 2006/0189651 A1 | 8/2006 | Gras Escardo et al. |
| 2006/0196500 A1 | 9/2006 | Hochrainer et al. |
| 2006/0205702 A1 | 9/2006 | Escardo et al. |
| 2006/0252790 A1 | 11/2006 | Allen et al. |
| 2006/0285987 A1 | 12/2006 | Jaeger et al. |
| 2007/0128125 A1 | 6/2007 | Schmelzer et al. |
| 2008/0214600 A1 | 9/2008 | Fernandez Forner et al. |
| 2009/0088408 A1 | 4/2009 | Meade et al. |
| 2009/0299042 A1 | 12/2009 | Busquets Baque et al. |
| 2010/0234333 A1 | 9/2010 | Fernandez Forner et al. |
| 2010/0310477 A1 | 12/2010 | Pairet et al. |
| 2010/0330186 A1 | 12/2010 | Meade et al. |
| 2011/0020412 A1 | 1/2011 | Lamarca Casado et al. |
| 2011/0020454 A1 | 1/2011 | Lamarca Casado |
| 2011/0021477 A1 | 1/2011 | Gras Escardo et al. |
| 2011/0021478 A1 | 1/2011 | Gras Escardo et al. |
| 2011/0038806 A1 | 2/2011 | Meade et al. |
| 2011/0118223 A1 | 5/2011 | Forner et al. |
| 2011/0243924 A1 | 10/2011 | Beleta Supervia |
| 2012/0040943 A1 | 2/2012 | Gras Escardo et al. |
| 2012/0302532 A1 | 11/2012 | Gras Escardo et al. |
| 2012/0309727 A1 | 12/2012 | Gras Escardo et al. |
| 2013/0035319 A1 | 2/2013 | Gras Escardo et al. |
| 2013/0125884 A1 | 5/2013 | Lamarca Casado et al. |
| 2013/0189317 A1 | 7/2013 | Casado et al. |
| 2013/0196961 A1 | 8/2013 | Gras Escardo et al. |
| 2013/0252928 A1 | 9/2013 | Gras Escardo et al. |
| 2013/0310354 A1 | 11/2013 | Gras Escardo et al. |
| 2014/0094442 A1 | 4/2014 | Gras Escardo et al. |
| 2014/0100246 A1 | 4/2014 | Garcia Gil et al. |
| 2014/0296197 A1 | 10/2014 | Gras Escardo et al. |
| 2015/0080359 A1 | 3/2015 | Gras Escardo et al. |
| 2015/0093374 A1 | 4/2015 | Beleta Supervia |
| 2015/0118312 A1 | 4/2015 | Lamaraca Casado et al. |
| 2015/0246026 A1 | 9/2015 | Fernandez Forner et al. |
| 2015/0328194 A1 | 11/2015 | Jarreta Fernandez et al. |
| 2016/0263091 A1 | 9/2016 | Garcia Gil et al. |
| 2016/0296503 A1 | 10/2016 | Fernandez Forner et al. |
| 2016/0331733 A1 | 11/2016 | Jarreta Fernandez et al. |
| 2017/0049756 A1 | 2/2017 | Gras Escardo et al. |
| 2017/0128426 A1 | 5/2017 | Lamaraca Casado et al. |
| 2017/0319557 A1 | 11/2017 | Fernandez Forner et al. |
| 2018/0000798 A1 | 1/2018 | Jarreta Fernandez et al. |
| 2018/0200234 A1 | 7/2018 | Gras Escardo et al. |
| 2018/0303806 A1 | 10/2018 | Casado et al. |

FOREIGN PATENT DOCUMENTS

| | | |
|---|---|---|
| AU | 2003236784 | 1/2008 |
| AU | 2003216921 | 3/2008 |
| CA | 2062854 | 9/1992 |
| CA | 2429012 | 5/2002 |
| CA | 2436540 | 5/2002 |
| CA | 2455167 | 1/2003 |
| CA | 2459493 | 3/2003 |
| CA | 2516467 | 9/2004 |
| DE | 10216333 | 10/2003 |
| EP | 0003445 | 9/1979 |
| EP | 0069715 | 1/1983 |
| EP | 0166294 | 1/1986 |
| EP | 0302699 | 2/1989 |
| EP | 0418716 A1 | 3/1991 |
| EP | 0424021 A1 | 4/1991 |
| EP | 0424790 A2 | 5/1991 |
| EP | 0505321 | 9/1992 |
| EP | 0205247 | 12/1992 |
| EP | 0424790 B1 | 8/1993 |
| EP | 0424021 B1 | 3/1994 |
| EP | 0418716 B1 | 4/1994 |
| EP | 0747355 | 12/1996 |
| EP | 0801067 A1 | 10/1997 |
| EP | 0603229 | 6/1998 |
| EP | 0801067 B1 | 3/2003 |
| EP | 1087750 | 11/2003 |
| EP | 1452179 | 9/2004 |
| EP | 1471919 | 8/2005 |
| EP | 1651270 | 3/2007 |
| EP | 1763369 | 12/2008 |
| EP | 1763368 B1 | 3/2009 |
| EP | 2100599 | 9/2009 |
| EP | 1763368 B2 | 8/2013 |
| ES | 2165768 | 3/2002 |
| ES | 2206021 | 5/2004 |
| ES | 2239546 | 9/2005 |
| FR | 2012964 | 3/1970 |
| GB | 1219606 | 1/1971 |
| GB | 2041763 | 9/1980 |
| GB | 2165159 | 4/1986 |
| GB | 2242134 | 9/1991 |
| GB | 2419819 | 5/2006 |
| HU | 178679 | 6/1982 |
| MX | PA03008045 | 12/2003 |
| WO | WO 1987/007502 | 12/1987 |
| WO | WO 1991/002558 | 3/1991 |
| WO | WO 1991/004252 | 4/1991 |
| WO | WO 1991/014468 | 10/1991 |
| WO | WO 1992/000771 | 1/1992 |
| WO | WO 1992/003175 | 3/1992 |
| WO | WO 1992/004068 | 3/1992 |
| WO | WO 1992/004345 | 3/1992 |
| WO | WO 1992/004346 | 3/1992 |
| WO | WO 1992/004928 | 4/1992 |
| WO | WO 1992/009322 | 6/1992 |
| WO | WO 1994/014492 | 7/1994 |
| WO | WO 1995/024889 | 9/1995 |
| WO | WO 1996/04346 | 2/1996 |
| WO | WO 1996/019968 | 7/1996 |
| WO | WO 1996/032150 | 10/1996 |
| WO | WO 1997/000703 | 1/1997 |
| WO | WO 1997/001337 | 1/1997 |
| WO | WO 1997/012687 | 4/1997 |
| WO | WO 1997/028801 | 8/1997 |
| WO | WO 1997/034871 | 9/1997 |
| WO | WO 1998/015280 | 4/1998 |
| WO | WO 1999/051205 | 10/1999 |
| WO | WO 1999/065464 | 12/1999 |
| WO | WO 2000/005219 | 2/2000 |
| WO | WO 2000/047200 | 8/2000 |
| WO | WO 2001/004118 | 1/2001 |
| WO | WO 2001/012167 | 2/2001 |
| WO | WO 2001/050080 A2 | 7/2001 |
| WO | WO 2001/057025 | 8/2001 |
| WO | WO 2001/076601 A2 | 10/2001 |
| WO | WO 2001/078736 | 10/2001 |
| WO | WO 2001/078739 | 10/2001 |
| WO | WO 2001/078741 | 10/2001 |
| WO | WO 2001/078743 | 10/2001 |
| WO | WO 2001/089491 | 11/2001 |
| WO | WO 2001/050080 A3 | 1/2002 |
| WO | WO 2001/076601 A3 | 2/2002 |
| WO | WO 2002/009689 | 2/2002 |
| WO | WO 2002/036106 | 5/2002 |
| WO | WO 2002/038154 | 5/2002 |
| WO | WO 2002/047667 | 6/2002 |
| WO | WO 2002/051841 | 7/2002 |
| WO | WO 2002/053564 A2 | 7/2002 |
| WO | WO 2002/060532 | 8/2002 |
| WO | WO 2002/060533 A2 | 8/2002 |
| WO | WO 2002/066422 | 8/2002 |
| WO | WO 2002/053564 A3 | 10/2002 |
| WO | WO 2002/060533 A3 | 12/2002 |
| WO | WO 2002/096423 A2 | 12/2002 |
| WO | WO 2002/096463 | 12/2002 |
| WO | WO 2003/000241 | 1/2003 |
| WO | WO 2003/000289 | 1/2003 |
| WO | WO 2003/000325 | 1/2003 |
| WO | WO 2002/096423 A3 | 2/2003 |
| WO | WO 2003/011274 A2 | 2/2003 |
| WO | WO 2003/024452 | 3/2003 |
| WO | WO 2003/042160 | 5/2003 |
| WO | WO 2003/061742 | 7/2003 |
| WO | WO 2003/066063 | 8/2003 |
| WO | WO 2003/011274 A3 | 9/2003 |
| WO | WO 2003/074025 A2 | 9/2003 |

(56) References Cited

FOREIGN PATENT DOCUMENTS

| | | |
|---|---|---|
| WO | WO 2003/087094 A2 | 10/2003 |
| WO | WO 2003/097098 | 11/2003 |
| WO | WO 2003/097613 | 11/2003 |
| WO | WO 2003/074025 A3 | 12/2003 |
| WO | WO 2004/005285 | 1/2004 |
| WO | WO 2003/087094 A3 | 3/2004 |
| WO | WO 2004/043966 | 5/2004 |
| WO | WO 2004/058729 | 7/2004 |
| WO | WO 2003/066063 A1 | 9/2004 |
| WO | WO 2004/074267 | 9/2004 |
| WO | WO 2004/074276 | 9/2004 |
| WO | WO 2004/074276 A1 | 10/2004 |
| WO | WO 2004/084896 | 10/2004 |
| WO | WO 2004/084897 | 10/2004 |
| WO | WO 2005/013993 | 2/2005 |
| WO | WO 2005/013994 | 2/2005 |
| WO | WO 2005/014005 | 2/2005 |
| WO | WO 2005/014044 | 2/2005 |
| WO | WO 2005/049581 | 6/2005 |
| WO | WO 2005/090342 | 9/2005 |
| WO | WO 2005/097126 | 10/2005 |
| WO | WO 2005/115462 | 12/2005 |
| WO | WO 2005/115463 | 12/2005 |
| WO | WO 2005/115464 | 12/2005 |
| WO | WO 2005/115465 | 12/2005 |
| WO | WO 2005/115466 | 12/2005 |
| WO | WO 2005/115467 | 12/2005 |
| WO | WO 2006/105401 | 10/2006 |
| WO | WO 2008/009397 | 1/2008 |
| WO | WO 2008/096121 | 8/2008 |
| WO | WO 2008/102128 | 8/2008 |
| WO | WO 2009/112273 A2 | 9/2009 |
| WO | WO 2009/112274 A2 | 9/2009 |
| WO | WO 2009/112273 A3 | 9/2010 |
| WO | WO 2009/112274 A3 | 9/2010 |
| WO | WO 2013/175013 | 11/2013 |
| WO | WO 2014/095663 | 6/2014 |

OTHER PUBLICATIONS

U.S. Appl. No. 10/740,264, filed Dec. 2003, Fernandez Forner et al.
U.S. Appl. No. 10/891,552, filed Jul. 2004, Meade et al.
U.S. Appl. No. 10/892,033, filed Jul. 2004, Meade et al.
U.S. Appl. No. 11/116,777, filed Apr. 2005, Fernandez Forner et al.
U.S. Appl. No. 11/141,169, filed May 2005, Gras Escardo et al.
U.S. Appl. No. 11/141,427, filed May 2005, Gras Escardo et al.
U.S. Appl. No. 11/141,428, filed May 2005, Gras Escardo et al.
U.S. Appl. No. 11/324,919, filed Jan. 2006, Fernandez Forner et al.
U.S. Appl. No. 11/325,059, filed Jan. 2006, Fernandez Forner et al.
U.S. Appl. No. 11/636,181, filed Dec. 2006, Fernandez Forner et al.
U.S. Appl. No. 12/074,929, filed Mar. 2008, Fernandez Forner et al.
U.S. Appl. No. 12/374,185, 371(c) Date Feb. 2009, Busquets Baque et al.
U.S. Appl. No. 12/528,267, 371(c) Date Aug. 2009, Beleta Supervia.
U.S. Appl. No. 12/787,772, filed May 2010, Fernandez Forner et al.
U.S. Appl. No. 12/875,601, filed Sep. 2010, Meade et al.
U.S. Appl. No. 12/912,145, filed Oct. 2010, Meade et al.
U.S. Appl. No. 12/921,892, 371(c) Date Sep. 2010, Lamarca Casado et al.
U.S. Appl. No. 12/921,921, 371(c) Date Oct. 2010, Lamarca Casado et al.
U.S. Appl. No. 13/011,131, filed Jan. 2011, Fernandez Forner et al.
U.S. Appl. No. 13/672,893, filed Nov. 2012, Lamarca Casado et al.
U.S. Appl. No. 13/692,032, filed Dec. 2012, Lamarca Casado et al.
U.S. Appl. No. 13/862,370, filed Apr. 2013, Gras Escardo et al.
U.S. Appl. No. 14/111,211, 371(c) Date Dec. 2013, Garcia Gil et al.
U.S. Appl. No. 14/403,220, 371(c) Date Nov. 2014, Lamaraca Casado et al.
U.S. Appl. No. 14/471,819, filed Aug. 2014, Gras Escardo et al.
U.S. Appl. No. 14/549,347, filed Nov. 2014, Gras Escardo et al.
U.S. Appl. No. 14/561,857, filed Dec. 2014, Beleta Supervia.
U.S. Appl. No. 14/652,817, 371(c) Date Jun. 2015, Jarreta Fernandez et al.
U.S. Appl. No. 14/712,866, filed May 2015, Fernandez Forner et al.
U.S. Appl. No. 14/795,194, filed Jul. 2015, Gras Escardo et al.
U.S. Appl. No. 14/920,519, filed Oct. 2015, Gras Escardo et al.
U.S. Appl. No. 15/019,009, filed Feb. 2016, Fernandez Forner et al.
U.S. Appl. No. 15/080,475, filed Mar. 2016, Gras Escardo et al.
U.S. Appl. No. 15/095,036, filed Apr. 2016, Fernandez Forner et al.
U.S. Appl. No. 15/159,643, filed May 2016, Gras Escardo et al.
U.S. Appl. No. 15/161,531, filed May 2016, Garcia Gil et al.
U.S. Appl. No. 15/218,391, filed Jul. 2016, Jarreta Fernandez et al.
U.S. Appl. No. 15/409,741, filed Jan. 2017, Lamaraca Casado et al.
U.S. Appl. No. 15/436,178, filed Feb. 2017, Jarreta Fernandez et al.
U.S. Appl. No. 15/688,679, filed Aug. 2017, Gras Escardo et al.
6001 Chemical Abstracts, Columbus, Ohio, U.S. vol. 104 (19), XP-002128290, May 12, 1986, p. 659.
ABPI Medicines Compendium 2003: Data Sheets for Atrovent Aerocaps, Atrovent Autohaler, Atrovent Forte MA, Atrovent Metered Dose Inhaler, Atrovent UDVs, pp. 151-155, ISBN 0 907102 20 4.
ABPI Medicines Compendium 2003: Data Sheets for Combivent Metered Aerosol, Combivent UDVs, pp. 439-441, ISBN 0 907102 20 4.
ABPI Medicines Compendium 2003: Data Sheets for Duovent Autohaler, Duovent Inhaler, Duovent UDVs, pp. 643-646, ISBN 0 907102 20 4.
ABPI Medicines Compendium 2003: Data Sheets for Oxivent Autohaler, Oxivalent Inhaler, pp. 1615-1616, ISBN 0 907102 20 4.
ABPI Medicines Compendium 2003: Data Sheets for Spiriva, pp. 1999-2001, ISBN 0 907102 20 4.
Alabaster, V., "Discovery and Development or Selective $M_3$ Antagonists for Clinical Use," Life Sciences, 1997, 60 (13/14), 1053-1060.
Amakye, D., et al., "Pharmacokinetics (PK) and Pharmacodynamics (PD) of SCIO-469, A P38 Gamma Map Kinase Inhibitor," Clinical Pharmacology & Therapeutics, 2004, 5 (2), P54: Abst PII-7.
Andersson, P., Presentation labeled "Aclidinium Bromide, A Novel Inhaled Long-Acting Anticholinergic," presented Sep. 17, 2007, 16 pages.
Atkins, P., "Dry Powder Inhalers: An Overview," Respiratory Care, 2005, 50 (10), 1304-1312.
Atrovent (ipratropium bromide) Inhalation Solution Prescribing Information, Boehringer Ingelheim International GmbH, Revised Oct. 1998, 830885-R, 7 pages.
Atrovent® Inhalation Aerosol Prescribing Information, Boehringer Ingelheim International GmbH, 10001403/US/1, 10001403/01, revised Mar. 27, 2002, 11 pages.
Atrovent® HFA Approved Labeling, Application No. 21-527, Boehringer Ingelheim International GmbH, 2004, 17 pages.
Auerbach, D. et al., "Routine Nebulized Ipratropium and Albuterol Together are Better Than Either Alone in COPD*," The COMBIVENT Inhalation Solution Study Group, Chest, 1997, 112, 1514-1521.
Avdeyev, S., "Anticholinergic Preparations in Obstructive Pulmonary Diseases," Atmosphera, 2002, No. 1, 20-23 and English-language translation (11 pages total, 7 pages translation).
Ayres, J. et al., Thorax, 1997, 52, Supplement 1, S1-S21.
Bach, P. et al., "Management of Acute Exacerbations of Chronic Obstructive Pulmonary Disease: A Summary and Appraisal of Published Evidence," Annals of Internal Medicine, 2001, 134 (7), 600-620.
Baeumer, W. et al., "Cilomilast, An Orally Active Phosphodiesterase 4 Inhibitor for the Treatment of COPD," Expert Review of Clinical Immunology, 2005, 1 (1), 27-36.
Banner, K. et al., "The Effect of Selective Phosphodiesterase 3 and 4 Isoenzyme Inhibitors and Established Anti-Asthma Drugs on Inflammatory Cell Activation," British Journal of Pharmacology, 1996, 119, 1255-1261.
Barnes, P. et al., "The Effect of Platelet Activating Factor on Pulmonary β-Adrenoceptors," British Journal of Pharmacology, 1987, 90, 709-715.
Barnes, P. et al., Eds., Asthma, vol. 2, Lippincott-Raven, Philadelphia, 1997, ISBN 0-397-51682-7, Chapter 142: Compliance by H. Mawhinney et al., pp. 2099-2113.

(56) References Cited

OTHER PUBLICATIONS

Barnes, P. et al., Eds., The Role of Anticholinergics in Chronic Obstructive Pulmonary Disease and Chronic Asthma, Gardiner-Caldwell Communications Limited, UK, 1997, ISBN 1 898729 14 X, Foreword and Chapter 9: Anticholinergics and β2-Agonists: Efficacy, Safety and Combination Therapy in Chronic Obstructive Pulmonary Disease by S.I. Rennard et al., pp. 137-144.
Barnes P., Ed., Managing Chronic Pulmonary Disease, Second Edition, Science Press Ltd, London, 2001, ISBN 1-85873-932-2, Chapter 2: Clinical Features, pp. 28-31, 35; Chapter 3: Drugs Used in the Management of COPD, pp. 40-43; Chapter 4: Management of COPD, pp. 57-62, 66; Chapter 5: Future Trends in Therapy, pp. 73-75.
Barnes, P., "Future Advances in COPD Therapy," Respiration, 2001, 68, 441-448.
Barnes, P. et al., Eds., Asthma and COPD, Basic Mechanisms and Clinical Management, Academic Press, Amsterdam, 2002, ISBN 0-12-079028-9, pp. 523, 530-531, 731.
Barnes, P., "Advances in Chronic Obstructive Pulmonary Disease," Ordinary Meeting, Jan. 13, 2003, pp. 41-51.
Barnes, P., "Chronic Obstructive Pulmonary Disease 12: New Treatments for COPD," Thorax, 2003, 58(9), 803-808.
Barnes, P., "The Role of Anticholinergics in Chronic Obstructive Pulmonary Disease," American Journal of Medicine, 2004, 117 (12A), 24S-32S.
Barnes, P., "COPD: Is There Light at the End of the Tunnel?," Current Opinion in Pharmacology, 2004, 4, 263-272.
Barnes, P. et al., "Prospects for New Drugs for Chronic Obstructive Pulmonary Disease," Lancet, 2004, 364, 985-996.
Barnes, P., "New Drugs for Asthma," Nature Reviews, Drug Discovery, 2004, 3, 831-844.
Barnes, P. et al., "COPD: Current Therapeutic Interventions and Future Approaches," European Respiratory Journal, 2005, 25 (6), 1084-1106.
Beasley, R. et al., "Withdrawal of Fenoterol and the End of the New Zealand Asthma Mortality Epidemic," International Archives of Allergy and Immunology, 1995, 107, 325-327.
Beeh, K. et al., "Aclidinium Bromide Improves Exercise Endurance and Dynamic Hyperinflation and Decreases Exertional Dyspnoea in Patients with Moderate-to-Severe COPD," Online abstract A2430 by K. Beeh et al., American Thoracic Society 2013 International Conference, American Journal of Respiratory and Critical Care Medicine, 2013, 187, A2430 (Abstract Only).
Beleta, J., "Discovery of Aclidinium Bromide: A New Long-Acting Muscarinic Antagonist for COPD," Oral Presentation, Society for Medicines Research Symposium, Sep. 11, 2007, 28 pages.
Berenbaum, M., "Synergy, Additivism and Antagonism in Immunosuppression, A Critical Review," Clinical and Experimental Immunology, 1977, 28, 1-18.
Berenbaum, M., "What is Synergy?" Pharmacological Reviews, 1989, 41, 93-141 and Errata, p. 422.
Berkow, R. et al., Eds., The Merck Manual of Diagnosis and Therapy, Sixteenth Edition, 1992, Foreword and Chapter 34, "Airways Obstruction Asthma," pp. 646-657.
Boehringer Ingelheim International GmbH, European Patent No. 1 651 270 B1 as proposed to be amended, 20 pages, first submitted to the U.S. Patent and Trademark Office in U.S. Appl. No. 12/070,298 on Oct. 19, 2009.
Bone, R. et al., "In Chronic Obstructive Pulmonary Disease, A Combination of Ipratropium and Albuterol is More Effective that Either Agent Alone: An 85-Day Multicenter Trial," COMBIVENT Inhalation Aerosol Study Group, Chest, 1994, 105, 1411-1419.
Boswell-Smith, V. et al., "Are Phosphodiesterase 4 Inhibitors Just More Theophylline?," The Journal of Allergy and Clinical Immunology, 2006, 117 (6), 1237-1243.
Boulet, L. et al., "Canadian Asthma Consensus Report, 1999," Canadian Medical Association Journal, 1999, 161 (11 Suppl), s1, s44-50.
Braunwald, E. et al., Eds., Harrison's 15$^{th}$ Edition, Principles of Internal Medicine, vol. 2, McGraw-Hill, New York, 2001, ISBN 0-07-007272-4, Section Titled: Chronic Bronchitis, Emphysema, and Airways Obstruction by E.G. Honig et al., pp. 1491, 1495-1496.
British National Formulary 45, Mar. 2003, ISBN 0 7279 1772 2, Chapter 3: Respiratory System, pp. 131-165.
British Thoracic Society, British Guideline on the Management of Asthma, Thorax, 2003, 58, Supplement I, i1-i94.
British Thoracic Society, "BTS Guidelines for the Management of Chronic Obstructive Pulmonary Disease," The COPD Guidelines Group of the Standards of Care Committee of the BTS, Thorax, 1997, 52, Supplement 5, S1-S28.
British Thoracic Society, "BTS Guidelines for the Management of Chronic Obstructive Pulmonary Disease," The COPD Guidelines Group of the Standards of Care Committee of the BTS, Thorax, 1997, 52, Supplement 5, S1-S28, retrieved Mar. 13, 2014, from thorax.bmj.com.
Brittain, H., "What Is the 'Correct' Method to Use for Particle-Size Determination?," Pharmaceutical Technology, 2001, pp. 96, 98.
Brodde, O-E., "β1- and β2-Adrenoceptors in the Human Heart: Properties, Function, and Alterations in Chronic Heart Failure," Pharmacological Reviews, 1991, 43 (2), 203-242.
Bryant, D., "Nebulized Ipratropium Bromide in the Treatment of Acute Asthma," Chest, 1985, 88 (1), 24-29.
Buhl, R. et al., "Future Directions in the Pharmacologic Therapy of Chronic Obstructive Pulmonary Disease," Proceedings of the American Thoracic Society, 2005, 2 (1), 83-93.
Burtner, R. et al., "Antispasmodics, II. Basic Esters of Some Polynuclear Carboxylic Acids," Journal of the American Chemical Society, 1943, 65, 1582-1585.
Calverley, P.M.A., Ed., Chronic Obstructive Pulmonary Disease, Chapman and Hall, London, 1995, ISBN 0 412 46450, Chapter 16: Bronchodilators: Basic Pharmacology by P.J. Barnes, pp. 391 and 398-401.
Calverley, P.M.A. et al., "Salmeterol and Fluticason Propionate and Survival in Chronic Obstructive Pulmonary Disease," New England Journal of Medicine, 2007, 356 (8), 775-789.
Cazzola, M. et al., "The Pharmacodynamic Effects of Single Inhaled Doses of Formoterol, Tiotropium and Their Combination in Patients with COPD," Pulmonary Pharmacology & Therapeutics, 2004, 17, 35-39.
Cazzola, M. et al., "The Functional Impact of Adding Salmeterol and Tiotropium in Patients with Stable COPD," Respiratory Medicine, 2004, 98, 1214-1221.
Chanez, P. et al., "Once-Daily Administration of Aclidinium Bromide, A Novel, Long-Acting Anticholinergic: A Phase II, Dose Finding Study," Published as Poster Presentation at European Respiratory Society Annual Congress in Berlin, Germany, 2008, 2 pages.
Chanez, P. et al., "Once-Daily Administration of Aclidinium Bromide, A Novel, Long-Acting Anticholinergic: A Phase II, Dose Finding Study," European Respiratory Journal, 2008, 32, 476s, Abstract 2736.
Christensen, S. et al., "1,4-Cyclohexanecarboxylates: Potent and Selective Inhibitors of Phosphodiesterase 4 for the Treatment of Asthma," Journal of Medicinal Chemistry, 1998, 41 (6), 821-835.
Chrystyn, H. et al., "The Genuair® Inhaler: A Novel Multidose Dry Powder Inhaler," International Journal of Clinical Practice, 2012, 66 (3), 309-317.
Chuchalin, A. et al., "Clinical Equivalence Trial on Budesonide Delivered Either by the Novolizer Multidose Dry Powder Inhaler or the Turbuhaler in Asthmatic Patients," Respiration, 2002, 69, 502-508.
Chung, K., "Phosphodiesterase Inhibitors in Airways Disease," European Journal of Pharmacology, 2006, 533, 110-117.
Clarkson, E. et al., "Binding and Active Transport of Large Analogues of Acetylcholine by Cholinergic Synaptic Vesicles In Vitro," Journal of Neurochemistry, 1992, 59, 695-700.
Cohen, V. et al., "Synthesis and Receptor Affinities of New 3-Quinuclidinyl α-Heteroaryl-α-aryl-α-hydroxyacetates," Journal of Pharmaceutical Sciences, 1992, 81 (4), 326-329.
Combivent Advertisement in American Journal of Respiratory and Critical Care Medicine, Feb. 1, 2003, 167 (3), 4 pages.
Combivent Advertisement in ATS 2003 Seattle 99th International Conference Final Program, May 16-21, 2003, 4 pages.

(56) References Cited

OTHER PUBLICATIONS

COMBIVENT® Advertisement in Chest, 2003, 123 (6), 4 pages.
Combivent® Inhalation Aerosol Prescribing Information, Boehringer Ingelheim International GmbH, 10000291/03, revised Sep. 2001, 12 pages.
Costain, D. et al., "Guidelines for Management of Asthma in Adults: I—Chronic Persistent Asthma," British Medical Journal, 1990, 301, 651-653.
Davis, M., et al., "New Psychotropic Agents. VI. Basic Esters of 5-Hydroxydibenzo[a,d]cycloheptadiene-5-carboxylic Acid," Journal of Medicinal Chemistry, 1963, 6, 513-516.
Davis, M. et al., "Anticonvulsants. I. Dibenzo[a,d]cycloheptadiene-5-carboxamide and Related Compounds," Journal of Medicinal Chemistry, 1964, 7, 88-94.
Dent, G. et al., "Effects of a Selective PDE4 Inhibitor, D-22888, on Human Airways and Eosinophils in vitro and Late Phase Allergic Pulmonary Eosinophilia in Guinea Pigs," Pulmonary Pharmacology & Therapeutics, 1998, 11 (1), 13-21.
Disse, B. et al., "BA 679 BR, A Novel Long-Acting Anticholinergic Bronchodilator," Life Sciences, 1993, 52, 537-544.
Disse, B. "Antimuscarinic Treatment for Lung Disease, From Research to Clinical Practice," Life Sciences, 2001, 68, 2557-2564.
Dompeling, E. et al., "Slowing the Deterioration of Asthma and Chronic Obstructive Pulmonary Disease Observed During Bronchodilator Therapy by Adding Inhaled Corticosteroids," Annals of Internal Medicine, 1993, 118, 770-778.
Drug Information Display, "Generic Name: Atropine—Oral, Brand Name(s): Sal-Tropine," obtained from www.medicinenet.com, p. 1 of 3, as of Nov. 4, 2008.
D'Urzo, A. et al., "Efficacy and Safety of Fixed-dose Combinations of Aclidinium Bromide/Formoterol Fumarate: The 24-week, Randomized, Placebo-controlled AUGMENT COPD Study," Respiratory Research, 2014, 15 (123), 18 pages.
Durham, M., "Tiotropium (Spiriva): A Once-daily Inhaled Anticholinergic Medication for Chronic Obstructive Pulmonary Disease," Baylor University Medical Center Proceedings, 2004, 17, 366-373.
Dyke, H. et al., "Update on the Therapeutic Potential of PDE4 Inhibitors," Expert Opinion on Investigational Drugs, 2002, 11 (1), 1-13.
Easton, P. et al., "A Comparison of the Bronchodilating Effects of a Beta-2 Andrenergic Agent (Albuterol) and an Anticholinergic Agent (Ipratropium Bromide), Given by Aerosol Alone or in Sequence," New England Journal of Medicine, 1986, 315 (12), 735-739.
Eglen, R. et al, "Muscarinic Receptor Subtypes and Smooth Muscle Function," Pharmacological Reviews, 1996, 48 (4), 531-565.
Eglen, R. et al., "Muscarinic Receptor Subtypes, Pharmacology and Therapeutic Potential," DN&P, 1997, 10 (8), 462-469.
English language abstract for DE10216333, retrieved from the European Patent Office website on Mar. 28, 2013, 2 pages.
English-language abstract for HU 178679, retrieved from the European Patent Office website on Nov. 21, 2003, 1 page.
English-language abstract for Romain, O. et al., "Actualites Pharmaceutiques," Archives de Pediatre, 2006, 13, 1596-1598, 1 page.
English-language abstract for WO 2003/024452, published Mar. 27, 2003, with International Publication No. WO 2003/024452.
English-language abstract for WO 2003/061742, published Jul. 31, 2003, with International Publication No. WO 2003/061742.
English-language abstract for WO 2004/074267, published Sep. 2, 2004, with International Publication No. WO 2004/074267.
English-language translation of p. 1554 of Medical Dictionary, Edited by Ishiyaku Shuppan KK, 2001, 1 page.
English-language translation of pp. 20, 23 of Pharmacology Manual, Edited by KK Nanzando, 2002, 1 page.
English-language translation of p. 96, Table 3-7 of Introduction to Pharmacology, 2003, 1 page.
English-language translation of Official Action received Mar. 25, 2009, in Russian Patent Application No. 2006147250, 3 pages.

Etzler, F. et al., "Particle Size Analysis: A Comparative Study of Various Methods," Particle & Particle Systems Characterization, 1995, 12, 217-224.
European Medicines Agency, "ICH Topic E 4, Dose Response Information to Support Drug Registration," dated Nov. 1994, CPMP/ICH/378/95, copyright 2006, 10 pages.
European Medicines Agency, Committee for Medicinal Products for Human Use (CHMP), Guideline on the Pharmaceutical Quality of Inhalation and Nasal Products, 2006, Doc. Ref.: EMEA/CHMP/QWP/49313/2005 Corr, 27 pages.
European Medicines Agency, Science Medicines Health, copyright 2014, Assessment Report—Brimica Genuair, 136 pages.
European Patent Application No. 04763322.7-2123, Third Party Observations dated Jul. 8, 2008, 6 pages.
European Patent Application No. 05750538.0-2107 Reply to Communication, dated Mar. 11, 2008, 3 pages.
European Patent Application No. 09729773.2 Communication pursuant to Article 94(3) EPC dated Apr. 24, 2013, 9 pages.
European Patent Application No. 13725154.2 Response dated Aug. 9, 2016, 3 pages.
European Patent Application No. 13725154.2 Response dated Jul. 31, 2015, 16 pages.
European Patent No. 1651270, Grounds of Opposition by Laboratorios Almirall S.A., dated Dec. 21, 2007, 12 pages.
European Patent No. 1651270, Patentee's Rebuttal to Grounds of Opposition, dated May 30, 2008, 13 pages.
European Patent No. 1651270, Reply to Submission from Patentee Dated May 30, 2008, dated May 2009, 39 pages.
European Patent No. 1651270, Patentee's Response to Summons to Attend Oral Proceedings dated Jul. 30, 2009, and Opponent's Submission of May 22, 2009, dated Oct. 1, 2009, 18 pages.
European Patent No. 1651270, Opponent's Response to Summons to Oral Proceedings, dated Jan. 14, 2010, 13 pages.
European Patent No. 1651270, Patentee's Submissions of Oral Proceedings, dated Jan. 15, 2010, 10 pages.
European Patent No. 1651270, Patentee's Response, dated Feb. 18, 2010, 7 pages.
European Patent No. 1651270, Minutes of the Oral Proceedings before the Opposition Division on Mar. 17, 2010, 7 pages.
European Patent No. 1651270, Decision Revoking the European Patent, dated May 18, 2010, 12 pages.
European Patent No. 1651270, Patentee's Appeal Requests, dated Sep. 28, 2010, 24 pages.
European Patent No. 1651270, Opponent's Reply to the Patentee's Grounds of Appeal dated Feb. 2011, 48 pages.
European Patent No. 1763368, Statement of Opposition by Boehringer Ingelheim Pharma GmbH & Co. KG, dated Dec. 2, 2009, 8 pages (in German).
European Patent No. 1763368, Statement of Opposition by Norton Healthcare Ltd, dated Nov. 9, 2009, 18 pages.
European Patent No. 1763368, Reply to Oppositions Filed against European Patent No. 1763368, dated Jul. 26, 2010, 39 pages.
European Patent No. 1763368, Opposition to European Patent No. 1763368, Patentee's Experimental Report 1, 1 page, submitted to the European Patent Office Jul. 28, 2010.
European Patent No. 1763368, Opposition to European Patent No. 1763368, Patentee's Experimental Report 2, 1 page, submitted to the European Patent Office Jul. 28, 2010.
European Patent No. 1763368, Opposition to European Patent No. 1763368, Patentee's Experimental Report 3, 8 pages, submitted to the European Patent Office Jul. 28, 2010.
European Patent No. 1763368, Opposition to European Patent No. 1763368, Patentee's Experimental Report 4, 6 pages, submitted to the European Patent Office Jul. 28, 2010.
European Patent No. 1 763 369, Notice of Opposition dated Sep. 15, 2009, and English-language translation (27 pages total, 16 pages translation).
European Pharmacopoeia 7.0, 2010, 2.9.18 Preparations for Inhalation, pp. 274-285.
Fenton, C. et al., "Novolizer®: A Multidose Dry Powder Inhaler," Drugs, 2003, 63 (22), 2437-2445.

(56) References Cited

OTHER PUBLICATIONS

Fitzgerald, M. et al., "Emerging Trends in the Therapy of COPD: Bronchodilators as Mono-and Combination Therapies," Drug Discovery Today, 2007, 12 (11/12), 472-478.
Food and Drug Administration, Center for Drug Evaluation and Research, Pharmacology Review(s), NDA No. 20-831, 151 pages Available from: http://www.acessdata.fda.gov/drugsatfda_docs/nda/2001/20831_Foradil_phrmr_P1.pdf.
Food and Drug Administration, Center for Drug Evaluation and Research, Pharmacology Review(s), NDA No. 20-833, 8 pages. Available from: http://www.acessdata.fda.gov/drugsatfda_docs/nda/2000/20833_Flovent_Pharmr.pdf.
Food and Drug Administration, Center for Drug Evaluation and Research, Pharmacology Review(s), NDA No. 21-077, 107 pages. Available from: http://www.acessdata.fda.gov/drugsatfda_docs/nda/2000/21077_Advair Diskus_biopharmr.pdf.
Food and Drug Administration, Pulmonary—Allergy Drugs Advisory Committee Meeting, Clinical Briefing Document, Spiriva, dated Sep. 6, 2002, 162 pages.
Foradil Aerolizer (formoterol formoterol) production information from Merck Product Services, downloaded May 3, 2012, from http://www.merckservices/foradil/zQzWTzPzsvlzEz4, 3 pages.
Foye, W. et al., Principles of Medicinal Chemistry, Fourth Edition, 1995, pp. 338-344.
Frijlink, H. et al., "Dry Powder Inhalers for Pulmonary Drug Delivery," Expert Opinion Drug Delivery, 2004, 1 (1), 67-86.
Frith, P. et al., "Oxitropium Bromide, Dose-Response and Time-Response Study of a New Anticholinergic Bronchodilator Drug," Chest, 1986, 89 (2), 249-253.
Fuhr, R. et al., "Efficacy and Safety of Twice-Daily Aclidinium Bromide 400 µg Compared with Placebo and Tiotropium 18 µg QD in Moderate to Severe COPD Patients," Chest, 2010, 138 (4_MeetingAbstracts): 465A, doi:10.1378/chest.9404, http://journal.publications.chestnet.org/article.aspx?articleid=1086743 accessed Nov. 30, 2015, 2 pages.
Gao, S-H. et al., "Stereochemistry of the Heterocyclic Alcohols Containing Piperidine Unit," Gaodeng Xuexiao Huaxue Xuebao, Chemical Journal of Chinese Universities, 1999, 20, 232-236.
Gavaldá, A. et al., "Aclidinium Bromide, A Novel Muscarinic Receptor Antagonist Combining Long Residence at $M_3$ Receptors and Rapid Plasma Clearance," Oral Presentation, European Respiratory Society Annual Congress, Stockholm, Sweden, Sep. 15-19, 2007, 13 pages.
Gavaldà, A. et al., "Aclidinium Bromide, A Novel Muscarinic Receptor Antagonist Combining Long Residence at $M_3$ Receptors and Rapid Plasma Clearance," Poster Presentation at the European Respiratory Society Annual Congress in Stockholm, Sweden, 2007, 2 pages.
Gavaldà, A. et al., "Aclidinium Bromide, A Novel Long-Acting Muscarinic Antagonist for COPD with Improved Preclinical Renal and Urinary Safety Profile," Life Sciences, 2012, 90, 301-305.
Gibson, L. et al., "The Inhibitory Profile of Ibudilast Against the Human Phosphodiesterase Enzyme Family," European Journal of Pharmacology, 2006, 538 (1-3), 39-42.
Global Initiative for Asthma, Global Strategy for Asthma Management and Prevention, NIH Publication No. Feb. 3659, Issued Jan. 1995, revised 2002.
Global Initiative for Chronic Obstructive Lung Disease, Global Strategy for the Diagnosis, Management, and Prevention of Chronic Obstructive Pulmonary Disease, 2006, 100 pages.
Global Initiative for Chronic Obstructive Lung Disease, Global Strategy for the Diagnosis, Management, and Prevention of Chronic Obstructive Pulmonary Disease, National Institutes of Health, National Heart, Lung, and Blood Institute, Publication No. 2701, Mar. 2001.
Godovikov, N. et al., "Synthesis and Muscarinolytic Activity of Quinuclidinyl Benzylate Iodoalkylates," Pharmaceutical Chemistry Journal, 1985, 19 (9), 602-604.
Gras, J. et al., "Aclidinium Bromide, A Novel Long-Acting Anticholinergic Drug, Has a Good Preclinical Cardiovascular Safety Profile," Published as a Poster Presentation at European Respiratory Society Annual Congress in Berlin, Germany, 2008, 2 pages.
Gras, J. et al., "The Preclinical Urinary and Renal Safety Profile of Aclidinium Bromide, A Novel Long-Acting Anticholinergic Drug," European Respiratory Society Meeting in Berlin, 2008, 1 page.
Grob, C.A. et al., "Die Synthese von 4-Brom- and 4-Hydroxy-Chinuclidin," Helvetica Chimica Acta, 1958, 41, 1184-1191.
Gross, N. et al., "Role of the Parasympathetic System in Airway Obstruction Due to Emphysema," New England Journal of Medicine, 1984, 311 (7), 421-425.
Gross, N. et al., "Dose Response to Ipratropium as a Nebulized Solution in Patients with Chronic Obstructive Pulmonary Disease, A Three-Center Study," American Review of Respiratory Disease, 1989, 139, 1188-1191.
Gross, N. et al., "Inhalation by Nebulization of Albuterol-Ipratropium Combination (Dey Combination) Is Superior to Either Agent Alone in the Treatment of Chronic Obstructive Pulmonary Disease," Respiration, 1998, 65, 354-362.
Gross, N. et al., "Efficacy and Safety of Formoterol Fumarate Delivered by Nebulization to COPD Patients," Respiratory Medicine, 2008, 102, 189-197.
Hancox, R. et al., "Randomised Trial of an Inhaled β2 Agonist, Inhaled Corticosteroid and Their Combination in the Treatment of Asthma," Thorax, 1999, 54, 482-487.
Hansel, T. et al., Eds., New Drugs for Asthma, Allergy and COPD, Progress in Respiratory Research, Karger, Basel, 2001, 31, ISBN 3805568622, Selection Titled: Current Therapy for Asthma by P.J. Barnes, pp. 6-10.
Hansel, T. et al., Eds., An Atlas of Chronic Obstructive Pulmonary Disease, COPD, The Parthenon Publishing Group, London, 2004, ISBN 1-84214-004-3, pp. 85-89, 103, 136, 139, 140, 151-156, 168-170, 210-212.
Hardman, J. et al., Eds., Goodman and Gilman's: The Pharmacological Basis of Therapeutics, Ninth Edition, McGraw-Hill, New York, 1996, Chapter 28: Drugs Used in the Treatment of Asthma by W. Serafin, pp. 659-682.
Hardman, J. et al., Eds., Goodman and Gilman's: The Pharmacological Basis of Therapeutics, Tenth Edition, McGraw-Hill, New York, 2001, ISBN 0-07-135469-7, Chapter 3: Principles of Therapeutics by A.S. Nies, pp. 45-66.
Hardman, J. et al., Eds., Goodman and Gilman's: The Pharmacological Basis of Therapeutics, Tenth Edition, McGraw-Hill, New York, 2001, ISBN 0-07-135469-7, Chapter 7: Muscarinic Receptor Agonists and Antagonists by J.H. Brown et al., pp. 155-173.
Hardman, J. et al., Eds., Goodman and Gilman's: The Pharmacological Basis of Therapeutics, Tenth Edition, MCGraw-Hill, New York, 2001, ISBN 0-07-135469-7, Chapter 10: Catecholamines, Sympathomimetic Drugs, and Adrenergie Receptor Antagonists by B.B. Hoffman, pp. 215-232
Hardman, J. et al., Eds., Goodman and Gilman's: The Pharmacological Basis of Therapeutics, Tenth Edition, McGraw-Hill, New York, 2001, ISBN 0-07-135469-7, Chapter 28: Drugs Used in the Treatment of Asthma by B.J. Undem et al., pp. 733-754.
Heacock, R. et al., "Materials and Methods," The Annals of Applied Biology, Marsh, R.W. and Thomas, I., Eds., Cambridge at the University Press, 1958, 46, 356-365.
Hele, D., "New Approaches to the Modulation of Inflammatory Processes in Airway Disease Models: ATS May 18-23, 2001, San Francisco," Respiratory Research, 2001, 2 (5), E003, 4 pages.
Huang, Z. et al., "Preferential Inhibition of Human Phosphodiesterase 4 by Ibudilast," Life Sciences, 2006, 78 (23), 2663-2668.
India Patent No. 244472, Opposition Affadavit of Dr. S. G. Deshpande, dated Jun. 5, 2012, 17 pages.
International Search Report dated Nov. 15, 2007, for International Application No. PCT/EP2007/006278 (WO2008/009397 A1), 2 pages.
International Search Report and Written Opinion of the ISR/EP for International Application No. PCT/EP2008/000782 dated Apr. 18, 2008, 12 pages.
International Search Report for International Application No. PCT/EP2012/056575 dated Jun. 4, 2012, 4 pages.
International Search Report for International Application No. PCT/EP2013/060808 dated Jul. 16, 2013, 4 pages.

(56) References Cited

OTHER PUBLICATIONS

International Search Report for International Application No. PCT/EP2013/076606 dated Jan. 22, 2014, 4 pages.
Introduction to Pharmacology, 2003, pp. 96 and 181-188.
Johnson, M., "Salmeterol," Medicinal Research Reviews, 1995, 15 (3), 225-257.
Johnson, M. "Beta$_2$-Andrenoreceptors Mechanisms of Action of Beta$_2$-Agonists," Pediatric Respiratory Reviews, 2001, 2, 57-62.
Jones, P. et al., "Efficacy and Safety of Once-daily Aclidinium in Chronic Obstructive Pulmonary Disease," Respiratory Research, 2011, 12, 55, 10 pages.
Jones, P. et al., "Efficacy and Safety of Twice-daily Aclidinium Bromide in COPD Patients: the ATTAIN Study," European Respiratory Journal, 2012, 40, 830-836.
Joos, G. et al., "Bronchodilator Effects of Aclidinium Bromide, A Novel Long-Acting Anticholinergic, in COPD Patients: A Phase II Study," Abstract 1299 from European Respiratory Society, 2007, pp. 209S-210S, retrieved from http://www.ersnet.org/learning_resources_player/abstract_print_07/files/138.pdf [retrieved on Jul. 10, 2008].
Joos, G. et al., Poster "Bronchodilator Effects of Aclidinium Bromide, A Novel Long-Acting Anticholinergic, in COPD Patients: A Phase II Study," presented at the Annual Congress of the European Respiratory Society (ERS) in Stockholm, Sweden, 2007, 4 pages.
Joos, G. et al., Poster "Bronchodilator Effects of Aclidinium Bromide, A Novel Long-Acting Anticholinergic, in COPD Patients: A Phase II Study," presented at the Annual Congress of the European Respiratory Society (ERS) in Stockholm, Sweden, 2007; Enlarged Figures 2(a), 2(b) and 3 of poster, 3 pages.
Joos, G. et al., Poster presented at the Annual Congress of the European Respiratory Society (ERS) in Stockholm, Sweden, 2007; Printout of the ERS webpage relating to the presentation, 2 pages.
Joos, G. et al., "Bronchodilatory Effects of Aclidinium Bromide, A Long-Acting Muscarinic Antagonist in COPD Patients," Respiratory Medicine, 2010, 104, 865-872.
Joos, G. et al., "Bronchodilator Effects of Aclidinium Bromide, A Novel Long-Acting Anticholinergic, in COPD Patients: A Phase II Study," Oral Presentation, European Respiratory Society Annual Congress, Stockholm, Sweden, Sep. 15-19, 2007, 16 pages.
Katzung, B., Ed., Basic and Clinical Pharmacology, Eighth Edition, McGraw-Hill, New York, 2001, ISBN 0-8385-0598-8, Chapter 20: Drugs used in Asthma by H.A. Boushey, pp. 333-349.
Kerwin, E. et al., "Efficacy and Safety of a 12-week Treatment with Twice-Daily Aclidinium Bromide in COPD Patients (ACCORD COPD I)," COPD: Journal of Chronic Obstructive Pulmonary Disease, 2012, 9 (2), 90-101.
Khan, S. et al., "Effect of the Long-Acting Tachykinin NK$_1$ Receptor Antagonist MEN 11467 on Tracheal Mucus Secretion in Allergic Ferrets," British Journal of Pharmacology, 2001, 132 (1), 189-196.
Konzett, H. et al., "Versuchsanordnung zu Untersuchungnen an der Bronchialmuskulatur," Archiv für Experimentelle Pathologie and Pharmakologie, 1940, 195, 71-74.
Kreese, H., "Almirall: Slowly Moving Forward with Aclidinium Bromide," Oct. 15, 2008, article available at: http://www.pharmaceutical-business-review.com, 1 page.
Kuča, K. et al., "A General Method for the Quaternization of N,N-Dimethyl Benzylamines with Long Chain N-Alkylbromides," Journal of Applied Biomedicine, 2004, 2, 195-198.
Kumar, R. et al., "Inhibition of Inflammation and Remodeling by Roflumilast and Dexamethasone in Murine Chronic Asthma," The Journal of Pharmacology and Experimental Therapeutics, 2003, 307 (1), 349-355.
Kumazawa, T. et al., "Inhibitors of Acyl-CoA: Cholesterol Acyltransferase. 1. Synthesis and Hypocholesterolemic Activity of Dibenz[b,e]oxepin-11-carboxanilides," Journal of Medicinal Chemistry, 1994, 37 (6), 804-810.
*Laboratorios Almirall S.A.* v. *Boehringer Ingelheim International Gmbh* (2009) EWHC (CH) (Patent) HC 07 C0 2104 (Eng.) (Unpublished); Declaration from Dr. Ramon Bosser confirming the availability of D2 and D3, dated Dec. 13, 2007.

Letter dated Jun. 6, 2008, from Powell Gilbert LLP to Bristows regarding HC07 C02104, 6 pages.
*Laboratorios Almirall S.A.* v. *Boehringer Ingelheim International GmbH* (2009) EWHC (CH) (Patent) HC 07 C0 2104 (Eng.) (Unpublished); Claimant's Notice of Experiments in Reply, served Aug. 15, 2008.
*Laboratorios Almirall S.A.* v. *Boehringer Ingelheim International Gmbh* (2009) EWHC (CH) (Patent) HC 07 C0 2104 (Eng.) (Unpublished); First Expert Report of Professor Peter John Barnes, dated Sep. 29, 2008.
*Laboratorios Almirall S.A.* v. *Boehringer Ingelheim International Gmbh* (2009) EWHC (CH) (Patent) HC 07 C0 2104 (Eng.) (Unpublished); Opponent's Experimental Report 1.
*Laboratorios Almirall S.A.* v. *Boehringer Ingelheim International GmbH* (2009) EWHC (CH) (Patent) HC 07 C0 2104 (Eng.) (Unpublished); Opponent's Experimental Report 2.
*Laboratorios Almirall S.A.* v. *Boehringer Ingelheim International Gmbh* (2009) EWHC (CH) (Patent) HC 07 C0 2104 (Eng.) (Unpublished); First Expert Report of Professor Johan Zaagsma dated Sep. 30, 2008, statistical analysis of 90-180 minute timeframe, calculation of confidence interval for differences between AUC of measured effects of the combination and calculated sum (p value) according to (b) and (c) method analysis; and heart rate data.
*Laboratorios Almirall S.A.* v. *Boehringer Ingelheim International Gmbh* (2009) EWHC (CH) (Patent) HC 07 C0 2104 (Eng.) (Unpublished); Witness Statement of Thierry Benoit Bouyssou, dated Sep. 30, 2008.
*Laboratorios Almirall S.A.* v. *Boehringer Ingelheim International Gmbh* (2009) EWHC (CH) (Patent) HC 07 C0 2104 (Eng.) (Unpublished); Witness Statement of Ramon Bosser dated Oct. 1, 2008.
*Laboratorios Almirall S.A.* v. *Boehringer Ingelheim International GmbH* (2009) EWHC (CH) (Patent) HC 07 C0 2104 (Eng.) (Unpublished); First Expert Report of Clive Peter Page dated Oct. 3, 2008.
*Laboratorios Almirall S.A.* v. *Boehringer Ingelheim International Gmbh* (2009) EWHC (CH) (Patent) HC 07 C0 2104 (Eng.) (Unpublished); First Expert Report of John Francis Costello dated Oct. 3, 2008.
*Laboratorios Almirall S.A.* v. *Boehringer Ingelheim International Gmbh* (2009) EWHC (CH) (Patent) HC 07 C0 2104 (Eng.) (Unpublished); Second Expert Report of John Francis Costello dated Oct. 23, 2008.
*Laboratorios Almirall S.A.* v. *Boehringer Ingelheim International Gmbh* (2009) EWHC (CH) (Patent) HC 07 C0 2104 (Eng.) (Unpublished); Second Expert Report of Clive Peter Page dated Oct. 27, 2008, and statistical analysis of Boehringer Experiment.
*Laboratorios Almirall S.A.* v. *Boehringer Ingelheim International Gmbh* (2009) EWHC (CH) (Patent) HC 07 C0 2104 (Eng.) (Unpublished); Second Expert Report of Professor Johan Zaagsma dated Oct. 27, 2008.
*Laboratorios Almirall S.A.* v. *Boehringer Ingelheim International Gmbh* (2009) EWHC (CH) (Patent) HC 07 C0 2104 (Eng.) (Unpublished); Second Expert Report of Professor Peter John Barnes dated Oct. 27, 2008.
*Laboratorios Almirall S.A.* v. *Boehringer Ingelheim International Gmbh* (2009) EWHC (CH) (Patent) HC 07 C0 2104 (Eng.) (Unpublished); Third Expert Report of Professor Johan Zaagsma dated Nov. 4, 2008.
*Laboratorios Almirall S.A.* v. *Boehringer Ingelheim International Gmbh* (2009) EWHC (CH) (Patent) HC 07 C0 2104 (Eng.) (Unpublished); Third Expert Report of Clive Peter Page dated Nov. 7, 2008.
*Laboratorios Almirall S.A.* v. *Boehringer Ingelheim International GmbH* (2009) EWHC (CH) (Patent) HC 07 C0 2104 (Eng.) (Unpublished), English High Court Judgment, 93 pages.
Larsson, K., "Aspects on Pathophysiological Mechanisms in COPD," Journal of Internal Medicine, 2007, 262, 311-340.
Larsson, L. et al., "The Hydrogen Bond Condition in Some Anticholinergic Esters of Glycolic Acids. I," Acta Pharmaceutica Suecica, 1974, 11, 304-308.
Le Souëf, P., "The Meaning of Lung Dose," Allergy, 1999, 54, 93-96.
Lipworth, B. et al., "Pharmacokinetics of Inhaled Drugs," Br J Clin Pharmacol, 1996, 42, 697-705.

(56) References Cited

OTHER PUBLICATIONS

Littner, M. et al., "Long-Acting Bronchodilation with Once-Daily Dosing of Tiotropium (Spiriva) in Stable Chronic Obstructive Pulmonary Disease," American Journal of Respiratory and Critical Care Medicine, 2000, 161, 1136-1142.

Lopez-Vidriero, M. et al., "Effect of Atropine on Sputum Production," Thorax, 1975, 30, 543-547.

Lötvall, J. et al., "Similar Bronchodilation with Formoterol Delivered by Aerolizer or Turbuhaler," Canadian Respiratory Journal, 1999, 6 (5), 412-416.

Lu, S. et al., "An Oral Selective M3 Cholinergic Receptor Antagonist in COPD," European Respiratory Journal, 2006, 28, 772-780.

Lund, H. et al., "Quaternization Reactions," Acta Chemica Scandinavica, 1973, 27, 383-390.

Lygo, B. et al., "Asymmetric Approaches to 2-Hydroxymethylquinuclidine Derivatives," Tetrahedron, 1999, 55, 2795-2810.

Maesen, F.P.V. et al., "Ba 679 Br, A New Long-Acting Antimuscarinic Bronchodilator: A Pilot Dose-Escalation Study in COPD," European Respiratory Journal, 1993, 6, 1031-1036.

Magnussen, H. et al., "Peak Inspiratory Flow Through the Genuair® Inhaler in Patients with Moderate or Severe COPD," Respiratory Medicine, 2009, 103, 1832-1837.

Magnussen, H. et al., "The Effect of Aclidinium Bromide 400 μg on Sleep Quality in COPD: A Pilot Study," European Respiratory Journal, 2016, 48, PA4051 (Abstract), 1 page.

Magnussen, H. et al., "The Effect of Aclidinium Bromide 400 μg on Sleep Quality in COPD: A Pilot Study," Poster Presentation, European Respiratory Congress, London, UK, Sep. 3-7, 2016, 1 page.

Maltais, F. et al., "Aclidinium Bromide Improves Exercise Endurance and Lung Hyperinflation in Patients with Moderate to Severe COPD," Respiratory Medicine, 2011, 105, 580-587.

Martin, L., "Drugs for Asthma/COPD—A Medical Primer for Physicians," http://www.lakesidepress.com/pulmonary/Asthma-Rx.html, updated Feb. 1999, 10 pages (retrieved Apr. 7, 2006 from http://www.lakesidepress.com/pulmonary/Asthma-Rx.htm).

Mashkovskiy, M.D., Medicaments, Moscow, Novaya Volna, 2001, p. 11.

Matera, M. et al., "Ultra-Long-Acting β2-Adrenoceptor Agonists," Drugs, 2007, 67 (4), 503-515.

May, E. et al., "Studies in the Anthracene Series. V. A Novel Rearrangement in the Reaction of Halomethyl Ketones with Secondary Amines," Journal of the American Chemical Society, 1948, 70, 1077-1079.

Medical Dictionary, Edited by Ishiyaku Shuppan KK, 2001, p. 1554.

Merck Manual Home Edition articles titled "Bronchopulmonary Dysplasia (BPD)," 2 pages; "Langerhans' Cell Granulomatosis," 2 pages; "Respiratory Tract Infections," 3 pages; "Pulmonary Embolism," 5 pages; and "Lung Cancer" 5 pages; accessed May 14, 2007.

Merck Manual Home Edition article titled "Severe Acute Respiratory (SARS)," 2 pages, accessed Jul. 11, 2007.

Méry, P-F. et al., "Muscarinic Regulation of the L-Type Calcium Current in Isolated Cardiac Myocytes," Life Sciences, 1997, 60 (13-14), 1113-1120.

Meyers, A. et al., "Resolution of α-Substituted Mandelic Acids via Chiral Oxazolines Using Pressurized Chromatography," Journal of Organic Chemistry, 1980, 45 (14), 2912-2914.

Mikhailov, L., Desk Book of the Physician for Clinical Pharmacology, Chapter 16, "Clinicopharmacological Characteristic of Preparations Used for Treatment of Disorders of CNS Functions," St. Petersburg, 2001, pp. 424-425, 428, 439-440 and English-language translation (12 pages total, 6 pages translation).

Miller, M. et al., "Standardisation of Spirometry," European Respiratory Journal, 2005, 26 (2), 319-338.

Mintzer, J. et al., "Anticholinergic Side-Effects of Drugs in Elderly People," Journal of the Royal Society of Medicine, 2000, 93 (9), 457-462.

Miralpeix, M. et al., "Assessment of the Potency and Duration of Action of Aclidinium Bromide in Guinea Pig Isolated Trachea In Vitro," European Respiratory Journal, 2007, 30, 357s-361s, Abstract P2159.

Miralpeix, M. et al., "Assessment of the Potency and Duration of Action of Aclidinium Bromide in Guinea Pig Isolated Trachea In Vitro," Poster Presentation, European Respiratory Society Annual Congress, Stockholm, Sweden, Sep. 15-19, 2007, 1 page.

Miralpeix, M. et. al., "The Inhaled Anticholinergic Agent, Aclidinium Bromide, Reverses Cholinergic-Induced Bronchoconstriction in Guinea Pigs with a Fast Onset of Action and a Long Duration of Effect," Published as a Poster Presentation at the European Respiratory Society Annual Congress, Berlin, Germany, 2008 (2 pages).

Molfino, N. "Drugs in Clinical Development for Chronic Obstructive Pulmonary Disease," Respiration, 2005, 72 (1), 105-112.

Montero, J. et al., "Effect of Aclidinium Bromide, A Novel Long-Acting Anticholinergic, on Salivation, Colonic Motility and Faecal Output in Different Animal Models," European Respiratory Society Meeting in Berlin, 2008, 1 page.

Murray, J. et al., Eds., Textbook of Respiratory Medicine, Third Edition, W.B. Saunders Company, Philadelphia, 2000, ISBN 0-7216-7711-8, Chapter 10: Respiratory Pharmacology by P.J. Barnes, pp. 231, 232, 252-265.

Murray, J. et al., Eds., Textbook of Respiratory Medicine, Third Edition, W.B. Saunders Company, Philadelphia, 2000, ISBN 0-7216-7711-8, Chapter 11: Airway Pharmacology by P.J. Barnes, pp. 267-296.

Murray, J. et al., Eds., Textbook of Respiratory Medicine, Third Edition, W.B. Saunders Company, Philadelphia, 2000, ISBN 0-7216-7711-8, Chapter 38: Chronic Bronchitis and Emphysema by C.A. Piquette, pp. 1187-1245.

Murray, J. et al., Eds., Textbook of Respiratory Medicine, Third Edition, W.B. Saunders Company, Philadelphia, 2000, ISBN 0-7216-7711-8, Chapter 39: Asthma by H.A. Boushey et al., pp. 1247-1289.

Murray, J. et al., Eds., Textbook of Respiratory Medicine, Third Edition, W.B. Saunders Company, Philadelphia, 2000, ISBN 0-7216-7711-8, Chapters 11 and 38, pp. 267-296 and 11871245.

National Sleep Foundation, "Asthma and Sleep," retrieved from http://www.sleepfoundation.org/article/sleep-topics/asthma-and-sleep, cited in International Search Report for International Application No. PCT/EP2012/056575, which states document was retrieved on Sep. 19, 2011, 4 pages.

National Sleep Foundation, "COPD and Difficulty Breathing," http://www.sleepfoundation.org/article/sleep-related-problems/chronic-obstructive-pulmonary-disease-and-sleep, cited in International Search Report for International Application No. PCT/EP2012/056575, which states document was retrieved on Nov. 19, 2009, 3 pages.

Nishikawa, M. et al., "Effect of Short- and Long-Acting β2-Adrenoceptor Agonists on Pulmonary β2-Adrenoceptor Expression in Human Lung," European Journal of Pharmacology, 1996, 318, 123-129.

Nishimura, K. et al., "Additive Effect of Oxitropium Bromide in Combination with Inhaled Corticosteroids in the Treatment of Elderly Patients with Chronic Asthma," Allerology International, 1999, 48, 85-88.

Noronha-Blob, L. et al., "Stereoselective Antimuscarinic Effects of 3-Quinuclidinyl Atrolactate and 3-Quinuclidinyl Xanthene-9-carboxylate," European Journal of Pharmacology, 1992, 211 (1), 97-103.

Notification of the Preliminary Research Report for FR 0505473, dated Dec. 12, 2005, 5 pages.

Notification of the Research Report for BE 200500268, dated Nov. 3, 2005, 5 pages.

Notification of the Transmittal of the International Search Report and the Written Opinion of the International Searching Authority, or the Declaration for International Application No. PCT/EP2005/005836 dated Aug. 10, 2005, 14 pages.

Notification of the Transmittal of the International Search Report and the Written Opinion of the International Searching Authority, or the Declaration for International Application No. PCT/EP2005/005837 dated Aug. 4, 2005, 14 pages.

Notification of the Transmittal of the International Search Report and the Written Opinion of the International Searching Authority, or

(56) References Cited

OTHER PUBLICATIONS the Declaration for International Application No. PCT/EP2005/005838 dated Aug. 17, 2005, 14 pages.
Notification of the Transmittal of the International Search Report and the Written Opinion of the International Searching Authority, or the Declaration for International Application No. PCT/EP2005/005839 dated Aug. 5, 2005, 14 pages.
Notification of the Transmittal of the International Search Report and the Written Opinion of the International Searching Authority, or the Declaration for International Application No. PCT/EP2005/005840 dated Aug. 17, 2005, 14 pages.
Notification of the Transmittal of the International Search Report and the Written Opinion of the International Searching Authority, or the Declaration for International Application No. PCT/EP2005/005841 dated Aug. 8, 2005, 14 pages.
Nyberg, K. et al., "Investigations of Dithienylglycol Esters," Acta Chemica Scandinavica, 1970, 24 (5), 1590-1596.
Page, C. et al., Integrated Pharmacology, Second Edition, Mosby, Edinburgh, 2002, ISBN 0 7234 3221 X, Chapter 19: Drugs and the Pulmonary System.
Parfitt, K., Ed., Martindale: The Complete Drug Reference, Thirty-Second Edition, 1999, 745-747.
Parfitt, K., Ed., Martindale: The Complete Drug Reference, Thirty-Second Edition, 1999, 745-775.
Peretto, I. et al., "Medicinal Chemistry and Therapeutic Potential of Muscarinic M3 Antagonists," Medicinal Research Reviews, 2009, published online in Wiley InterScience, DOI 10.1002/med.20158, 36 pages.
Pharmacology Manual, Edited by KK Nanzando, 2002, pp. 20 and 23.
Pokrzywinski, R. et al., "Development and Psychometric Assessment of the COPD and Asthma Sleep Impact Scale (CASIS)," Health and Quality of Life Outcomes, 2009, 7: 98, doi:10.1186/1477-7525-7-98, 10 pages.
Prat, M. et al., "Discovery of Novel Quaternary Ammonium Derivatives of (3R)-Quinuclidinol Esters as Potent and Long-Acting Muscarinic Antagonists with Potential for Minimal Systemic Exposure after Inhaled Administration: Identification of (3R)-3-{[Hydroxy(di-2-thienyl)acetyl]oxy}-1-(3-phenoxypropyl)-1-azoniabicyclo[2.2.2]octane Bromide (Aclidinium Bromide)," Journal of Medicinal Chemistry, 2009, 52, 5076-5092.
PubMed, Down, G. et al., "Clinical Pharmacology of Cilomilast," Clinical Pharmacokinetics, 2006, 45 (3), 217-233 (abstract only), 2 pages, PMID 16509757, retrieved Jul. 25, 2006, from www.pubmed.gov.
Puddicombe, S. et al., "Involvement of the Epidermal Growth Factor Receptor in Epithelial Repair in Asthma," The FASEB Journal, 2000, 14, 1362-1374.
Rabe, K. et al., "Roflumilast—An Oral Anti-Inflammatory Treatment for Chronic Obstructive Pulmonary Disease: A Randomised Controlled Trial," The Lancet, 2005, 366 (9485), 563-571.
Rang, H et al., Eds., Pharmacology, Third Edition, 1995, Chapter 17, "The Respiratory System," pp. 351-366.
Rang, H. et al., Eds., Pharmacology, Third Edition, 1995, Chapter 17, "The Respiratory System," pp. 358-361.
Rees, P., "Bronchodilators in the Therapy of Chronic Obstructive Pulmonary Disease," European Respiratory Monograph, 1998, 7, 135-149.
Reynolds, J., Ed., Martindale: The Extra Pharmacopoeia, 29th Edition, 1989, 522.
Rigaudy, J. et al., "Cetones Derivees du Dibenzo [a,d] Cycloheptadiene. La Dibenzo-2,3-6,7 Cycloheptadienedione-4,5," Bulletin de la Société Chimique de France, 1959, 638-643.
Ringdahl, R. et al., "Facile Preparation of the Enantiomers of 3-Acetoxyquinuclidinol," Acta Pharmaceutica Suecica, 1979, 16, 281-283.
Rochester, C., Ed., Clinics in Chest Medicine, W.B. Saunders Company, Philadelphia, 2000, 21 (4), ISSN 0272-5231, Selection Titled: Update on Pharmacologic Therapy for Chronic Obstructive Pulmonary Disease by G. Ferguson, pp. 723-738.
Romain, O. et al., "Actualites Pharmaceutiques," Archives de Pediatre, 2006, 13, 1596-1598.
Rucinski, T. et al., Reuters, "Almirall Seen Likely to Repeat Lung Drug Trial," Oct. 14, 2008, article available at: http://money.aol.ca/article/almirall-seen-likely-to-repeat-lung-drug-trial/379398, 1 page.
Ryder, H., "Discovery of Aclidinium Bromide: A New Long Acting Muscarinic Antagonist for COPD," Oral Presentation, International Symposium on Advances in Synthetic and Medicinal Chemistry, St. Petersburg, Russia, Aug. 27-31, 2007, 33 pages.
Rzeszotarski, W. et al., "Affinity and Selectivity of the Optical Isomers of 3-Quinuclidinyl Benzilate and Related Muscarinic Antagonists," Journal of Medicinal Chemistry, 1988, 31, 1463-1466.
Schelfhout, V. et al., "Activity of LAS 34273, A New Long Acting Anticholinergic Antagonist," American Thoracic Society, 2003, 99th International Conference, Abstract No. A93.
Schelfhout, V. et al., "Activity of LAS 34273, A New Long Acting Anticholinergic Antagonist," Poster, ATS 2003—99th International Conference, May 2003 and Expanded Version, 4 pages.
Schelfhout, V. et al., "Activity of LAS 34273, A New Long Acting Anticholinergic Antagonist, in COPD Patients," American Thoracic Society, 2003, 99th International Conference, Abstract No. A319.
Schelfhout, V. et al., "Activity of LAS 34273, A New Long Acting Anticholinergic Antagonist, in COPD Patients," Poster, ATS 2003—99th International Conference, May 2003 and Expanded Version, 4 pages.
Schelfhout, V. et al., "Bronchodilator/Bronchoprotective Effects of Aclidinium Bromide, A Novel Long-Acting Anticholinergic: A Phase I Study," European Respiratory Journal, 2007, 30, 354s-357s, Abstract P2146.
Schelfhout, V. et al., "Bronchodilator/Bronchoprotective Effects of Aclidinium Bromide, A Novel Long-Acting Anticholinergic: A Phase I Study," Poster Presentation, European Respiratory Society Annual Congress, Stockholm, Sweden, Sep. 15-19, 2007, 1 page.
Schmidt, R., "Dose-Finding Studies in Clinical Drug Development," European Journal of Clinical Pharmacology, 1988, 34, 15-19.
Sciurba, F. et al., "Radiographic Emphysema Predicts Low Bone Mineral Density in a Tobacco-exposed Cohort," Am J Respir Crit Care Med, 2011, 183 (7), 885-890.
Search Report for Patent Application No. 1029151, dated Feb. 14, 2006, 5 pages.
Search Report for Application No. CY 3405, Date of completion of the search Jun. 28, 2006, 5 pages.
Sentellas, S. et al., "Aclidinium Bromide, A New, Long-Acting, Inhaled Muscarinic Antagonist: In vitro Plasma Inactivation and Pharmacological Activity of Its Main Metabolites," European Journal of Pharmaceutical Sciences, 2010, 39, 283-290.
Sestanj, K., "A Facile Formation of Dibenzo[a,b]cycloheptenylium Ion by Decarbonylation. Color Reactions of the Cyheptaminde Metabolites," Canadian Journal of Chemistry, 1971, 49, 664-665.
Sharma, V. et al. "Does Mammalian Heart Contain Only the M2-Muscarinic Receptor Subtype?," Life Sciences, 1997, 60 (13-14), 1023-1029.
Singh, D. et al., "A Randomised, Placebo- and Active-Controlled Dose-Finding Study of Aclidinium Bromide Administered Twice a Day in COPD Patients," Pulmonary Pharmacology & Therapeutics, 2012, 25 (3), 248-253.
Singh, D. et al., "Corrigendum to 'A Randomised, Placebo- and Active-Controlled Dose-Finding Study of Aclidinium Bromide Administered Twice a Day in COPD Patients' [Pulm Pharmacol Ther 25 (3) (2012) 248-253]," Pulmonary Pharmacology & Therapeutics, 2013, 26, 305.
Singh, D. et al., "Efficacy and Safety of Aclidinium Bromide/Formoterol Fumarate Fixed-Dose Combinations Compared with Individual Components and Placebo in Patients with COPD (ACLIFORM-COPD): A Multicentre, Randomised Study," BMC Pulmonary Medicine, 2014, 14 (178), 11 pages.
Spiriva® HandiHaler® Prescribing Information, Boehringer Ingelheim International GmbH, 59873/US/2, Sep. 2004, 19 pages.
Spiriva Prescribing Information, dated Sep. 2004, 28 pages.
Spiriva Pharmacology Reviews, Part 1, 47 pages, retrieved from http://www.accessdata.fda.gov/drugsatfda_docs/nda/2004/21-395.pdf_Spiriva_Pharmr_P1.pdf, website last accessed Mar. 6, 2014.

(56) References Cited

OTHER PUBLICATIONS

Spiriva Pharmacology Reviews, Part 2, 47 pages, retrieved Jul. 31, 2015, from http://www.accessdata.fda.gov/drugsatfda_docs/nda/2004/21-395.pdf_Spiriva_Pharmr_P2.pdf.
Spiriva Pharmacology Reviews, Part 3, 47 pages, retrieved Jul. 31, 2015, from http://www.accessdata.fda.gov/drugsatfda_docs/nda/2004/21-395.pdf_Spiriva_Pharmr_P3.pdf.
Spiriva Pharmacology Reviews, Part 4, 47 pages, retrieved Jul. 31, 2015, from http://www.accessdata.fda.gov/drugsatfda_docs/nda/2004/21-395.pdf_Spiriva_Pharmr_P4.pdf.
Spiriva Pharmacology Reviews, Part 5, 47 pages, retrieved Jul. 31, 2015, from http://www.accessdata.fda.gov/drugsatfda_docs/nda/2004/21-395.pdf_Spiriva_Pharmr_P5.pdf.
Spiriva Pharmacology Reviews, Part 6, 46 pages, retrieved Jul. 31, 2015, from http://www.accessdata.fda.gov/drugsatfda_docs/nda/2004/21-395.pdf_Spiriva_Pharmr_P6.pdf.
Spitzer, W. et al., "The Use of β-Agonists and the Risk of Death and Near Death from Asthma," New England Journal of Medicine, 1992, 326 (8), 501-506.
Steckel, H. et al., "Functionality Testing of Inhalation Grade Lactose," European Journal of Pharmaceutics and Biopharmaceutics, 2004, 57, 495-505.
STN International, Karlsruhe, File Medline, Abstract for Donohue, J., "Minimal Clinically Important Differences in COPD Lung Function," Journal of Chronic Obstructive Pulmonary Disease, 2005, 2 (1), 111-124, 1 page.
STN International, Karlsruhe, File Medline, Abstract for Singh, D. et al., "A Randomised, Placebo- and Active-Controlled Dose-Finding Study of Aclidinium Bromide Administered Twice a Day in COPD Patients," Pulmonary Pharmacology & Therapeutics, 2012, 25 (3), 248-253, abstract only, 1 page, AN 2012545128, Entered STN: Apr. 14, 2012, Last Updated on STN: Sep. 25, 2012, Entered Medline: Sep. 24, 2012.
Suissa, S. et al., "Patterns of Increasing β-Agonist Use and the Risk of Fatal or Near-Fatal Asthma," European Respiratory Journal, 1994, 7, 1602-1609.
Summary of Product Characteristics (SmPC) for "Duaklir Genuair 340 Micrograms/12 Micrograms Inhalation Powder," 35 pages, Duaklir Genuair received marketing authorization from the European Medicines Agency in 2014, SmPC is published after marketing authorization.
Summary of Product Characteristics (SmPC) for "Eklira Genuair 322 Micrograms Inhalation Powder," 36 pages, Eklira Genuair received marketing authorization from the European Medicines Agency in 2012, SmPC is published after marketing authorization.
Tang, NLS. et al., "Total daily energy expenditure in wasted chronic obstructive pulmonary disease patients," European Journal of Clinical Nutrition, 2002, 56, 282-287.
Tavakkoli, A. et al., "Drug Treatment of Asthma in the 1990s," Drugs, 1999, 57 (1), 1-8.
Teixeira, M. et al., "Phosphodiesterase (PDE)4 Inhibitors: Anti-Inflammatory Drugs of the Future?" Trends in Pharmacological Sciences, 1997, 18 (4), 164-170.
Telko, M. et al., "Dry Powder Inhaler Formulation," Respiratory Care, 2005, 50 (9), 1209-1227.
Tennant, R. et al., "Long-Acting β2-Adrenoreceptor Agonists or Tiotropium Bromide for Patients with COPD: Is Combination Therapy Justified?," Current Opinion in Pharmacology, 2003, 3, 270-276.
The Merck Manual, "Instructions for Medicine," 1997, 2, 693 and English-language translation (4 page total, 2 pages translation).
The Merck Manual of Diagnosis and Therapy, Seventeenth Edition, 1999, Foreword and Chapter 68, "Chronic Obstructive Airway Disorders," pp. 555-583.
Theolair™ Prescribing Information, 3M Pharmaceuticals, 601000, May 1998, 12 pages.
Torphy, T., "Phosphodiesterase Isozymes, Molecular Targets for Novel Antiasthma Agents," American Journal of Respiratory and Critical Care Medicine, 1998, 157 (2), 351-370.
Traunecker, W. et al., "Pharmacological Effects of a Combination of Fenoterol Hydrobromide and Ipratropium Bromide," Respiration, 1986, 50 (4), 244-251.
Ueda, I., "The Rearrangement of 10-Bromo-10,11-Dihydrodibenzo[b,f]thiepin-11-one and Related Compounds in an Alkaline Solution," Bulletin of the Chemical Society of Japan, 1975, 48 (8), 2306-2309.
U.S.: National Institute of Health, "A Trial Assessing LAS34273 in Moderate to Severe Stable Chronic Obstructive Pulmonary Disease (COPD)," updated Feb. 20, 2008, 2 pages. Available from: https://clinicaltrials.gov/archive/NCT00363896/2008_02_20.
U.S.: National Institute of Health, "Efficacy and Safety of LAS34273 in Patients with Moderate to Severe Stable Chronic Obstructive Pulmonary Disease (COPD)," updated Feb. 20, 2008, 2 pages. Available from: https://clinicaltrials.gov/archive/NCT00358436/2008_02_20.
U.S. Appl. No. 10/740,264 Requirement for Restriction/Election dated Apr. 22, 2004, 5 pages.
U.S. Appl. No. 10/740,264 Non-Final Office Action dated Jul. 22, 2004, 12 pages.
U.S. Appl. No. 10/740,264 Notice of Allowance dated Mar. 30, 2005, 8 pages.
U.S. Appl. No. 10/891,552 Non-Final Office Action dated Apr. 11, 2006, 18 pages.
U.S. Appl. No. 10/891,552 Amendment Under 37 C.F.R. § 1.111 in Response to Apr. 11, 2006, Office Action dated Sep. 19, 2006, 15 pages.
U.S. Appl. No. 10/891,552 Final Office Action dated Dec. 12, 2006, 15 pages.
U.S. Appl. No. 10/891,552 Amendment Under 37 C.F.R. § 1.116 in Response to Dec. 12, 2006, Final Office Action dated May 7, 2007, 16 pages.
U.S. Appl. No. 10/891,552 Advisory Action dated May 24, 2007, 4 pages.
U.S. Appl. No. 10/891,552 Reply to May 24, 2007, Advisory Action dated Jun. 1, 2007, 4 pages.
U.S. Appl. No. 10/891,552 Non-Final Office Action dated Aug. 22, 2007, 17 pages.
U.S. Appl. No. 10/891,552 Reply to Office Action Under 37 C.F.R. § 1.111 dated Feb. 22, 2008, 17 pages.
U.S. Appl. No. 10/891,552 Interview Summary dated Apr. 22, 2008, 4 pages.
U.S. Appl. No. 10/891,552 Non-Final Office Action dated May 12, 2008, 21 pages.
U.S. Appl. No. 10/891,552 Reply to Office Action Under 37 C.F.R. § 1.111 dated Oct. 13, 2008, 17 pages and Declaration of Thierry Benoit Bouyssou Under 37 C.F.R. § 1.132 dated Sep. 5, 2008, 6 pages.
U.S. Appl. No. 10/891,552 Final Office Action dated Jan. 7, 2009, 26 pages.
U.S. Appl. No. 10/891,552 Reply for RCE Filing dated Jun. 8, 2009, 21 pages.
U.S. Appl. No. 10/891,552 Supplemental Reply dated Jun. 24, 2009, 2 pages, and Declaration Under 37 C.F.R. § 1.132 dated Jun. 15, 2009, 6 pages.
U.S. Appl. No. 10/891,552 Non-Final Office Action dated Aug. 17, 2009, 26 pages.
U.S. Appl. No. 10/891,552 Reply to Office Action Under 37 C.F.R. § 1.111 dated Jan. 19, 2010, 15 pages.
U.S. Appl. No. 10/891,552 Supplemental Reply to Office Action dated Mar. 29, 2010, 15 pages.
U.S. Appl. No. 10/891,552 Final Office Action and Examiner-Initiated Interview Summary dated Apr. 8, 2010, 30 pages.
U.S. Appl. No. 10/891,552 Examiner-Initiated Interview Summary and Notice of Abandonment dated Nov. 4, 2010, 4 pages.
U.S. Appl. No. 10/892,033 Non-Final Office Action dated Oct. 2, 2007, 16 pages.
U.S. Appl. No. 10/892,033 Office Action Response dated Apr. 2, 2008, 18 pages.
U.S. Appl. No. 10/892,033 Non-Final Office Action dated Jul. 18, 2008, 18 pages.
U.S. Appl. No. 10/892,033 Reply dated Dec. 18, 2008, 27 pages.

(56) References Cited

OTHER PUBLICATIONS

U.S. Appl. No. 10/892,033 Final Office Action dated Mar. 2, 2009, 19 pages.
U.S. Appl. No. 10/892,033 Reply for RCE dated Aug. 3, 2009, 19 pages.
U.S. Appl. No. 10/892,033 Non-Final Office Action dated Oct. 15, 2009, 18 pages.
U.S. Appl. No. 10/892,033 Reply dated Jan. 13, 2010, 8 pages.
U.S. Appl. No. 10/892,033 Final Office Action dated Mar. 31, 2010, 18 pages.
U.S. Appl. No. 10/892,033 Reply After Final Rejection dated May 11, 2010, 10 pages.
U.S. Appl. No. 10/892,033 Advisory Action dated Jun. 3, 2010, 4 pages.
U.S. Appl. No. 10/892,033, Appeal Brief dated Aug. 30, 2010, 71 pages.
U.S. Appl. No. 10/892,033 Notice of Allowance dated Oct. 7, 2010, 9 pages.
U.S. Appl. No. 10/892,033 Issue Fee dated Oct. 26, 2010, 1 page.
U.S. Appl. No. 10/892,033 Notice of Withdrawal from Issue Branch dated Oct. 29, 2010, 1 page.
U.S. Appl. No. 10/892,033 Examiner Interview Summary Record dated Nov. 17, 2010, 3 pages.
U.S. Appl. No. 10/892,033 Notice of Allowance dated Nov. 22, 2010, 7 pages.
U.S. Appl. No. 10/892,033 Issue Fee dated Dec. 2, 2010, 4 pages.
U.S. Appl. No. 10/892,033 Notice of Withdrawal from Issue Branch dated Jan. 10, 2011, 3 pages.
U.S. Appl. No. 10/892,033 Examiner Interview Summary Record dated Feb. 2, 2011, 3 pages.
U.S. Appl. No. 10/892,033 Non-Final Office Action dated Mar. 2, 2011, 32 pages.
U.S. Appl. No. 10/892,033 Reply dated Jul. 5, 2011, 21 pages.
U.S. Appl. No. 10/892,033 Final Office Action dated Sep. 19, 2011, 41 pages.
U.S. Appl. No. 10/892,033 Applicant Initiated Interview Summary dated Nov. 16, 2011, 3 pages.
U.S. Appl. No. 10/892,033 Reply After Final Rejection dated Jan. 19, 2012, 18 pages.
U.S. Appl. No. 10/892,033 Advisory Action dated Jan. 31, 2012, 5 pages.
U.S. Appl. No. 10/892,033 Brief on Appeal Under 37 C.F.R. §41.37 dated Apr. 17, 2012, 91 pages.
U.S. Appl. No. 10/892,033 Examiner's Answer to Appeal Brief dated May 18, 2012, 26 pages.
U.S. Appl. No. 10/892,033 Reply Brief dated Jun. 21, 2012, 5 pages.
U.S. Appl. No. 10/892,033 Patent Board Decision, Appeal 2012-009895 issued May 19, 2015, 14 pages.
U.S. Appl. No. 10/892,033 Notice of Abandonment dated Aug. 3, 2015, 3 pages.
U.S. Appl. No. 11/116,777 Non-Final Office Action dated Sep. 19, 2005, 15 pages.
U.S. Appl. No. 11/116,777 Amendment and Response to Office Action dated Sep. 30, 2005, 14 pages.
U.S. Appl. No. 11/116,777 Notice of Allowance dated Dec. 21, 2005, 11 pages.
U.S. Appl. No. 11/324,919 Non-Final Office Action dated Apr. 28, 2006, 13 pages.
U.S. Appl. No. 11/324,919 Notice of Allowance dated Jan. 9, 2007, 8 pages.
U.S. Appl. No. 11/325,059 Non-Final Office Action dated Mar. 14, 2006, 12 pages.
U.S. Appl. No. 11/325,059 Notice of Allowance dated Sep. 13, 2006, 9 pages.
U.S. Appl. No. 11/409,157 Requirement for Restriction/Election dated Nov. 16, 2006, 10 pages.
U.S. Appl. No. 11/409,157 Examiner Interview Summary Record dated Feb. 7, 2007, 3 pages.
U.S. Appl. No. 11/409,157 Response to Restriction Requirement dated May 16, 2007, 7 pages.
U.S. Appl. No. 11/636,181 Non-Final Office Action dated Jul. 6, 2007, 6 pages.
U.S. Appl. No. 11/636,181 Notice of Allowance dated Nov. 23, 2007, 6 pages.
U.S. Appl. No. 12/070,298 Examiner Interview Summary Record dated Apr. 7, 2011, 4 pages.
U.S. Appl. No. 12/074,929 Non-Final Office Action dated Mar. 4, 2009, 7 pages.
U.S. Appl. No. 12/074,929 Final Office Action dated Oct. 7, 2009, 10 pages.
U.S. Appl. No. 12/074,929 Notice of Allowance dated Feb. 26, 2010, 7 pages.
U.S. Appl. No. 12/374,185 Non-Final Office Action dated Oct. 13, 2010, 26 pages.
U.S. Appl. No. 12/374,185 Notice of Allowance dated Jun. 23, 2011, 15 pages.
U.S. Appl. No. 12/528,267 Non-Final Office Action dated Sep. 28, 2011, 12 pages.
U.S. Appl. No. 12/528,267 Final Office Action dated Mar. 13, 2012, 12 pages.
U.S. Appl. No. 12/528,267 Non-Final Office Action dated Sep. 23, 2013, 18 pages.
U.S. Appl. No. 12/528,267 Applicant-Initiated Interview Summary dated Mar. 12, 2014, 4 pages.
U.S. Appl. No. 12/528,267 Final Office Action dated Jun. 6, 2014, 23 pages.
U.S. Appl. No. 12/787,772 Non-Final Office Action dated Oct. 19, 2010, 7 pages.
U.S. Appl. No. 12/787,772 Suggestion for Interference dated Nov. 23, 2010, 15 pages.
U.S. Appl. No. 12/787,772 Notice of Allowance dated Jan. 10, 2011, 12 pages.
U.S. Appl. No. 12/875,601 Interview Summary dated Jan. 27, 2011, 4 pages.
U.S. Appl. No. 12/875,601 Non-Final Office Action dated Apr. 4, 2014, 22 pages.
U.S. Appl. No. 12/875,601 Reply to Office Action Under 37 C.F.R. § 1.111 dated Oct. 3, 2014, 15 pages, and Declaration of Thierry Benoit Bouyssou Under 37 C.F.R. § 1.132 dated Sep. 5, 2008, 6 pages, and Declaration Under 37 C.F.R. § 1.132 dated Jun. 15, 2009, 6 pages.
U.S. Appl. No. 12/875,601 Non-Final Office Action dated Jan. 26, 2015, 26 pages.
U.S. Appl. No. 12/875,601 Amendment Under 37 C.F.R. § 1.111 in Response to Jan. 26, 2015, Office Action filed Jun. 5, 2015, 19 pages.
U.S. Appl. No. 12/875,601 Final Office Action dated Sep. 24, 2015, 29 pages.
U.S. Appl. No. 12/875,601 Appeal Brief filed Aug. 4, 2016, 35 pages.
U.S. Appl. No. 12/875,601 Appeal Brief filed Oct. 6, 2016, 35 pages.
U.S. Appl. No. 12/875,601 Examiner's Answer to Appeal Brief dated Dec. 15, 2016, 16 pages.
U.S. Appl. No. 12/875,601 Patent Board Decision—Examiner Affirmed, dated Mar. 15, 2018, 14 pages.
U.S. Appl. No. 12/912,145 Requirement for Restriction/Election dated Nov. 4, 2013, 10 pages.
U.S. Appl. No. 12/912,145 Amendment and Response to Requirements for Restriction and Election of Species dated Dec. 4, 2013, 16 pages.
U.S. Appl. No. 12/912,145 Non-Final Office Action dated Jan. 30, 2014, 40 pages.
U.S. Appl. No. 12/912,145 Reply dated Jun. 30, 2014, 14 pages.
U.S. Appl. No. 12/912,145 Final Office Action dated Jul. 23, 2014, 54 pages.
U.S. Appl. No. 12/912,145 Notice of Abandonment dated Feb. 6, 2015, 3 pages.
U.S. Appl. No. 12/921,892 Requirement for Restriction/Election dated Dec. 13, 2011, 10 pages.
U.S. Appl. No. 12/921,892 Non-Final Office Action dated May 11, 2012, 34 pages.

(56) References Cited

OTHER PUBLICATIONS

U.S. Appl. No. 12/921,921 Requirement for Restriction/Election dated Jan. 26, 2012, 8 pages.
U.S. Appl. No. 12/921,921 Non-Final Office Action dated Jun. 4, 2012, 34 pages.
U.S. Appl. No. 13/011,131 Non-Final Office Action dated Apr. 15, 2011, 12 pages.
U.S. Appl. No. 13/011,131 Notice of Allowance dated Oct. 20, 2011, 7 pages.
U.S. Appl. No. 13/354,873 Non-Final Office Action dated Aug. 17, 2012, 8 pages.
U.S. Appl. No. 13/354,873 Final Office Action dated Dec. 28, 2012, 4 pages.
U.S. Appl. No. 13/354,873 Notice of Allowance dated Apr. 11, 2013, 6 pages.
U.S. Appl. No. 13/672,893 Requirement for Restriction/Election dated Apr. 18, 2013, 10 pages.
U.S. Appl. No. 13/672,893 Non-Final Office Action dated Jul. 16, 2013, 19 pages.
U.S. Appl. No. 13/672,893 Final Office Action dated Jan. 29, 2014, 10 pages.
U.S. Appl. No. 13/672,893 Non-Final Office Action dated Oct. 6, 2014, 18 pages.
U.S. Appl. No. 13/672,893 Notice of Allowance and Examiner-Initiated Interview Summary dated Sep. 16, 2015, 30 pages.
U.S. Appl. No. 13/692,032 Requirement for Restriction/Election dated Jan. 28, 2014, 9 pages.
U.S. Appl. No. 13/692,032 Non-Final Office Action dated Jun. 2, 2014, 12 pages.
U.S. Appl. No. 13/692,032 Final Office Action dated Dec. 30, 2014, 15 pages.
U.S. Appl. No. 13/692,032 Non-Final Office Action dated Aug. 24, 2015, 32 pages.
U.S. Appl. No. 13/692,032 Final Office Action dated May 20, 2016, 20 pages.
U.S. Appl. No. 13/692,032 Applicant-Initiated Interview Summary dated Jan. 27, 2017, 3 pages.
U.S. Appl. No. 13/692,032 Non-Final Office dated Feb. 9, 2017, 21 pages.
U.S. Appl. No. 13/692,032 Notice of Allowance dated Jan. 18, 2018, 13 pages.
U.S. Appl. No. 13/692,032 Corrected Notice of Allowance dated Feb. 13, 2018, 5 pages.
U.S. Appl. No. 13/692,032 Corrected Notice of Allowance dated Apr. 2, 2018, 5 pages.
U.S. Appl. No. 13/939,742 Non-Final Office Action dated Sep. 6, 2013, 8 pages.
U.S. Appl. No. 13/939,742 Notice of Allowance dated Mar. 20, 2014, 8 pages.
U.S. Appl. No. 14/111,211 Non-Final Office Action dated Apr. 2, 2015, 17 pages.
U.S. Appl. No. 14/111,211 Final Office Action dated Nov. 24, 2015, 47 pages.
U.S. Appl. No. 14/305,701 Requirement for Restriction/Election dated Jul. 31, 2015, 5 pages.
U.S. Appl. No. 14/305,701 Applicant Initiated Interview Summary dated Jan. 22, 2016, 3 pages.
U.S. Appl. No. 14/305,701 Response to Election of Species Requirement dated Feb. 1, 2016, 4 pages.
U.S. Appl. No. 14/305,701 Non-Final Office Action dated May 16, 2016, 17 pages.
U.S. Appl. No. 14/305,701 Response to Non-Final Office Action dated Nov. 16, 2016, 126 pages.
U.S. Appl. No. 14/305,701 Final Office Action dated Feb. 28, 2017, 20 pages.
U.S. Appl. No. 14/305,701 Examiner-Initiated Interview Summary dated Mar. 2, 2017, 2 pages.
U.S. Appl. No. 14/311,102 Non-Final Office Action dated Jul. 25, 2014, 9 pages.
U.S. Appl. No. 14/311,102 Notice of Allowance dated Feb. 10, 2015, 7 pages.
U.S. Appl. No. 14/403,220 Requirement for Restriction/Election dated Jan. 25, 2016, 10 pages.
U.S. Appl. No. 14/403,220 Non-Final Office Action dated Jul. 20, 2016, 38 pages.
U.S. Appl. No. Requirement for Restriction/Election dated Apr. 7, 2016, 9 pages.
U.S. Appl. No. 14/561,857 Non-Final Office Action dated Feb. 15, 2017, 14 pages.
U.S. Appl. No. 14/561,857 Final Office Action dated Nov. 20, 2017, 18 pages.
U.S. Appl. No. 14/561,857 Non-Final Office Action dated Jul. 12, 2018, 15 pages.
U.S. Appl. No. 14/652,817 Non-Final Office Action dated Jan. 29, 2016, 32 pages.
U.S. Appl. No. 14/712,866 Non-Final Office Action dated Jun. 5, 2015, 9 pages.
U.S. Appl. No. 14/712,866 Notice of Allowance dated Jan. 6, 2016, 38 pages.
U.S. Appl. No. 15/019,009 Non-Final Office Action dated Oct. 12, 2016, 26 pages.
U.S. Appl. No. 15/019,009 Notice of Allowance dated Mar. 21, 2017, 10 pages.
U.S. Appl. No. 15/095,036 Non-Final Office Action dated Aug. 2, 2016, 9 pages.
U.S. Appl. No. 15/095,036 Notice of Allowance dated Feb. 17, 2017, 10 pages.
U.S. Appl. No. 15/161,531 Non-Final Office Action dated Oct. 18, 2016, 18 pages.
U.S. Appl. No. 15/161,531 Notice of Allowance dated May 11, 2017, 11 pages.
U.S. Appl. No. 15/161,531 Notice of Allowability dated Jul. 10, 2017, 31 pages.
U.S. Appl. No. 15/218,391 Non-Final Office Action dated Aug. 18, 2016, 9 pages.
U.S. Appl. No. 15/409,741 Non-Final Office Action dated May 4, 2017, 11 pages.
U.S. Appl. No. 15/436,178 Non-Final Office Action dated Dec. 28, 2017, 9 pages.
U.S. Appl. No. 15/436,178 Final Office Action dated Oct. 5, 2018, 48 pages.
U.S. Appl. No. 15/599,646 Non-Final Office Action dated Aug. 25, 2017, 11 pages.
U.S. Appl. No. 15/599,646 Notice of Allowance dated Mar. 27, 2018, 41 pages.
U.S. Appl. No. 15/688,679 Non-Final Office Action dated Aug. 7, 2018, 58 pages.
U.S. Appl. No. 16/019,855 Requirement for Restriction/Election dated Apr. 17, 2019, 8 pages.
U.S. Pharmacopeia, 2013, pp. 242-263.
Van Gestel, A. et al., "Predicting Daily Physical Activity in Patients with Chronic Obstructive Pulmonary Disease," PLOS ONE, 2012, 7 (11), e48081, 7 pages.
Van Noord, J. et al., "Comparison of Once Daily Tiotropium, Twice Daily Formoterol and the Free Combination, Once Daily, in Patients with COPD," Poster, ATS 2003—99$^{th}$ International Conference, May 2003, 1 page.
Van Noord, J.A. et al., "A randomised controlled comparison of tiotropium and ipratropium in the treatment of chronic obstructive pulmonary disease," Thorax, 2000, 55, 289-294.
Van Noord, J. et al., "Tiotropium Maintenance Therapy in Patients with COPD and the 24-h Spirometric Benefit of Adding Once or Twice Daily Formoterol During 2-week Treatment Periods," Poster, ATS 2003—99$^{th}$ International Conference, May 2003, 1 page.
Virk, D., "Sleep Disturbances in Individuals Diagnosed with Respiratory Diseases; Asthma, Bronchiectasis, COPD and Asbestosis," European Journal of Neurology, 2010, 17, Supplement 3, p. 623.
Waelbroeck, M. et al., "Binding of Selective Antagonists to Four Muscarinic Receptors (M1 to M4) in Rat Forebrain," Molecular Pharmacology, 1990, 38, 267-273.

(56) References Cited

OTHER PUBLICATIONS

Walsh, D. et al., "Synthesis and Antiallergy Activity of 4-(Diarylhydroxymethyl)-1-[3-(aryloxy)propyl]piperidines and Structurally Related Compounds," Journal of Medicinal Chemistry, 1989, 32, 105-118.

Watz, H. et al., "Physical Activity in Patients with COPD," European Respiratory Journal, 2009, 33 (2), 262-272.

Wedzicha, J. et al., Eds., The Effective Management of Chronic Obstructive Pulmonary Disease, Aesculapius Medical Press, London, 2001, ISBN 0 903044 19 7, Chapter 3: The Importance of Achieving Diagnostic Accuracy by R.A. Stockley, pp. 21-30; Chapter 4: Current Thinking on the Nature of Exacerbation and the Time Course and Recovery of Exacerbations of COPD by J.A. Wedzicha et al., pp. 33-41.

Wedzicha, J. et al., Eds., The Effective Management of Chronic Obstructive Pulmonary Disease, Aesculapius Medical Press, London, 2001, ISBN 1 903044 19 7, Chapter 5: Scientific Evidence and Expert Clinical Opinion for the Selection and Use of Bronchodilators: Clinical Decision Making in the Individual Patient by P.S. Marino et al., pp. 43-63.

WHO Drug Information, "International Nonproprietary Names for Pharmacological Substances (INN), Recommended International Nonproprietary Names: List 57," 2007, 21 (1), 53-55.

Zaagsma, J. et al. "Muscarinic Control of Airway Function," Life Sciences, 1997, 60 (13-14), 1061-1068.

Zaagsma, J. et al., Eds., Muscarinic Receptors in Airways Disease, Birkhäuser Verlag, Basel, 2001, ISBN 3-7643-5988-9, Chapter Titled: The Role of Anticholinergics in Asthma and COPD by K.R. Chapman, pp. 203-219.

\* cited by examiner

QUINUCLIDINE DERIVATIVES AND MEDICINAL COMPOSITIONS CONTAINING THE SAME

CROSS REFERENCE TO RELATED APPLICATIONS

This application is a continuation of U.S. patent application Ser. No. 15/599,646, filed May 19, 2017, which is a continuation of U.S. patent application Ser. No. 15/095,036, filed Apr. 9, 2016 (now U.S. Pat. No. 9,687,478), which is a continuation of U.S. patent application Ser. No. 14/712,866, filed May 14, 2015 (now U.S. Pat. No. 9,333,195), which is a continuation of U.S. patent application Ser. No. 14/311,102, filed Jun. 20, 2014 (now U.S. Pat. No. 9,056,100), which is a continuation of U.S. patent application Ser. No. 13/939,742, filed Jul. 11, 2013 (now U.S. Pat. No. 8,802,699), which is a continuation of U.S. patent application Ser. No. 13/354,873, filed Jan. 20, 2012 (now U.S. Pat. No. 8,513,279), which is a continuation of U.S. patent application Ser. No. 13/011,131, filed Jan. 21, 2011 (now U.S. Pat. No. 8,129,405), which is a continuation of U.S. patent application Ser. No. 12/787,772, filed May 26, 2010 (now U.S. Pat. No. 7,897,617), which is a continuation of U.S. patent application Ser. No. 12/074,929, filed Mar. 7, 2008 (now U.S. Pat. No. 7,750,023), which is a continuation of U.S. patent application Ser. No. 11/636,181, filed Dec. 8, 2006 (now U.S. Pat. No. 7,358,260), which is a continuation of U.S. patent application Ser. No. 11/325,059, filed Jan. 3, 2006 (now U.S. Pat. No. 7,196,098), which is a divisional of U.S. patent application Ser. No. 11/116,777, filed Apr. 28, 2005 (now U.S. Pat. No. 7,078,412), which is a continuation of U.S. patent application Ser. No. 10/740,264, filed Dec. 17, 2003 (now U.S. Pat. No. 7,109,210), which is a divisional of U.S. patent application Ser. No. 10/047,464, filed Jan. 14, 2002 (now U.S. Pat. No. 6,750,226), which is a continuation of International Application No. PCT/EP00/06469, filed Jul. 7, 2000, and published in English on Jan. 18, 2001, which claims the benefit of Spanish Application No. P9901580, filed Jul. 14, 1999, the contents of each of which are incorporated herein by reference.

This invention relates to new therapeutically useful quinuclidine derivatives, to some processes for their preparation and to pharmaceutical compositions containing them.

The novel structures according to the invention are antimuscarinic agents with a potent and long lasting effect. In particular, these compounds show high affinity for muscarinic $M_3$ receptors (Hm3).

In accordance with their nature as $M_3$ antagonists, the new compounds are suitable for treating the following diseases: respiratory disorders such as chronic obstructive pulmonary disease (COPD), chronic bronchitis, bronchial hyperreactivity, asthma and rhinitis; urological disorders such as urinary incontinence, pollakinuria in neuripenia pollakinuria, neurogenic or unstable bladder, cystospasm and chronic cystitis; and gastrointestinal disorders such as irritable bowel syndrome, spastic colitis, diverticulitis and peptic ulceration.

The compounds claimed are also useful for the treatment of the respiratory diseases detailed above in association with p, agonists, steroids, antiallergic drugs or phosphodiesterase IV inhibitors.

Compounds of the present invention may also be expected to have anti-tussive properties.

Depending on their nature the new compounds may be suitable for treating vagally induced sinus bradycardia.

Compounds with related structures have been described as anti-spasmodics and anti-cholinergic agents in several patents.

For example, in patent FR 2012964 are described quinuclidinol derivatives of the formula

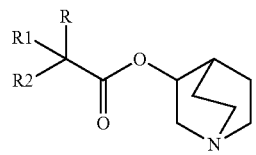

in which R is H, OH or an alkyl group having 1 to 4 carbon atoms; $R_1$ is a phenyl or thienyl group; and $R_2$ is a cyclohexyl, cyclopentyl or thienyl group, or, when R is H, $R_1$ and $R_2$ together with the carbon atom to which they are attached, form a tricyclic group of the formula:

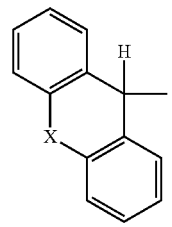

in which X is —O—, —S— or —CH$_2$—, or an acid addition or quaternary ammonium salt thereof.

EP-418716 describes thienyl carboxylate esters of formula

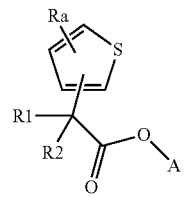

wherein A is a group

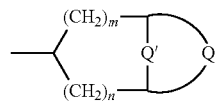

m and n=1 or 2
Q is a —CH$_2$—CH$_2$—, —CH$_2$—CH$_2$—CH$_2$—, —CH═CH—,

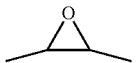

group
Q' is a ═NR or NRR' group; $R_1$ is a thienyl, phenyl, furyl, cyclopentyl or cyclohexyl group, optionally substituted; $R_2$ is H, OH, $C_1$-$C_4$ alkoxy or $C_1$-$C_4$ alkyl and $R_a$ is H, F, Cl, CH$_3$— or —NR.

U.S. Pat. No. 5,654,314 describes compounds of formula:

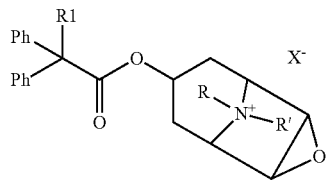

wherein R is an optionally halo- or hydroxy-substituted $C_{1-4}$ alkyl group; R is a $C_{1-4}$, alkyl group; or R and R' together form a $C_{4-6}$ alkylene group; $X^-$ is an anion; and $R_1$ is H, OH, —$CH_2OH$, $C_{1-4}$ alkyl or $C_{1-4}$ alkoxy.

The present invention provides new quinuclidine derivatives with potent antagonist activity at muscarinic $M_3$ receptors which have the chemical structure described in formula (I):

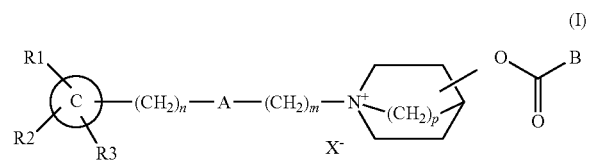

wherein:

Ⓒ is a phenyl ring, a $C_4$ to $C_9$ heteroaromatic group containing one or more heteroatoms (preferably selected from nitrogen, oxygen and sulphur atoms), or a naphthalenyl, 5,6,7,8-tetrahydronaphthalenyl or biphenyl group;

$R^1$, $R^2$ and $R^3$ each independently represent a hydrogen or halogen atom, or a hydroxy group, or a phenyl, —$OR^4$, —$SR^4$, —$NR^4R^5$, —$NHCOR^4$, —$CONR^4R^5$, —CN, —$NO_2$, —$COOR^4$ or —$CF_3$ group, or a straight or branched lower alkyl group which may optionally be substituted, for example, with a hydroxy or alkoxy group, wherein $R^4$ and $R^5$ each independently represent a hydrogen atom, straight or branched lower alkyl group, or together form an alicyclic ring; or $R^1$ and $R^2$ together form an aromatic, alicyclic or heterocyclic ring;

n is an integer from 0 to 4;

A represents a —$CH_2$—, —CH=$CR^6$—, —$CR^6$=CH—, —$CR^6R^7$—, —CO—, —O—, —S—, —S(O)—, $SO_2$ or —$NR^6$— group, wherein $R^6$ and $R^7$ each independently represent a hydrogen atom, straight or branched lower alkyl group, or $R^6$ and $R^7$ together form an alicyclic ring;

m is an integer from 0 to 8; provided that when m=0, A is not —$CH_2$—;

p is an integer from 1 to 2 and the substitution in the azoniabicyclic ring may be in the 2, 3 or 4 position including all possible configurations of the asymmetric carbons;

B represents a group of formula i) or ii):

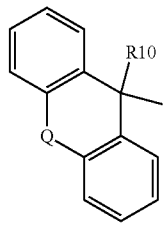

-continued

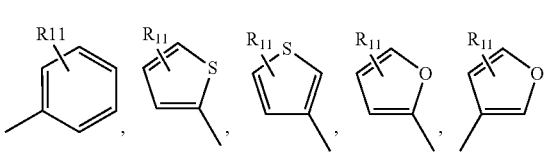

wherein $R^{10}$ represents a hydrogen atom, a hydroxy or methyl group; and $R^8$ and $R^9$ each independently represents

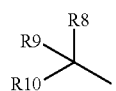

wherein $R^{11}$ represents a hydrogen or halogen atom, or a straight or branched lower alkyl group and Q represents a single bond, —$CH_2$—, —$CH_2$—$CH_2$—, —O—, —O—$CH_2$—, —S—, —S—$CH_2$— or —CH=CH—, and when i) or ii) contain a chiral centre they may represent either configuration;

X represents a pharmaceutically acceptable anion of a mono or polyvalent acid.

In the quaternary ammonium compounds of the present invention represented by formula (I) an equivalent of an anion ($X^-$) is associated with the positive charge of the N atom. $X^-$ may be an anion of various mineral acids such as, for example, chloride, bromide, iodide, sulfate, nitrate, phosphate, and organic acids such as, for example, acetate, maleate, fumarate, citrate, oxalate, succinate, tartrate, malate, mandelate, methanesulfonate and p-toluenesulfonate. $X^-$ is preferably an anion selected from chloride, bromide, iodide, sulphate, nitrate, acetate, maleate, oxalate or succinate. More preferably $X^-$ is chloride, bromide or trifluoroacetate.

The compounds of the present invention represented by the formula (I) described above, which may have one or more assymetric carbons, include all the possible stereoisomers. The single isomers and mixtures of the isomers fall within the scope of the present invention.

If any of $R^1$ to $R^7$ or $R^{11}$ represents an alkyl group, it is preferred that said alkyl group contains 1 to 8, preferably 1 to 6 and more preferably 1 to 4 carbon atoms. In particular it is preferred that any alkyl group is represented by a methyl, ethyl, propyl, including i-propyl, butyl including a n-butyl, sec-butyl and tert-butyl.

The alicyclic and heterocyclic rings mentioned in relation to formula (I) preferably comprise from 3 to 10, preferably from 5 to 7 members. The aromatic rings mentioned in relation to formula (I) above preferably contain from 6 to 14, preferably 6 or 10 members.

Preferred compounds of formula (I) are those wherein Ⓒ represents a phenyl, pyrrolyl, thienyl, furyl, biphenyl, naphthalenyl, 5,6,7,8-tetrahydronaphthalenyl, benzo[1,3]dioxolyl, imidazolyl or benzothiazolyl group, in particular a phenyl, pyrrolyl, or thienyl group; $R^1$, $R^2$ and $R^3$ each independently represent a hydrogen or halogen atom, or a hydroxyl, methyl, tert-butyl, —$CH_2OH$, 3-hydroxypropyl, —OMe, —$NMe_2$, —NHCOMe, —$CONH_2$, —CN, —$NO_2$, —COOMe or —$CF_3$ group, in particular a hydrogen atom, a hydroxy group or a halogen atom, wherein the halogen atom is preferably fluorine; n=0 or 1; m is an integer from 1 to 6, particularly 1, 2 or 3; A represents a —CH$_2$—, —CH═CH—, —CO—, —NH—, —NMe-, —O— or —S— group, in particular a —CH$_2$—, —CH═CH— or —O— group.

It is also preferred that p=2 and the substituent group —OC(O)B attached to the azoniabicyclo[2.2.2]octane is at the 3 position, preferably having the (R) configuration.

Further preferred compounds of formula I are those wherein B is a group of formula i) or ii) as defined above wherein, if B is a group of formula (i), R$^8$ and R$^9$ each independently represent a phenyl, 2-thienyl, 3-thienyl, 2-furyl or 3-furyl group, wherein R$^{11}$ is hydrogen atom; and, if B is a group of formula (ii), Q represents a single bond, —CH$_2$—, —CH$_2$—CH$_2$—, —O— or —S— group, in particular a single bond, —CH$_2$—, —CH$_2$—CH$_2$— or —O— group, most preferably a single bond or —O— group; and in any case R$^{10}$ is a hydrogen atom or a hydroxy or methyl group; and when i) or ii) contain a chiral centre they may represent either the (R) or the (S) configuration.

Most preferably the —OC(O)B group in formula (I) is diphenylacetoxy, 2-hydroxy-2,2-diphenyl-acetoxy, 2,2-diphenylpropionyloxy, 2-hydroxy-2-phenyl-2-thien-2-yl-acetoxy, 2-furan-2-yl-2-hydroxy-2-phenylacetoxy, 2,2-dithien-2-ylacetoxy, 2-hydroxy-2,2-di-thien-2-ylacetoxy, 2-hydroxy-2,2-di-thien-3-ylacetoxy, 9-hydroxy-9[H]-fluorene-9-carbonyloxy, 9-methyl-9[H]-fluorene-9-carbonyloxy, 9[H]-xanthene-9-carbonyloxy, 9-hydroxy-9[H]-xanthene-9-carbonyloxy, 9-methyl-9[H]-xanthene-9-carbonyloxy. 2,2-bis(4-fluorophenyl)-2-hydroxy acetoxy, 2-hydroxy-2,2-di-p-tolylacetoxy, 2,2-difuran-2-yl-2-hydroxy acetoxy, 2,2-dithien-2-ylpropionyloxy, 9,10-dihydroanthracene-9-carbonyloxy, 9[H]-thioxanthene-9-carbonyloxy, or 5[H]-dibenzo[a,d]cycloheptene-5-carbonyloxy. Especially preferred compounds are those wherein the —OC(O)B group in formula (I) is diphenylacetoxy, 2-hydroxy-2,2-diphenyl-acetoxy, 2,2-diphenylpropionyloxy, 2-hydroxy-2-phenyl-2-thien-2-yl-acetoxy, 2-furan-2-yl-2-hydroxy-2-phenylacetoxy, 2,2-dithien-2-ylacetoxy, 2-hydroxy-2,2-di-thien-2-ylacetoxy, 2-hydroxy-2,2-di-thien-3-ylacetoxy, 9-hydroxy-9[H]-fluorene-9-carbonyloxy, 9-methyl-9[H]-fluorene-9-carbonyloxy, 9[H]-xanthene-9-carbonyloxy, 9-hydroxy-9[H]-xanthene-9-carbonyloxy or 9-methyl-9[H]-xanthene-9-carbonyloxy.

The most preferred compounds of formula (I) are those wherein the azoniabicyclo group is substituted on the nitrogen atom with a 3-phenoxypropyl, 2-phenoxyethyl, 3-phenylallyl, phenethyl, 4-phenylbutyl, 3-phenylpropyl, 3-[2-hydroxyphenyl]propyl, 3-[4-fluorophenoxy]propyl, 2-benzyloxyethyl, 3-pyrrol-1-ylpropyl, 2-thien-2-ylethyl, 3-thien-2-ylpropyl, 3-phenylaminopropyl, 3-(methylphenylamino)propyl, 3-phenylsulfanylpropyl, 3-o-tolyloxypropyl, 3-(2,4,6-trimethylphenoxy)propyl, 3-(2-tert-butyl-6-methylphenoxy)propyl, 3-(biphenyl-4-yloxy)propyl, 3-(5,6,7,8-tetrahydronaphthalen-2-yloxy)-propyl, 3-(naphthalen-2-yloxy) propyl, 3-(naphthalen-1-yloxy)propyl, 3-(2-chlorophenoxy)propyl, 3-(2,4-difluorophenoxy)propyl, 3-(3-trifluoromethyl phenoxy)propyl, 3-(3-cyanophenoxy) propyl, 3-(4-cyanophenoxy) propyl, 3-(3-methoxyphenoxy) propyl, 3-(4-methoxyphenoxy)propyl, 3-(benzo[1,3]dioxol-5-yloxy)propyl, 3-(2-carbamoylphenoxy)propyl, 3-(3-dimethylaminophenoxy)propyl, 3-(4-nitrophenoxy)propyl, 3-(3-nitrophenoxy) propyl, 3-(4-acetylaminophenoxy)propyl, 3-(3-methoxycarbonylphenoxy) propyl, 3-[4-(3-hydroxypropyl) phenoxy]propyl, 3-(2-hydroxymethylphenoxy)propyl, 3-(3-hydroxymethylphenoxy) propyl, 3-(4-hydroxymethylphenoxy)propyl, 3-(2-hydroxyphenoxy) propyl, 3-(4-hydroxyphenoxy) propyl, 3-(3-hydroxyphenoxy)propyl, 4-oxo-4-thien-2-ylbutyl, 3-(1-methyl-[1H]-imidazol-2-ylsulfanyl)propyl, 3-(benzothiazol-2-yloxy)propyl, 3-benzyloxypropyl, 6-(4-phenylbutoxy)hexyl, 4-phenoxybutyl, or 2-benzyloxyethyl group. Especially preferred compounds are those wherein the azoniabicyclo group is substituted on the nitrogen atom with a 3-phenoxypropyl, 2-phenoxyethyl, 3-phenylallyl, phenethyl, 4-phenylbutyl, 3-phenylpropyl, 3-[2-hydroxyphenyl]propyl, 3-[4-fluorophenoxy]propyl, 2-benzyloxyethyl, 3-pyrrol-1-ylpropyl, 2-thien-2-ylethyl or 3-thien-2-ylpropyl group.

The following compounds are intended to illustrate but not to limit the scope of the present invention.

3(R)-Diphenylacetoxy-1-(3-phenoxy-propyl)-1-azoniabicyclo[2.2.2]octane; bromide

3(R)-(2-Hydroxy-2,2-diphenyl-acetoxy)-1-(3-phenoxypropyl)-1-azoniabicyclo[2.2.2]octane; bromide 3(R)-(2,2-Diphenylpropionyloxy)-1-(3-phenoxypropyl)-1-azoniabicyclo[2.2.2]octane; bromide 3(R)-(2-Hydroxy-2-phenyl-2-thien-2-yl-acetoxy)-1-(3-phenoxypropyl)-1-azonia-bicyclo[2.2.2]octane; bromide 3(R)-(2-Furan-2-yl-2-hydroxy-2-phenylacetoxy)-1-(3-phenylallyl)-1-azoniabicyclo[2.2.2]octane; bromide 3(R)-(2-Furan-2-yl-2-hydroxy-2-phenylacetoxy)-1-(2-phenoxyethyl)-1-azoniabicyclo[2.2.2]octane; bromide 3(R)-(2-Furan-2-yl-2-hydroxy-2-phenylacetoxy)-1-(3-phenoxypropyl)-1-azoniabicyclo[2.2.2]octane; bromide 3(R)-(2,2-Dithien-2-ylacetoxy)-1-(3-phenoxypropyl)-1-azoniabicyclo[2.2.2]octane; bromide 3(R)-(2-Hydroxy-2,2-di-thien-2-ylacetoxy)-1-phenethyl-1-azoniabicyclo[2.2.2]octane; bromide 3(R)-(2-Hydroxy-2,2-di-thien-2-ylacetoxy)-1-(4-phenylbutyl)-1-azoniabicyclo[2.2.2]octane; bromide 3(R)-(2-Hydroxy-2,2-dithien-2-ylacetoxy)-1-(3-phenoxypropyl)-1-azoniabicyclo[2.2.2]octane; bromide 1-[3-(4-Fluorophenoxy)propyl]-3(R)-(2-hydroxy-2,2-dithien-2-ylacetoxy)-1-azoniabicyclo[2.2.2]octane; chloride 3(R)-(2-Hydroxy-2,2-dithien-2-ylacetoxy)-1-[3-(2-hydroxyphenoxy)propyl]-1-azoniabicyclo[2.2.2]octane; trifluoroacetate 3(R)-(2-Hydroxy-2,2-dithien-2-ylacetoxy)-1-(3-pyrrol-1-ylpropyl)-1-azonia-bicyclo[2.2.2]octane; trifluoroacetate 3(R)-(2-Hydroxy-2,2-dithien-2-ylacetoxy)-1-(2-thien-2-ylethyl)-1-azoniabicyclo[2.2.2]octane; bromide 3(R)-(2-Hydroxy-2,2-dithien-2-ylacetoxy)-1-(3-thien-2-ylpropyl)-1-azoniabicyclo[2.2.2]octane; bromide 1-(2-Benzyloxyethyl)-3(R)-(2-hydroxy-2,2-dithien-2-ylacetoxy)-1-azoniabicyclo[2.2.2]octane; trifluoroacetate 3(R)-(2-Hydroxy-2,2-dithien-3-ylacetoxy)-1-(3-phenoxypropyl)-1-azoniabicyclo[2.2.2]octane; bromide 1-(3-phenylallyl)-3(R)-(9-Hydroxy-9[H]-fluorene-9-carbonyloxy)-1-azoniabicyclo[2.2.2]octane; bromide 3(R)-(9-Hydroxy-9[H]-fluorene-9-carbonyloxy)-1-(3-phenoxypropyl)-1-azoniabicyclo[2.2.2]octane; bromide 3(R)-(9-Hydroxy-9[H]-fluorene-9-carbonyloxy)-1-phenethyl-1-azoniabicyclo[2.2.2]octane; bromide 3(R)-(9-Hydroxy-9H-fluorene-9-carbonyloxy)-1-(3-thien-2-ylpropyl)-1-azoniabicyclo[2.2.2]octane; bromide 3(R)-(9-Methyl-9[H]-fluorene-9-carbonyloxy)-1-(3-phenylallyl)-1-azoniabicyclo [2.2.2]octane; bromide 3(R)-(9-Methyl-9[H]-fluorene-9-carbonyloxy)-1-(3-phenoxypropyl)-1-azoniabicyclo [2.2.2]octane; bromide 1-(4-Phenylbutyl)-3(R)-(9[H]-xanthene-9-carbonyloxy)-1-azoniabicyclo [2.2.2]octane; bromide 1-(2-Phenoxyethyl)-3(R)-(9[H]-xanthene-9-carbonyloxy)-1-azoniabicyclo [2.2.2]octane; bromide 1-(3-Phenoxypropyl)-3(R)-(9[H]-xanthene-9-carbonyloxy)-1-azoniabicyclo [2.2.2]octane; bromide 1-Phenethyl-3(R)-(9[H]-xanthene-9-carbonyloxy)-1-azoniabicyclo[2.2.2] octane; bromide 3(R)-(9-Hydroxy-9[H]-xanthene-9-carbonyloxy)-1-(3-phenoxypropyl)-1-azoniabicyclo[2.2.2]octane; bromide 3(R)-(9-Hydroxy-9[H]-xanthene-9-carbonyloxy)-1-phenethyl-1-azoniabicyclo[2.2.2]octane; bromide 3(R)-(9-Hydroxy-9H-xanthene-9-carbonyloxy)-1-(3-thien-2-ylpropyl)-1-azoniabicyclo[2.2.2]octane; bromide 3(R)-(9-Methyl-9[H]-xanthene-9-carbonyloxy)-1-(3-phenoxy-propyl)-1-azonia-bicyclo[2.2.2]octane; bromide The present invention also provides processes for preparing compounds of formula (I).

The quaternary ammonium derivatives of general Formula I, may be prepared by reaction of an alkylating agent of general Formula II with compounds of general Formula III. In Formulas I, II and III, $R^1$, $R^2$, $R^3$, Ⓒ, A, X, B, n, m and p are as defined above.

This alkylation reaction may be carried out by two different experimental procedures, a) and b) which are described below. In particular method b) provides a new experimental process, using solid phase extraction methodologies, that allows the parallel preparation of several compounds. Methods a) and b) are described in the experimental section. Compounds of general Formula II which are not commercially available have been prepared by synthesis according to standard methods. For example, compounds wherein n=0 and A=—O—, —S— or —$NR^6$, wherein $R^6$ is as defined above, were obtained by reaction of the corresponding aromatic derivative or its potassium salt with an alkylating agent of general formula Y—(CH$_2$)m-X, wherein X may be a halogen and Y may be a halogen or a sulphonate ester. In other examples, compounds of general Formula II, where n>=1 were synthesised from the corresponding alcohol derivative of general Formula IV by known methods.

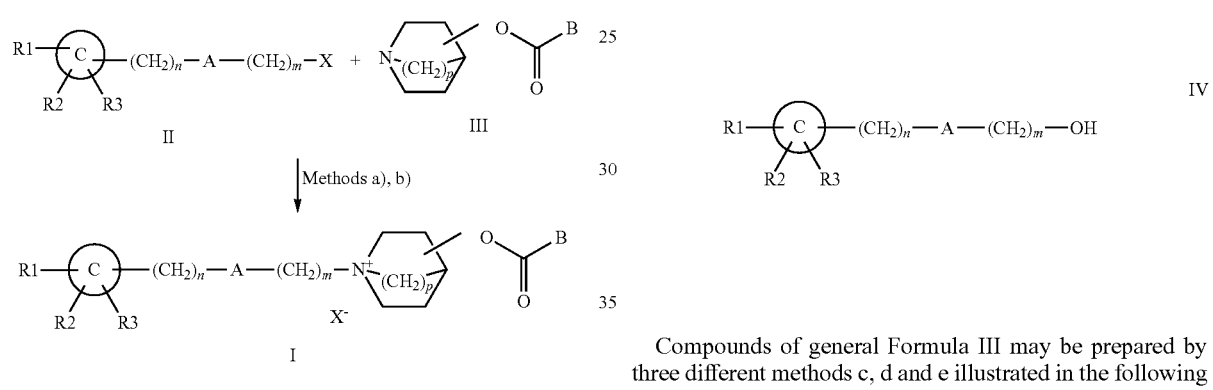

Compounds of general Formula III may be prepared by three different methods c, d and e illustrated in the following scheme and detailed in the experimental section.

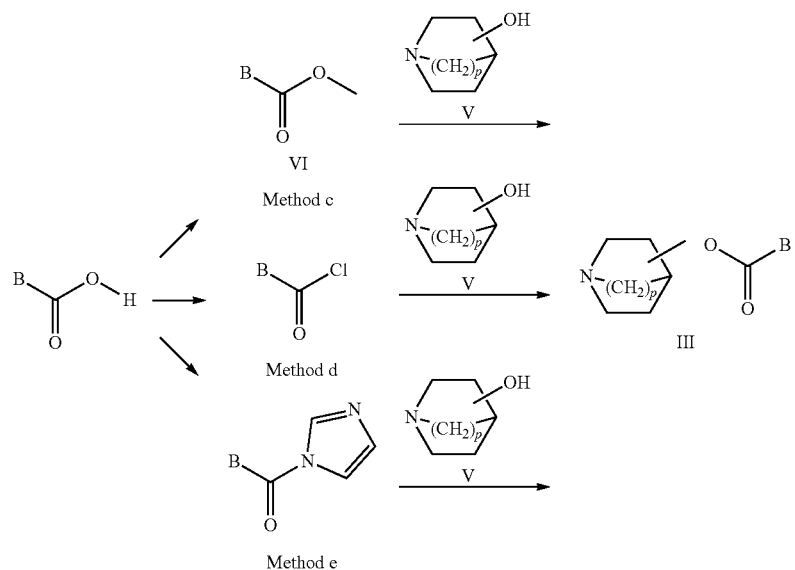

Some compounds of general formula III where B is a group of formula i), $R^8$ and $R^9$ are as described above and $R^{10}$ is a hydroxy group, may also be prepared from the glyoxalate esters of general formula VII by reaction with the corresponding organometallic derivative.

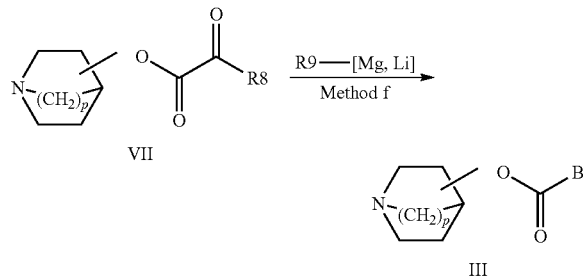

Compounds of general formula VII may be prepared from the corresponding glyoxylic acids following the standard methods c, d and e described above and detailed in the experimental section. The glyoxalate derivatives of formula VII where $R^6$ is a 2-thienyl or 2-furyl group have not been described before.

The following compounds are examples of compounds of general formula III and VII which have not been described before:

9-Methyl-9[H]-fluorene-9-carboxylic acid 1-azabicyclo[2.2.2]oct-3(R)-yl ester (intermediate I-1c);

9-Methyl-9[H]-xanthene-9-carboxylic acid 1-azabicyclo[2.2.2]oct-3(R)-yl ester (intermediate I-1d);

2-Hydroxydithien-2-yl-acetic acid 1-azabicyclo[2.2.2]oct-4-yl ester (intermediate I-4a).

Oxothien-2-yl-acetic acid 1-azabicyclo[2.2.2]oct-4-yl ester (intermediate I-4b).

Oxothien-2-yl-acetic acid 1-azabicyclo[2.2.2]oct-3(R)-yl ester (intermediate I-4 g).

Oxofuran-2-yl-acetic acid 1-azabicyclo[2.2.2]oct-3(R)-yl ester (intermediate I-4e).

2-Hydroxy-2,2-difuran-2-yl-acetic acid 1-azabicyclo[2.2.2]oct-3(R)-yl ester (intermediate I-4d).

Compounds of Formula V could be:

4-hydroxy-1-azabicyclo[2.2.1]heptane, described in WO0150080

4-hydroxy-1-azabicyclo[2.2.2]octane, described in Grob, C. A. et. al. Helv. Chim. Acta (1958), 41, 1184-1190

3(R)-hydroxy-1-azabicyclo[2.2.2]octane or 3(S)-hydroxy-1-azabicyclo[2.2.2]octane, described in Ringdahl, R. Acta Pharm. Suec. (1979), 16, 281-283 and commercially available from CU Chemie Uetikon GmbH.

The following examples are intended to illustrate, but not to limit, the experimental procedures that have been described above.

The structures of the prepared compounds were confirmed by $^1$H-NMR and MS. The NMR were recorded using a Varian 300 MHz instrument and chemical shifts are expressed as parts per million ($\delta$) from the internal reference tetramethyl silane. Their purity was determined by HPLC, using reverse phase chromatography on a Waters instrument, with values greater than 95% being obtained. Molecular ions were obtained by electrospray ionization mass spectometry on a Hewlett Packard instrument.

Method -a-

EXAMPLE 20

Preparation of 3(R)-(2-Furan-2-yl-2-hydroxy-2-phenyl acetoxy)-1-(3-phenoxypropyl)-1-azonlabicyclo[2.2.2]octane, bromide 200 mg of (Furan-2-yl)-hydroxy-phenylacetic acid 1-azabicyclo[2.2.2] oct-3(R)-yl ester (0.6 mmol) were suspended in 4 ml of CH3CN and 6 ml of CHCl3. To this suspension were added 0.48 ml (3 mmol) of 3-phenoxypropyl bromide. After stirring for 72 h at room temperature in inert atmosphere, solvents were evaporated. Ether was added and the mixture stirred. The solid obtained was filtered and washed several times with ether. The yield was 0.27 g (83%) of title compound as a mixture of diastereomers.

$^1$H-NMR (DMSO-d6): $\delta$ 1.50-2.20 (m, 6H), 2.25 (m, 1H), 3.10 (m, 1H), 3.20-3.60 (m, 6H), 3.95 (m, 1H), 4.05 (m, 2H), 5.20 (m, 1H), 6.25-6.35 (double dd, 1H), 6.45 (m, 1H), 6.95 (m, 4H), 7.30-7.50 (m, 7H), 7.70 (m, 1H); MS [M-Br]$^+$: 462; mp 166° C.

Method -b-

EXAMPLE 51

Preparation of 3(R)-(2-Hydroxy-2,2-di-thien-2-yl acetoxy)-1-[3-(naphthalen-1-yloxy)propyl]-1-azoniabicyclo[2.2.2] octane; trifluoroacetate 60 mg (0.17 mmols) of hydroxy-dithien-2-yl-acetic acid 1-aza-bicyclo[2.2.2]oct-3(R)-yl ester were dissolved in 1 ml of dmso. To this solution 188 mg (0.85 mmol) of 3-(naphthalen-1-yloxy)-propyl chloride were added. After stirring overnight at room temperature, the mixture was purified by solid phase extraction with a cation exchange Mega Bond Elut cartridge, previously conditioned at pH=7.5 with 0.1 M NaH2PO4 buffer. The reaction mixture was applied to the cartridge and washed first with 2 ml of DMSO and then three times with 5 ml of CH3CN, rinsing away all starting materials. The ammonium derivative was eluted with 5 ml of 0.03 M TFA solution in CH3CN:CHCl3 (2:1). This solution was neutralized with 300 mg of poly(4-vinylpyridine), filtered and evaporated to dryness.

The yield was 17 mg (15%) of title compound. $^1$H-NMR (DMSO-d6): $\delta$ 1.7-2.1 (m, 4H), 2.2-2.4 (m, 3H), 3.2-3.6 (m, 7H), 4.0 (m, 1H), 4.2 (t, 2H), 5.25 (m, 1H), 7.0 (m 3H), 7.2 (m, 2H), 7.4-7.6 (m, 7H), 7.85 (d, 1H), 8.2 (d, 1H); MS [M-CF$_3$COO]$^+$: 534.

Method -c-

Methyl ester derivatives of general Formula VI were prepared by standard methods of esterification from the corresponding carboxylic acid or following the procedures described in examples I-1e, I-1f and I-1g or according to procedures described in literature: FR 2012964; Larsson. L et al. Acta Pharm. Suec. (1974), 11(3), 304-308; Nyberg, K. et. al. Acta Chem. Scand. (1970), 24, 1590-1596; and Cohen, V. I. et. al. J. Pharm. Sciences (1992), 81, 326-329.

EXAMPLE I-1a

Preparation of (Furan-2-yl)hydroxyphenylacetic acid 1-azabicyclo[2.2.2]oct-3(R)-yl ester 3.24 g (0.014 mols) of (Furan-2-yl)-hydroxy-phenylacetic acid methyl ester were dissolved in 85 ml of toluene. To this solution were added 2.08 g (0.016 mols) of 3-(R)-hydroxy- 1-azabicyclo[2.2.2]octane and 0.224 g (5.6 mmols) of HNa (60% dispersion in mineral oil). The mixture was refluxed with continuous removal of distillate and when necessary replacement with fresh toluene for 1.5 hours. The cooled mixture was extracted with 2N HCl acid, the aqueous layer washed with ethyl acetate, basified with K2003 and extracted with CHCl3. The organic layer was dried over Na2SO4 and evaporated. The oil obtained (3.47 g) crystallised after cooling at room temperature. This solid was suspended in hexane and filtered. The yield was 2.5 g (54%) of a mixture of diasteroisomers, mp: 140-142° C.; GC/MS [M]$^+$: 327;

$^1$H-NMR (CDCl3): δ 1.20-1.70 (m, 4H), 1.90-2.10 (m, 1H), 2.45-2.80 (m, 5H), 3.10-3.30 (m, 1H), 4.8 (bs, OH), 4.90-5.0 (m, 1H), 6.20 (m, 1H), 6.35 (m, 1H), 7.30-7.50 (m, 4H), 7.60-7.70 (m, 2H).

After four crystallizations of 0.5 g of this mixture from boiling acetonitrile, 0.110 g of a pure diastereomer(1) were obtained. From the mother liquors of crystallization was obtained the other diastereomer (2). (*: configuration not assigned). Diastereomer 1 was hydrolysed to yield (+)-2-hydroxy-2-phenyl-2-furan-2-ylacetic acid as a pure enantiomer, $[\alpha]^{25}_D$=+5.6 (c=2, EtOH). Diastereomer 2 was hydrolysed to yield (−)-2-hydroxy-2-phenyl-2-furan-2-ylacetic acid as a pure enantiomer, $[\alpha]^{25}_D$, =−5.7 (c=2, EtOH).

Diastereomer 1: 2(*)-(Furan-2-yl)hydroxyphenylacetic acid 1-azabicyclo[2.2.2]oct-3(R)-yl ester $^1$H-NMR (CDCl3): δ 1.20-1.70 (m, 4H), 1.90 (m, 1H), 2.45-2.50 (m, 1H), 2.50-2.80 (m, 4H), 3.10-3.20 (m, 1H), 4.8 (bs, OH), 4.90-5.0 (m, 1H), 6.20 (m, 1H), 6.35 (m, 1H), 7.30-7.50 (m, 4H), 7.60-7.70 (m, 2H).

Diastereomer 2: 2(*)-(Furan-2-yl)hydroxyphenylacetic acid 1-azabicyclo[2.2.2]oct-3(R)-yl ester. $^1$H-NMR (CDCl3): δ 1.20-1.70 (m, 4H), 2.10 (m, 1H), 2.50-2.80 (m, 5H), 3.20-3.30 (m, 1H), 4.8 (bs, OH), 4.90-5.0 (m, 1H), 6.20 (m, 1H), 6.35 (m, 1H), 7.30-7.50 (m, 4H), 7.60-7.70 (m, 2H).

EXAMPLE I-1b

Preparation of Furan-2-ylhydroxythien-2-ylacetic acid 1-azabicyclo[2.2.2]oct-3(R)-yl ester Prepared as in example I-1a. The yield was 3.06 g (64.3%) of a mixture of diastereoisomers, mp: 172° C.; GC/MS [M]$^+$: 333;

$^1$H-NMR (DMSO-d6): δ 1.21-1.27 (m, 1H), 1.41-1.60 (m, 3H), 1.87 (m, 1H), 2.36-2.69 (m, 5H), 3.02-3.14 (m, 1H), 4.75-4.82 (m, 1H), 6.24-6.25 (m, 1H), 6.42-6.45 (m, 1H), 7.01-7.06 (m, 1H), 7.11-7.14 (m, 2H), 7.51-7.54 (m, 1H), 7.66-7.69 (m, 1H).

EXAMPLE I-1c

Preparation of 9-Methyl-9[H]-fluorene-9-carboxylic acid 1-azabicyclo[2.2.2]oct-3(R)-yl ester Prepared as in example I-1a. The yield was 3.34 g of an oil (80%). This product was solidified by formation of the oxalate salt (1:1), mp: 186° C. MS [M free base+1]$^+$: 334.

Oxalate salt, $^1$H-NMR (DMSO-d6): δ 1.43-1.55 (m, 2H), 1.68-1.78 (m, 2H), 1.75 (s, 3H), 2.02 (m, 1H), 2.70-2.90 (m, 1H), 2.92-3.15 (m 4H), 3.50-3.57 (m, 1H), 4.88 (m, 1H), 7.35-7.47 (m, 4H), 7.62-7.70 (m, 2H), 7.89-7.91 (m, 2H).

EXAMPLE I-1d

Preparation of 9-Methyl-9[H]-xanthene-9-carboxylic acid 1-azabicyclo[2.2.2]oct-3(R)-yl ester Prepared as in example I-1 a. The yield was 1.91 g of an oil (53%). This product was solidified by formation of the oxalate salt (1:1), mp: 152° C. MS [M free base+1]$^+$: 350.

Oxalate salt, $^1$H-NMR (DMSO-d6): δ 1.20-1.30 (m, 1H), 1.40-1.52 (m, 1H), 1.64-1.81 (m, 2H), 1.90 (s, 3H), 2.0 (m, 1H), 2.53-2.66 (m, 1H), 2.71-2.76 (m, 1H), 2.97-3.10 (m, 3H), 3.44-3.52 (m, 1H), 4.90-4.92 (m, 1H), 7.12-7.18 (m, 4H), 7.32-7.38 (m, 2H), 7.43-7.48 (m, 2H), 8.0-9.8 (bs, 1H, H$^+$).

EXAMPLE I-1e

Preparation of 9-Methyl-9[H]-fluorene-9-carboxylic acid methyl ester

Lithium diisopropylamide (26.7 ml of a 2M solution in heptane/tetrahydrofurane/ethylbenzene, 0.053 mol) was added to a stirred solution of 9[H]-fluorene-9-carboxylic acid (5 g, 0.0237 mol) in THF (70 ml) at between 0 and 5° C. in N$_2$ atmosphere. The mixture was warmed to room temperature and refluxed 1.5 hours. The reaction mixture was cooled to room temperature and a solution of CH3I (1.85 ml, 0.03 mol) in THF (1.85 ml) was added. The mixture was stirred overnight at room temperature and evaporated. To the residue in MeOH (70 ml) was added concentrated sulfuric acid (3.9 ml) in MeOH (25 ml), the mixture was refluxed for 2 hours and evaporated. The residue was partitioned between chloroform and saturated K2CO3 solution. The aqueous layer was extracted again with chloroform and the organic layers were combined, washed with water, dried over sodium sulphate and evaporated to dryness to obtain 5.73 g of a brown oil. This product was purified by column chromatography (silica gel, hexane/ ethyl acetate 95:5) to yield 4.43 g (78.5%) of a pure product, structure confirmed by $^1$H-NMR.

$^1$H-NMR (CDCl3): δ 1.80 (s, 3H), 3.60 (s, 3H), 7.50-7.65 (m, 4H), 7.75 (m, 2H), 8.0 (m, 2H).

EXAMPLE I-1f

Preparation of 9-Methyl-9[H]-xanthene-9-carboxylic acid methyl ester

Prepared as in example I-1e. The yield was 2.65 g (47.2%). $^1$H-NMR (CDCl3): δ 1.90 (s, 3H), 3.6 (s, 3H), 7.05-7.35 (m, 8H).

EXAMPLE I-1 g

Preparation of 9-Hydroxy-9 [H]-xanthene-9-carboxylic acid methyl ester

Lithium diisopropylamide (20.3 ml of a 2M solution in heptane/tetrahydrofurane/ethylbenzene, 0.041 mol) was added to a stirred solution of 7 g (0.029 mol) of 9[H]-xantene-9-carboxylic acid methyl ester (prepared by a standard method) in THF (70 ml) at between 0 and 5° C. in N, atmosphere. The mixture was stirred 1 h at this temperature and then was added by $N_2$ pressure to a dry solution of oxygen in ether at 0° C. After 30 min, an equal volum of NaHSO3, 40% aqueous solution, was added, and the reaction mixture was warmed to room temperature and stirred for 30 min. The two layers were separated and the aqueous phase was extracted twice with ethyl acetate. The organic phases were combined, treated with NaHSO3 (40% aqueous solution), washed with water, dried over sodium sulphate and evaporated to dryness to obtain 8.89 g of a brown solid.

This procedure was repeated with 5 g of starting material yielding 6.04 g of the same brown solid.

The products were combined and purified by column chromatography (silica gel, hexane/ethyl acetate 90:10) to yield 7.60 g (global Rt: 59.4%) of a pure product, structure confirmed by $^1$H-NMR.

$^1$H-NMR (DMSO-d6): δ 3.5 (s, 3H), 7.0 (s, 1H, OH), 7.2 (m, 4H), 7.4 (m, 2H), 7.55 (m, 2H).
Method -d-

EXAMPLE I-2a

Preparation of 10,11-Dihydro-5[H]-dibenzo[a,d] cycloheptane-5-carboxylic acid 1-azabicyclo[2.2.2]oct-3-(R)-yl ester 2.15 g of 10,11-Dihydro-5[H]-dibenzo[a,d]cycloheptane-5-carboxylic acid (9.0 mmol) were dissolved in 40 ml of CHCl3 (ethanol free). The solution was cooled at 0° C. and 0.86 ml of oxalyl chloride (9.9 mmols) and a drop of DMF were added. The mixture was stirred and allowed warm to room temperature. After an hour at this temperature the solvents were evaporated and the residue was dissolved in CHCl3 and evaporated again. This procedure was repeated two times. The obtained oil was dissolved in 20 ml of toluene and added to a solution of 1.26 g (9.9 mmol) of 3-(R)-hydroxy-1-azabicyclo[2.2.2]octane in 40 ml of hot toluene. The reaction mixture was refluxed for 2 hours. After cooling the mixture was extracted with 2N HCl acid. The aqueous layer was basified with K2CO3 and extracted with CHCl3. The organic layer was dried over Na2SO4 and evaporated to dryness. The residue was purified by column chromatography (silica gel, CHCl3:MeOH:NH4OH, 95:5: 0.5). The yield was 1.5 g (48%); mp: 112-113° C.; CG/MS [M]$^-$: 347; $^1$H-NMR (CDCl3): δ 1.10-1.35 (m, 2H), 1.40-1.52 (m, 1H), 1.52-1.68 (m, 1H), 1.90 (m, 1H), 2.40-2.60 (m, 2H), 2.60-2.77 (m, 3H), 2.83-2.96 (m, 2H), 3.07-3.19 (m, 1H), 3.25-3.40 (m, 2H), 4.80 (m, 2H), 7.10-7.30 (m, 8H). 10,11-Dihydro-5[H]-dibenzo[a,d]cycloheptane-5-carboxylic acid was prepared as described in Kumazawa T. et al., J. Med. Chem., (1994), 37, 804-810.

EXAMPLE I-2b

Preparation of 5[H]-Dibenzo[a,d]cycloheptene-5-carboxylic acid 1-azabicyclo[2.2.2]oct-3-(R)-yl ester Prepared as in example I-2a. The yield was 3.12 g (71%); mp 129° C.; MS [M+1]$^+$: 346; $^1$H-NMR (DMSO-d6): δ 0.90-1.10 (m, 2H), 1.30-1.50 (m, 2H), 1.58 (m, 1H), 2.21-2.26 (m, 2H), 2.47-2.50 (m, 3H), 2.86-2.94 (m, 1H), 4.48-4.51 (m, 1H), 5.33 (s, 1H), 7.0 (m, 2H), 7.29-7.43 (m, 6H), 7.49-7.51 (m, 2H).

5[H]-Dibenzo[a,d]cycloheptene-5-carboxylic acid was prepared as described in M. A. Davis et al; J. Med. Chem., (1964), Vol 7, 88-94.

EXAMPLE I-2c

Preparation of 9,10-Dihydroanthracene-9-carboxylic acid 1-azabicyclo[2.2.2]oct-3-(R)-yl ester Prepared as in example I-2a. The yield was 0.77 g (62.6%); mp 139° C.; MS [M+1]$^+$: 334; $^1$H-NMR (DMSO-d6): δ 1.1-1.2 (m, 1H), 1.25-1.40 (m, 2H), 1.40-1.55 (m, 1H), 1.73 (m, 1H), 2.20 (m, 1H), 2.35-2.65 (m, 4H), 2.90-2.98 (m, 1H), 3.93-4.14 (dd, 2H, J=1.8 Hz, J=4.3 Hz), 4.56 (m, 1H), 5.14 (s, 1H), 7.25-7.35 (m, 4H), 7.35-7.50 (m, 4H). 9,10-Dihydro-anthracene-9-carboxylic acid was prepared as described in E. L. May and E. Mossettig; J. Am. Chem. Soc., (1948), Vol 70, 1077-9.
Method -e-

EXAMPLE I-3

Preparation of 2,2-Diphenylpropionic acid 1-azabicyclo [2.2.2]oct-3(R)-yl ester 1.1 g (4.8 mmol) of 2,2-diphenylpropionic acid were dissolved in 20 ml of THF. To this solution were added 0.87 g (5.3 mmol) of 1,1'-carbonyldiimidazole and the mixture was refluxed for an hour. The reaction was monitored by TLC following the formation of the imidazolide. When the reaction was completed part of the solvent was evaporated and 0.67 g (5.3 mmol) of 3-(R)-hydroxy-1-azabicyclo[2.2.2] octane were added. The reaction mixture was refluxed for 16 h, cooled, diluted with ether and washed with water. The organic layer was extracted with HCl 2N, the acid solution basified with K2CO3 and extracted with CHCl3. The organic solution was dried over Na2SO4 and evaporated to dryness to yield 1.21 g (75.2%) of an oil that was identified as the title ester.

0.64 g (1.9 mmol) of 2,2-Diphenylpropionic acid 1-azabicyclo [2.2.2]oct-3(R)-yl ester were dissolved in 6 ml of ketone and 0.085 g (0.95 mmol) of oxalic acid were added. After slow addition of ether a white solid was formed. The yield was 0.33 g (45.6%) of oxalate of 2,2-Diphenylpropionic acid 1-azabicyclo[2.2.2]oct-3(R)-yl ester; mp: 146° C.; MS [M free base+1]$^+$: 336.

Oxalate salt, $^1$H-NMR (CDCl3): δ 1.40-1.64 (m, 2H), 1.90 (s, 3H), 1.80-2.0 (m, 2H), 2.31 (m, 1H), 2.73-2.85 (m, 1H), 3.0-3.10 (m, 1H), 3.10-3.32 (m, 3H), 3.53-3.70 (m, 1H), 5.13 (m, 1H), 7.14-7.40 (m, 10H), 9.25 (broad band, 2H, H$^+$).
Method -f-

EXAMPLE I-4a

Preparation of 2-Hydroxy-2,2-dithien-2-ylacetic acid 1-azabloyclo[2.2.2]oct-4-yl ester A solution of 2-thienylmagnesium bromide was prepared from 220 mg (9 mmols) of Magnesium and 0.86 ml (9 mmols) of 2-bromothiophene in 15 ml of THF. This solution was added to 1.95 g (7 mmols) of oxothien-2-yl-acetic acid 1-azabicyclo[2.2.2]oct-4-yl ester (intermediate I-4b) dissolved in 20 ml of THF. The mixture was stirred at room temperature for 1 hour, refluxed for 1 hour, cooled, treated with a saturated solution of ammonium chloride and extracted with ether. After removal of the solvent the solid obtained was recrystallised from acetonitrile to yield 1.45 g, of a white solid (56%). $^1$H-NMR (DMSO-d6): δ 1.80-2.0

(m, 6H), 2.80-3.0 (m, 6H), 7.0 (m, 2H), 7.13 (m, 2H), 7.18 (s, 1H), 7.51 (m, 2H); MS [M+1]: 350; mp 174° C.

EXAMPLE I-4b

Preparation of oxothien-2-yl-acetic acid 1-azabicyclo [2.2.2]oct-4-yl ester

Oxalyl chloride (1.5 ml, 0.017 mol) was added to a solution of oxothien-2-yl-acetic acid (2.24 g, 0.014 mol) and dimethylformamide (one drop) in 30 ml of chloroform (etanol free) at 0° C. The mixture was stirred and allowed to warm at room temperature. After one hour the solvent was evaporated. The residue was dissolved in chloroform and evaporated again. This procedure was repeated two times. The product obtained was dissolved in CHCl3 (30 ml) and added to a suspension of 1.1 g (0.009 mols) of 4-hydroxy-1-azabicyclo[2.2.2]octane, 1.8 ml of triethylamine (0.013 mols), 0.6 g (0.9 mmols) of N-(methylpolystyrene)-4-(methylamino) pyridine at 70° C. The mixture was refluxed for 1 hour, cooled, filtered and washed with water. The title product was extracted with a solution of diluted HCl, washed with CHCl3, basified with K2CO3 and extracted again with CHCl3. After removal of the solvent 1.47 g (45%) of a solid was obtained. $^1$H-NMR (dmso): δ 2.0 (m, 6H), 2.9 (m, 6H), 7.35 (m, 1H), 8.05 (m, 1H), 8.3 (m, 1H).

EXAMPLE I-4c

Preparation of (Furan-2-yl)hydroxyphenylacetic acid 1-azabicyclo[2.2.2]oct-3(R)-yl ester Phenylmagnesium bromide, 0.0057 mol (5.7 ml of a solution 1M in THF), was added to a solution of 1.3 g (0.0052 mol) of oxofuran-2-ylacetic acid 1-azabicyclo [2.2.2]oct-3(R)-yl ester (intermediate I-4e-) dissolved in 15 ml of THF, at −70° C. in N2 atmosphere. The mixture was stirred at this temperature for 10 minutes, and then warmed to room temperature. After 1 hour, the reaction mixture was treated with a saturated solution of ammonium chloride and extracted three times with ethyl acetate. The organic phases were combined, washed with water and dried over Na2SO4. After removal of the solvent, the solid obtained was treated with ether and filtered to yield 0.67 g (40%) of a product whose structure was confirmed by $^1$H-NMR. This compound was also prepared as is described in Example I-1a (Method c). The diastereomers were separated by crystallization from acetonitrile and distinguished by $^1$H-NMR.

EXAMPLE I-4d

Preparation of 2-Hydroxy-2,2-difur-2-yl-acetic acid 1-azabicyclo [2.2.2]oct-3(R)-yl ester The title compound was synthesised as in example I-4c from intermediate I-4e- and 2-furanyl lithium which was prepared with furane and butyl lithium following a standard method. The yield was 380 mg (8%). $^1$H-NMR (CDCl3): δ 1.2-1.4 (m, 1H), 1.4-1.8 (m, 3H), 2.0 (m, 1H), 2.6-2.85 (m, 5H), 3.2 (m, 1H), 5.0 (m, 1H), 6.4 (m, 3H), 7.3 (m, 1H), 7.5 (m, 2H). MS [M+1]$^+$: 318.

EXAMPLE I-4e

Preparation of oxofuran-2-yl-acetic acid 1-azabicyclo [2.2.2]oct-3(R)-yl ester

Oxalyl chloride (9.75 ml, 0.112 mol) was added to a solution of oxofuran-2-ylacetic acid (10 g, 0.071 mol) and dimethylformamide (one drop) in 150 ml of chloroform (etanol free) at 0° C. The mixture was stirred and allowed to warm at room temperature. After five hours the solvent was evaporated. The residue was dissolved in chloroform and evaporated again. This procedure was repeated two times. The product obtained was dissolved in CHCl3 (150 ml) and a solution of 3(R)-quinuclidinol (10.90 g, 0.086 mol) in CHCl3 (150 ml) was added to this at 0° C. The mixture was stirred and allowed to warm at room temperature. After 15 h at r.t., the mixture was washed with 10% aqueous potassium carbonate, then with water, dried over Na2SO4 and evaporated to give 9.34 g (52.5%) of the title compound as a dark oil. Estructure confirmed by NMR.
$^1$H-NMR (CDCl3): δ 1.40-1.60 (m, 1H), 1.60-1.80 (m, 2H), 1.80-2.05 (m, 1H), 2.20 (m, 1H), 2.70-3.10 (m, 5H), 3.30-3.45 (m, 1H), 5.10 (m, 1H), 6.7 (m, 1H), 7.7 (m, 1H), 7.8 (m, 1H).

EXAMPLE I-4f

Preparation of 2-Hydroxy-2-phenyl-2-thien-2-ylacetic acid 1-azabicyclo[2.2.2]oct-3(R)-yl ester The title compound was prepared as described in example I-4c from intermediate I-4 g. The yield was 3 g (33%) as a mixture of diastereomers. After five crystallizations of 1.5 g of this mixture from boiling isopropanol, 0.200 g of a pure diastereomer (1) were obtained. The mother liquors from first crystallization were enriched with the other diastereomer (2). Diastereomer 1 was hidrolysed to yield (+)-2-Hydroxy-2-phenyl-2-thien-2-ylacetic acid as a pure enantiomer, $[\alpha]^{25}_D$=+25.4 (c=2, EtOH). This value was assigned to the R configuration provided that in literature (A. I. Meyers et. al. J. Org. Chem. (1980), 45(14), 2913) the 2(S) enantiomer has been described with $[\alpha]^{25}_D$=−20 (c=2, EtOH).

Diastereomer 1: 2(R)-2-Hydroxy-2-phenyl-2-thien-2-ylacetic acid 1-azabicyclo[2.2.2]oct-3(R)-yl ester $^1$H-NMR (DMSO-d6): δ 1.1-1.25 (m, 1H), 1.3-1.6 (m, 3H), 1.83 (m, 1H), 2.4-2.7 (m, 5H), 3.1 (m, 1H), 4.8 (m, 1H), 7.0 (m, 2H), 7.05 (m, 1H), 7.3-7.4 (m, 3H), 7.4-7.45 (m, 2H), 7.5 (m, 1H).

Diastereomer 2: 2(S)-2-Hydroxy-2-phenyl-2-thien-2-ylacetic acid 1-azabicyclo[2.2.2]oct-3(R)-yl ester $^1$H-NMR (DMSO-d6): δ 1.1-1.25 (m, 1H), 1.4-1.6 (m, 3H), 1.9 (m, 1H), 2.3-2.7 (m, 5H), 3.05 (m, 1H), 4.8 (m, 1H), 7.0 (m, 2H), 7.05 (m, 1H), 7.3-7.4 (m, 3H), 7.4-7.45 (m, 2H), 7.5 (m, 1H).

EXAMPLE I-4 g

Preparation of oxothien-2-yl-acetic acid 1-azabicyclo [2.2.2]oct-3(R)-yl ester

Oxalyl chloride (1.34 ml, 0.0154 mol) was added to a solution of oxothien-2-yl-acetic acid (2 g, 0.0128 mol) and dimethylformamide (one drop) in 30 ml of chloroform (etanol free) at 0° C. The mixture was stirred and allowed to warm at room temperature. After one hour the solvent was evaporated. The residue was dissolved in chloroform and evaporated again. This procedure was repeated two times. The product obtained was dissolved in CHCl3 (30 ml) and a solution of 3(R)-quinuclidinol (1.95 g, 0.0154 mol) in CHCl3 (30 ml) was added to this at 0° C. The mixture was stirred and allowed to warm at room temperature. After 1.5 h at r.t., the mixture was washed with 10% aqueous potassium carbonate, then with water, dried over Na2SO4 and evaporated to give 3.14 g (92.6%) of the title compound as a yellow oil. $^1$H-NMR (CDCl3): δ 1.40-1.50 (m, 1H), 1.50-1.70 (m, 1H), 1.70-1.80 (m, 1H), 1.90-2.0 (m, 1H), 2.15 (m, 1H), 2.70-3.05 (m, 5H), 3.30-3.40 (m, 1H), 5.05 (m, 1H), 7.20 (m, 1H), 7.85 (m, 1H), 8.10 (m, 1H).

Other carboxylic acids of Formula B—C(O)OH, whose preparation (or the syntheses of their derivatives methyl ester, chloride or imidazolide) haven't been described in methods c, d, e or in the Examples I-1e, I-1f and I-1g, and that are not commercially available, could be prepared as is described in the following references:

FR 2012964
M. A. Davis et al; J. Med. Chem. (1963), 6, 513-516.
T. Kumazawa et al; J. Med. Chem, (1994), 37(6), 804-810.
M. A. Davis et al; J. Med. Chem., (1964), Vol (7), 88-94.
Sestanj, K; Can. J. Chem., (1971), 49, 664-665.
Burtner, R.; J. Am. Chem. Soc., (1943), 65, 1582-1585
Heacock R. A. et al; Ann. Appl. Biol., (1958), 46(3), 352-365.
Rigaudy J. et. al; Bull. Soc. Chim. France, (1959), 638-43.
Ueda I. et al; Bull. Chem. Soc. Jpn; (1975), 48 (8), 2306-2309.
E. L. May et. al.; J. Am. Chem. Soc., (1948), 70, 1077-9.

Also included within the scope of the present invention are pharmaceutical composition which comprise, as the active ingredient, at least one quinuclidine derivative of general formula (I) in association with a pharmaceutically acceptable carrier or diluent. Preferably the composition is made up in a form suitable for oral administration.

The pharmaceutically acceptable carrier or diluents which are mixed with the active compound or compounds, to form the composition of this invention are well-known per se and the actual excipients used depend inter alia on the intended method of administration of the composition.

Compositions of this invention are preferably adapted for oral administration. In this case, the composition for oral administration may take the form of tablets, film-coated tablets, liquid inhalant, powder inhalant and inhalation aerosol; all containing one or more compounds of the invention; such preparations may be made by methods well-known in the art.

The diluents which may be used in the preparations of the compositions include those liquid and solid diluents which are compatible with the active ingredient, together with colouring or flavouring agents, if desired. Tablets or film-coated tablets may conveniently contain between 500 and 1 mg, preferably from 5 to 300 mg of active ingredient. The inhalant compositions may contain between 1 μg and 1,000 μg, preferably from 10 to 800 μg of active ingredient. In human therapy, the dose of the compound of general formula (I) depend on the desired effect and duration of treatment; adult doses are generally between 3 mg and 300 mg per day as tablets and 10 μg and 800 μg per day as inhalant composition.

Pharmacological Action

The following examples demonstrate the excellent pharmacological activities of the compounds of the present invention. The results on human muscarinic receptors binding and in the test on bronchospasm in guinea pig, were obtained as described below.

Human Muscarinic Receptor Studies.

The binding of [$^3$H]-NMS to human muscarinic receptors was performed according to Waelbroek et al (1990) (1). Assays were carried out at 25° C. Membrane preparations from stably transfected chinese hamster ovary-K1 cells (CHO) expressing the genes for the human muscarinic receptors Hm3 were used.

For determination of $IC_{50}$, membrane preparations were suspended in DPBS to a final concentration of 89 μg/ml for the Hm3 subtype. The membrane suspension was incubated with the tritiated compound for 60 min. After incubation the membrane fraction was separated by filtration and the bound radioactivity determined. Non specific binding was determined by addition of $10^{-4}$ M atropine. At least six concentrations were assayed in duplicate to generate individual displacement curves.

| COMPOUNDS No | BINDING TO RECEPTOR $M_3$ ($IC_{50}$ nM) |
| --- | --- |
| ATROPINE | 3.2 |
| IPRATROPIUM | 3.0 |
| 1 | 31 |
| 2 | 15 |
| 7 | 22 |
| 8 | 4.8 |
| 17 | 14 |
| 18 | 6.6 |
| 20 | 6.8 |
| 35 | 13 |
| 36 | 2.7 |
| 39 | 3.8 |
| 44 | 4.4 |
| 53 | 5.6 |
| 71 | 8.2 |
| 74 | 16 |
| 77 | 3.1 |
| 78 | 5 |
| 84 | 9.9 |
| 89 | 5.4 |
| 99 | 31 |
| 100 | 14 |
| 101 | 7.6 |
| 109 | 31 |
| 114 | 14 |
| 116 | 23 |
| 126 | 13 |
| 127 | 16 |
| 128 | 8.8 |
| 129 | 6.3 |
| 136 | 11 |
| 137 | 6.9 |
| 138 | 19 |
| 146 | 13 |

(1) M. Waelbroek, M. Tastenoy, J. Camus, J Christophe. Binding of selective antagonists to four muscarinic receptors (M1 to M4) in rat forebrain. Mol. Pharmacol. (1990) 38: 267-273.

Our results show that the compounds of the present invention have affinities for the $M_3$ receptors which are very similar to the reference compounds.

The compounds of the invention preferably have high affinities for muscarinic $M_3$ receptors (HM3), preferably human muscarinic receptors. Affinity levels can typically be measured by in vitro assays, for example, as described above.

Preferred compounds of the invention have an $IC_{50}$ (nM) value for $M_3$ receptors of less than 35, preferably less than 25, 20 or 15, more preferably less than 10.8 or 5.

Test on Bronchospasm in Guinea Pig

The studies were performed according to Konzett and Rossler (2). Aqueous solutions of the agents to be tested were nebulized and inhaled by anaesthetized ventilated male guinea pigs (Dunkin-Hartley). The bronchial response to intravenous acetylcholine challenge was determined before and after drug administration and the percent change in pulmonary resistance at several time-points.

2. Konzett H., Rossler F. Versuchsanordnung zu Untersuchungen ander bronchialmuskulatur. Arch. Exp. Path. Pharmacol. 195: 71-74 (1940)

The compounds of the present invention inhibited the bronchospasm response to acetylcholine with high potency and a long duration of action.

From the above described results one of ordinary skill in the art can readily understand that the compounds of the present invention have excellent antimuscarinic activity ($M_3$) and thus are useful for the treatment of diseases in which the muscarinic $M_3$ receptor is implicated, including respiratory diseases such as chronic obstructive pulmonary disease, chronic bronchitis, asthma and rhinitis, urinary diseases such as urinary incontinence and pollakinuria in neuripenia pollakinuria, neurogenic bladder, nocturnal enuresis, unstable bladder, cystospasm and chronic cystitis and gastrointestinal diseases such as irritable bowel syndrome, spastic colitis and diverticulitis.

The present invention further provides a compound of formula (I) or a pharmaceutically acceptable composition comprising a compound of formula (I) for use in a method of treatment of the human or animal body by therapy, in particular for the treatment of respiratory, urinary or gastrointestinal disease.

The present invention further provides the use of a compound of formula (I) or a pharmaceutically acceptable composition comprising a compound of formula (I) for the manufacture of a medicament for the treatment of respiratory, urinary or gastrointestinal disease.

Further, the compounds of formula (I) and pharmaceutical compositions comprising a compound of formula (I) can be used in a method of treating respiratory, urinary or gastrointestinal disease, which method comprises administering to a human or animal patient in need of such treatment an effective amount of a compound of formula (I) or a pharmaceutical composition comprising a compound of formula (I).

The present invention will be further illustrated by the following examples. The examples are given by way of illustration only and are not to be construed as limiting.

EXAMPLE 1

3(R)-Diphenylacetoxy-1-(3-phenoxypropyl)-1-azoniabicyclo[2.2.2]octane; bromide

The title compound was synthesised according to methods d and a. The yield of final step was 500 mg, 81%. $^1$H-NMR (CDCl$_3$): δ 1.72-2.18 (m, 6H), 2.35 (m, 1H), 3.0 (m, 1H), 3.23 (m, 1H), 3.59-3.88 (m, 5H), 4.0 (m, 2H), 4.30 (m, 1H), 5.1 (s, 1H), 5.25 (m, 1H), 6.8-6.9 (m, 2H), 6.9-7.0 (m, 1H), 7.2-7.4 (m, 12H); MS [M-Br]$^+$: 456; mp 129° C.

EXAMPLE 2

3(R)-(2-Hydroxy-2,2-diphenylacetoxy)-1-(3-phenoxypropyl)-1-azonlabicyclo[2.2.2]octane; bromide The title compound was synthesised according to methods c and a. The yield of final step was 280 mg, 42%. $^1$H-NMR (DMSO-d6): δ 1.5-1.7 (m, 2H), 1.9-2.1 (m, 4H), 2.3 (m, 1H), 3.1 (m, 1H), 3.2-3.5 (m, 6H), 3.9-4.1 (m, 3H), 5.25 (m, 1H), 6.8 (bs, OH), 6.95 (m, 3H), 7.2-7.5 (m, 12H); MS [M-Br]$^+$: 472; mp 199° C.

EXAMPLE 3

3(R)-[2,2-Bis(4-fluorophenyl)-2-hydroxyacetoxy]-1-(3-phenoxypropyl)-1-azoniabicyclo[2.2.2]octane; bromide The title compound was synthesised according to methods c and a. The yield of final step was 400 mg, 85%. $^1$H-NMR (DMSO-d6): δ 1.5-1.65 (m, 1H), 1.7-1.8 (m, 1H), 1.85-2.0 (m, 2H), 2.05-2.2 (m, 2H), 2.3 (m, 1H), 3.1-3.2 (m, 1H), 3.3-3.5 (m, 6H), 3.95 (m, 1H), 4.05 (m, 2H), 5.25 (m, 1H), 6.9-7.0 (m, 4H), 7.1-7.5 (m, 10H); MS [M-Br]$^+$: 508; mp 253° C.

EXAMPLE 4

3(R)-[2,2-Bis(4-fluorophenyl)-2-hydroxyacetoxy]-1-phenethyl-1-azoniabicyclo[2.2.2]octane; bromide The title compound was synthesised according to methods c and a. The yield of final step was 300 mg, 67%. $^1$H-NMR (DMSO-d6): δ 1.5-1.65 (m, 1H), 1.7-1.85 (m, 1H), 1.85-2.1 (m, 2H), 2.3 (m, 1H), 2.9-3.1 (m, 2H), 3.15-3.25 (m, 1H), 3.3-3.6 (m, 6H), 3.95-4.05 (m, 1H), 5.25 (m, 1H), 6.95 (s, OH), 7.1-7.5 (m, 13H); MS [M-Br]$^{30}$ : 478; mp 182° C.

EXAMPLE 5

3(R)-(2-Hydroxy-2,2-di-p-tolylacetoxy)-1-(3-phenoxypropyl)-1-azoniabicyclo[2.2.2]octane; bromide The title compound was synthesised according to methods c and a. The yield of final step was 500 mg, 54%. $^1$H-NMR (DMSO-d6): δ 1.55-1.8 (m, 2H), 1.85-2.0 (m, 2H), 2.05-1.15 (m, 2H), 2.3 (s, 7H), 3.05-3.15 (m, 1H), 3.25-3.5 (m, 6H), 3.95 (m, 1H), 4.05 (t, 2H), 5.2 (m, 1H), 6.8 (s, OH), 6.95 (m, 3H), 7.1-7.2 (m, 4H), 7.2-7.35 (m, 6H); MS [M−Br]$^+$:500; mp 183° C.

EXAMPLE 6

3(R)-(2-Hydroxy-2,2-di-p-tolylacetoxy)-1-phenethyl-1-azoniabicyclo[2.2.2]octane; bromide The title compound was synthesised according to methods c and a. The yield of final step was 650 mg, 74%. $^1$H-NMR (DMSO-d6): δ 1.55-1.8 (m, 2H), 1.85-2.05 (m, 2H), 2.25 (s, 7H), 2.9-3.05 (m, 2H), 3.1-3.25 (m, 1H), 3.3-3.55 (m, 6H), 3.95 (m, 1H), 5.25 (m, 1H), 6.8 (s, OH), 7.1-7.2 (m, 4H), 7.2-7.35 (m, 9H); MS [M-Br]$^+$:470; mp 144° C.

EXAMPLE 7

3(R)-(2,2-Diphenylpropionyloxy)-1-(3-phenoxypropyl)-1-azoniabicyclo[2.2.2]octane; bromide The title compound was synthesised according to methods e and a. The yield of final step was 250 mg, 61%. $^1$H-NMR (CDCl$_3$): δ 1.47-1.60 (m, 1H), 1.8-2.0 (m, 1H), 2.0 (s, 3H), 2.0-2.15 (m, 4H), 2.39 (s, 1H), 2.6 (m, 1H), 2.92 (d, 1H), 3.6 (m, 1H), 3.7-3.9 (m, 4H), 4.0 (m, 2H), 4.3 (m, 1H), 5.25 (m, 1H), 6.85 (m, 2H), 7.0 (m, 1H), 7.3 (m, 12H); MS [M−Br]$^{30}$ : 470; mp 186° C.

EXAMPLE 8

3(R)-(2-Hydroxy-2-phenyl-2-thien-2-ylacetoxy)-1-(3-phenoxypropyl)-1-azonlabicyclo[2.2.2]octane; bromide The title compound was synthesised as a mixture of diastereomers according to methods c and a. The yield of final step was 520 mg, 62%. $^1$H-NMR (DMSO-d6): δ 1.5-1.95 (m, 4H), 2.1 (m, 2H), 2.3 (m, 1H), 3.1 (m, 1H), 3.3-3.5 (m, 6H), 3.9 (m, 1H), 4.05 (t, 2H), 5.2 (m, 1H), 7.0 (m, 4H), 7.15 (m, 2H), 7.35 (m, 5H), 7.5 (m, 3H); MS [M-Br]$^{30}$: 478; mp 220° C.

EXAMPLE 9

3(R)-[2(R)-(2-Hydroxy-2-phenyl-2-thien-2-ylacetoxy)]-1-(3-phenoxypropyl)-1-azoniabicyclo[2.2.2]octane; trifluoroacetate The title compound was synthesised according to methods f and b from intermediate I-4f, diastereomer 1. The yield of final step was 10 mg, 23%. $^1$H-NMR (DMSO-d6): δ 1.5-1.6 (m, 1H), 1.65-1.75 (m, 1H), 1.8-2.0 (m, 2H), 2.05-2.1 (m, 2H), 2.3 (m, 1H), 3.05-3.2 (m, 1H), 3.25-3.55 (m, 6H), 3.85-3.95 (m, 1H), 4.0 (t, 2H), 5.2 (m, 1H), 6.95 (m, 3H), 7.03 (m, 1H), 7.15 (dd, 1H), 7.2 (s, OH), 7.3-7.5 (m, 5H), 7.45-7.55 (m, 3H); MS [M-CF3COO]$^+$: 478.

EXAMPLE 10

3(R)-[2(S)-(2-Hydroxy-2-phenyl-2-thien-2-ylacetoxy)]-1-(3-phenoxypropyl)-1-azoniabicyclo[2.2.2]octane; trifluoroacetate The title compound was synthesised according to methods f and b from intermediate I-4f, diastereomer 2. The yield of final step was 3 mg, 11%. $^1$H-NMR (DMSO-d6): δ 1.6-1.75 (m, 2H), 1.8-2.0 (m, 4H), 2.25 (m, 1H), 2.8 (t, 2H), 2.95-3.1 (m, 1H), 3.15-3.5 (m, 6H), 3.8-3.95 (m, 1H), 5.2 (m, 1H), 6.92 (m, 1H), 6.96-7.03 (m, 2H), 7.1 (dd, 1H), 7.18 (s, OH), 7.3-7.4 (m, 4H), 7.43-7.5 (m, 2H), 7.51 (dd, 1H); MS [M-CF3COO]$^+$: 478.

EXAMPLE 11

3(R)-[2(R)-(2-Hydroxy-2-phenyl-2-thien-2-ylacetoxy)]-1-(3-phenylpropyl)-1-azoniabicyclo[2.2.2]octane; trifluoroacetate The title compound was synthesised according to methods f and b from intermediate I-4f, diastereomer 1. The yield of final step was 9 mg, 22%. $^1$H-NMR (DMSO-d6): δ 1.45-1.55 (m, 1H), 1.65-1.75 (m, 1H), 1.85-2.05 (m, 2H), 2.3 (m, 1H), 2.9-3.1 (m, 2H), 3.1-3.25 (m, 1H), 3.25-3.55 (m, 6H), 3.9-4.0 (m, 1H), 5.25 (m, 1H), 7.05 (m, 1H), 7.15 (m, 1H), 7.2 (m, 1H), 7.25-7.4 (m, 8H), 7.45 (m, 2H, 7.55 (m, 1H); MS [M-CF3COO]$^+$: 448.

EXAMPLE 12

3(R)-[2(R)-(2-Hydroxy-2-phenyl-2-thien-2-ylacetoxy)]-1-(3-phenylpropyl)-1-azoniabicyclo[2.2.2]octane; trifluoroacetate The title compound was synthesised according to methods f and b from intermediate I-4f. The yield of final step was 11 mg, 26%. $^1$H-NMR (DMSO-d6): δ 1.45-1.55 (m, 1H), 1.6-1.75 (m, 1H), 1.8-2.0 (m, 4H), 2.25 (m, 1H), 2.55 (t, 2H), 3.0-3.1 (m, 1H), 3.15-3.55 (m, 6H), 3.8-3.9 (m, 1H), 5.2 (m, 1H), 7.0 (m, 1H), 7.1 (m, 1H), 7.15-7.4 (m, 9H), 7.45 (m, 2H), 7.5 (m, 1H); MS [M-CF3COO]$^+$: 462.

EXAMPLE 13

3(R)-[2(R)-(2-Hydroxy-2-phenyl-2-thien-2-ylacetoxy)]-1-(2-thien-2-yl ethyl)-1-azoniabicyclo[2.2.2]octane; trifluoroacetate The title compound was synthesised according to methods f and b from intermediate I-4f, diastereomer 1. The yield of final step was 10 mg, 24%. $^1$H-NMR (DMSO-d6): δ 1.45-1.55 (m, 1H), 1.65-1.75 (m, 1H), 1.8-2.0 (m, 2H), 2.3 (m, 1H), 3.1-3.6 (m, 9H), 3.9-4.0 (m, 1H), 5.25 (m, 1H), 7.0 (m, 3H), 7.15 (dd, 1H), 7.2 (s, OH), 7.3-7.4 (m, 3H), 7.45-7.55 (m, 4H); MS [M-CF3COO]$^+$: 454.

EXAMPLE 14

3(R)-[2(R)-(2-Hydroxy-2-phenyl-2-thien-2-ylacetoxy)]-1-(3-thien-2-yl propyl)-1-azoniabicyclo[2.2.2]octane; trifluoroacetate The title compound was synthesised according to methods f and b from intermediate I-4f, diastereomer 1. The yield of final step was 8 mg, 19%. $^1$H-NMR (DMSO-d6): δ 1.45-1.6 (m, 1H), 1.65-1.75 (m, 1H), 1.8-2.05 (m, 4H), 2.25 (m, 1H), 2.8 (t, 2H), 3.0-3.15 (m, 1H), 3.2-3.5 (m, 6H), 3.8-3.95 (m, 1H), 5.2 (m, 1H), 6.92 (m, 1H), 6.96-7.03 (m, 2H), 7.13 (dd, 1H), 7.2 (s, OH), 7.3-7.4 (m, 4H), 7.45-7.5 (m, 2H), 7.52 (dd, 1H); MS [M-CF3COO]$^+$: 468.

EXAMPLE 15

3(R)-[2(S)-(2-Hydroxy-2-phenyl-2-thien-2-ylacetoxy)]-1-(3-thien-2-yl propyl)-1-azoniabicyclo[2.2.2]octane; trifluoroacetate The title compound was synthesised according to methods f and b from intermediate I-4f, diastereomer 2. The yield of final step was 7 mg, 26%. $^1$H-NMR (DMSO-d6): δ 1.6-1.75 (m, 2H), 1.8-2.0 (m, 4H), 2.25 (m, 1H), 2.8 (t, 2H), 2.95-3.1 (m, 1H), 3.15-3.5 (m, 6H), 3.8-3.95 (m, 1H), 5.2 (m, 1H), 6.92 (m, 1H), 6.96-7.03 (m, 2H), 7.1 (dd, 1H), 7.18 (s, OH), 7.3-7.4 (m, 4H), 7.43-7.5 (m, 2H), 7.51 (dd, 1H); MS [M-CF3COO]$^+$: 468.

EXAMPLE 16

3(R)-[2(R)-(2-Hydroxy-2-phenyl-2-thien-2-ylacetoxy)]-1-(2-phenoxyethyl)-1-azonlabicyclo[2.2.2]octane; trifluoroacetate The title compound was synthesised according to methods f and b from intermediate I-4f, diastereomer 1. The yield of final step was 11 mg, 26%. $^1$H-NMR (DMSO-d6): δ 1.5-1.6 (m, 1H), 1.65-1.75 (m, 1H), 1.8-2.0 (m, 2H), 2.25 (m, 1H), 3.15-3.6 (m, 5H), 3.7 (m, 2H), 4.0 (m, 2H), 4.4 (m, 2H), 5.25

(m, 1H), 6.95-7.03 (m, 4H), 7.12 (dd, 1H), 7.2 (s, OH), 7.3-7.4 (m, 5H), 7.4-7.5 (m, 3H); MS [M-CF3COO]+: 464.

EXAMPLE 17

3(R)-(2-Furan-2-yl-2-hydroxy-2-phenylacetoxy)-1-(3-phenylallyl)-1-azoniabicyclo[2.2.2]octane; bromide The title compound was synthesised as a mixture of diastereomers according to methods c and a. The yield of final step was 240 mg, 77%. $^1$H-NMR (DMSO-d6): δ 1.55-2.0 (m, 4H), 2.27 (m, 1H), 3.05-3.55 (m, 5H), 3.88-3.98 (m, 1H), 4.0-4.10 (m, 2H), 5.21 (m, 1H), 6.23-6.31 (doble dd, 1H), 6.36-6.48 (m, 2H), 6.83-6.90 (dd, 1H), 6.95 (d, OH), 7.26-7.66 (m, 11H); MS [M-Br]+: 444; mp 99° C.

EXAMPLE 18

3(R)-(2-Furan-2-yl-2-hydroxy-2-phenylacetoxy)-1-(2-phenoxyethyl)-1-azoniabicyclo[2.2.2] octane; bromide The title compound was synthesised as a mixture of diastereomers according to methods c and a. The yield of final step was 210 mg, 66%. $^1$H-NMR (DMSO-d6): δ 1.50-2.05 (m, 4H), 2.27 (m, 1H), 3.20 (m, 1H), 3.37-3.65 (m, 4H), 3.65-3.75 (m, 2H), 4.04 (m, 1H), 4.40 (m, 2H), 5.21 (m, 1H), 6.23-6.32 (doble dd, 1H), 6.44 (m, 1H), 6.94-7.04 (m, 4H), 7.33-7.50 (m, 7H), 7.64 (m, 1H); MS [M-Br]+: 448; mp 163° C.

EXAMPLE 19

3(R)-[2(*)-(2-Furan-2-yl-2-hydroxy-2-phenylacetoxy)]-1-(2-phenoxyethyl)-1-azoniabicyclo[2.2.2]octane; trifluoroacetate The title compound was synthesised according to methods c and b from intermediate I-1a, diastereomer 1. The yield of final step was 11 mg, 23%. $^1$H-NMR (DMSO-d6): δ 1.65-1.80 (m, 2H), 1.80-2.10 (m, 2H), 2.27 (m, 1H), 3.15-3.65 (m, 5H), 3.68 (m, 2H), 4.0 (m, 1H), 4.40 (t, 2H), 5.20 (m, 1H), 6.23 (d, 1H), 6.42 (m, 1H), 6.92-7.04 (m, 4H), 7.30-7.38 (m, 5H), 7.44-7.50 (m, 2H), 7.64 (m, 1H); MS [M-CF3COO]+: 448.

EXAMPLE 20

3(R)-(2-Furan-2-yl-2-hydroxy-2-phenylacetoxy)-1-(3-phenoxypropyl)-1-azoniabicyclo[2.2.2] octane; bromide The title compound has been described in method -a-.

EXAMPLE 21

3(R)-[2(*)-(2-Furan-2-yl-2-hydroxy-2-phenylacetoxy)]-1-(3-phenoxy propyl)-1-azoniabicyclo[2.2.2] octane; bromide The title compound was synthesised according to methods c and a from intermediate I-1a, diastereomer 1. The yield of final step was 1.15 g 99%. $^1$H-NMR (DMSO-d6): δ 1.60-2.20 (m, 6H), 2.25 (m, 1H), 3.10 (m, 1H), 3.20-3.60 (m, 6H), 3.95 (m, 1H), 4.05 (m, 2H), 5.20 (m, 1H), 6.25 (dd, 1H), 6.45 (m, 1H), 6.95 (m, 4H), 7.30-7.50 (m, 7H), 7.70 (m, 1H); MS [M-Br]+: 462; mp 156° C.

EXAMPLE 22

3(R)-[2(*)-(2-Furan-2-yl-2-hydroxy-2-phenylacetoxy)]-1-(3-phenoxy propyl)-1-azonlabicyclo[2.2.2] octane; trifluoroacetate The title compound was synthesised according to methods c and b from intermediate I-1a, diastereomer 2. The yield of final step was 10 mg, 20%. $^1$H-NMR (DMSO-d6): δ 1.50-2.20 (m, 6H), 2.25 (m, 1H), 3.10 (m, 1H), 3.20-3.60 (m, 6H), 3.95 (m, 1H), 4.05 (m, 2H), 5.20 (m, 1H), 6.35 (dd, 1H), 6.45 (m, 1H), 6.95 (m, 4H), 7.30-7.50 (m, 7H), 7.70 (m, 1H); MS [M-CF3COO]+: 462.

EXAMPLE 23

3(R)-(2-Furan-2-yl-2-hydroxy-2-phenylacetoxy)-1-phenethyl-1-azoniabicyclo[2.2.2]octane; trifluoroacetate The title compound was synthesised as a mixture of diastereomers according to methods c and b. The yield of final step was 12 mg, 13%. $^1$H-NMR (DMSO-d6): δ 1.5 (m, 1H), 1.7 (m, 1H), 1.9-2.05 (m, 2H), 2.3 (m, 1H), 2.95 (m, 2H), 3.15 (m, 1H), 3.25-3.55 (m, 6H), 3.95 (m, 1H), 5.25 (m, 1H), 6.3 (d, 1H), 6.45 (m, 1H), 6.95 (d, 1H), 7.25-7.45 (m, 8H), 7.5 (m, 2H), 7.7 (m, 1H); MS [M-CF$_3$COO]+: 432.

EXAMPLE 24

3(R)-[2(*)-(2-Furan-2-yl-2-hydroxy-2-phenylacetoxy)]-1-phenethyl-1-azoniabicyclo[2.2.2]octane; trifluoroacetate The title compound was synthesised according to methods c and b from intermediate I-1a, diastereomer 1. The yield of final step was 16 mg, 40%. $^1$H-NMR (DMSO-d6): δ 1.65-1.80 (m, 2H), 1.90-2.05 (m, 2H), 2.3 (m, 1H), 2.95 (m, 2H), 3.15 (m, 1H), 3.25-3.55 (m, 6H), 3.95 (m, 1H), 5.25 (m, 1H), 6.26 (dd, 1H), 6.46 (m, 1H), 6.95 (s, 1H, OH), 7.25-7.45 (m, 8H), 7.5 (m, 2H), 7.7 (m, 1H); MS [M-CF3COO]+: 432.

EXAMPLE 25

3(R)-[2(*)-(2-Furan-2-yl-2-hydroxy-2-phenylacetoxy)]-1-phenethyl-1-azoniabicyclo[2.2.2]octane; trifluoroacetate The title compound was synthesised according to methods c and b from intermediate I-1a, diastereomer 2. The yield of final step was 14 mg, 35%. $^1$H-NMR (DMSO-d6): δ 1.50-1.80 (m, 2H), 1.90-2.05 (m, 2H), 2.3 (m, 1H), 2.95 (m, 2H), 3.15 (m, 1H), 3.25-3.55 (m, 6H), 3.95 (m, 1H), 5.25 (m, 1H), 6.32 (dd, 1H), 6.46 (m, 1H), 6.95 (s, 1H, OH), 7.25-7.45 (m, 8H), 7.5 (m, 2H), 7.7 (m, 1H); MS [M-CF3COO]+: 432.

EXAMPLE 26

3(R)-[2(*)-(2-Furan-2-yl-2-hydroxy-2-phenylacetoxy)]-1-(3-phenylpropyl)-1-azoniabicyclo[2.2.2] octane; trifluoroacetate The title compound was synthesised according to methods c and b from intermediate I-1a, diastereomer 1. The yield of final step was 10 mg, 21%. $^1$H-NMR (DMSO-d6): δ 1.60-1.75 (m, 2H), 1.80-2.0 (m, 4H), 2.25 (m, 1H), 2.50-2.60 (m, 2H), 3.0 (m, 1H), 3.10-3.50 (m, 6H), 3.83 (m, 1H), 5.17 (m, 1H), 6.25 (d, 1H), 6.45 (m, 1H), 6.95 (s, 1H), 7.20-7.40 (m, 8H), 7.46-7.48 (m, 2H), 7.66 (m, 1H); MS [M-CF3COO]$^+$: 446.

EXAMPLE 27

3(R)-[2(*)-(2-Furan-2-yl-2-hydroxy-2-phenylacetoxy)]-1-(2-thien-2-yl ethyl)-1-azoniabicyclo[2.2.2]octane; trifluoroacetate The title compound was synthesised according to methods c and b from intermediate I-1a, diastereomer 1. The yield of final step was 9 mg, 19%. $^1$H-NMR (DMSO-d6): δ 1.65-1.80 (m, 2H), 1.85-2.05 (m, 2H), 2.30 (m, 1H), 3.10-3.40 (m, 3H), 3.40-3.60 (m, 6H), 3.95 (m, 1H), 5.24 (m, 1H), 6.27 (d, 1H), 6.47 (m, 1H), 6.96 (s, 1H), 7.0-7.04 (m 2H), 7.36-7.48 (m, 4H), 7.49-7.54 (m, 2H), 7.70 (m, 1H); MS [M-CF3COO]$^+$: 438.

EXAMPLE 28

3(R)-[2(*)-(2-Furan-2-yl-2-hydroxy-2-phenylacetoxy)]-1-(3-thien-2-yl propyl)-1-azoniabicyclo[2.2.2]octane; trifluoroacetate The title compound was synthesised according to methods c and b from intermediate I-1a, diastereomer 1. The yield of final step was 9 mg, 19%. $^1$H-NMR (DMSO-d6): δ 1.60-1.75 (m, 2H), 1.80-2.05 (m, 4H), 2.26 (m, 1H), 2.81 (t, 2H), 3.02 (m, 1H), 3.10-3.45 (m, 6H), 3.85 (m, 1H), 5.18 (m, 1H), 6.25 (d, 1H), 6.45 (m, 1H), 6.90-7.0 (m, 3H), 7.32-7.42 (M, 4H), 7.45-7.51 (m, 2H), 7.66 (m, 1H); MS [M-CF3COO]$^+$: 452.

EXAMPLE 29

3(R)-(2-Furan-2-yl-2-hydroxy-2-thien-2-ylacetoxy)-1-phenethyl-1-azoniabicyclo[2.2.2]octane; trifluoroacetate The title compound was synthesised as a mixture of diastereomers according to methods c and b. The yield of final step was 18 mg, 20%. $^1$H-NMR (DMSO-d6): δ 1.65-2.05 (m, 4H), 2.3 (m, 1H), 3.0 (m, 2H), 3.15-3.6 (m, 7H), 3.95 (m, 1H), 5.25 (m, 1H), 6.35 (dd, 1H), 6.45 (m, 1H), 7.05 (m, 1H), 7.2 (dd, 1H), 7.25-7.5 (m, 6H), 7.55 (m, 1H), 7.65 (m, 1H); MS [M-CF$_3$COO]$^+$: 438.

EXAMPLE 30

3(R)-(2-Furan-2-yl-2-hydroxy-2-thien-2-ylacetoxy)-1-(2-phenoxyethyl)-1-azonlabicyclo[2.2.2]octane; trifluoroacetate The title compound was synthesised as a mixture of diastereomers according to methods c and b. The yield of final step was 22 mg, 23%. $^1$H-NMR (DMSO-d6): δ 2.65-2.05 (m, 4H), 2.3 (m, 1H), 3.15-3.65 (m, 7H), 4.05 (m, 1H), 4.4 (m, 2H), 5.15 (m, 1H), 6.35 (dd, 1H), 6.45 (m, 1H), 6.95-7.05 (m, 4H), 7.15 (d, 1H), 7.3-7.4 (m, 3H), 7.5 (dd, 1H), 7.65 (d, 1H); MS [M-CF$_3$COO]$^+$: 454.

EXAMPLE 31

3(R)-(2-Furan-2-yl-2-hydroxy-2-thien-2-ylacetoxy)-1-(4-oxo-4-phenylbutyl)-1-azonlabicyclo[2.2.2]octane; trifluoroacetate The title compound was synthesised as a mixture of diastereomers according to methods c and b. The yield of final step was 15.4 mg, 15%. $^1$H-NMR (DMSO-d6): δ 1.65-2.1 (m, 6H), 7.05-7.55 (m, 9H), 3.95 (m, 1H), 5.1 (m, 1H), 6.35 (dd, 1H), 6.5 (m, 1H), 7.05 (m, 1H), 7.15 (m, 1H), 7.3 (d, 1H), 7.55 (m, 3H), 7.7 (dd, 2H), 8.0 (d, 2H); MS [M-CF$_3$COO]$^+$: 480.

EXAMPLE 32

1-(3-phenoxypropyl)-3(R)-(2-Furan-2-yl-2-hydroxy-2-thien-2-yl-acetoxy)-1-azonlabicyclo[2.2.2]octane; bromide The title compound was synthesised as a mixture of diastereomers according to methods c and a. The yield of final step was 100 mg, 41%. $^1$H-NMR (DMSO-d6): δ 1.65-2.05 (m, 4H), 2.1-2.0 (m, 2H), 2.3 (m, 1H), 3.15 (m, 1H), 3.25-3.6 (6H), 3.9-4.1 (m, 3H), 5.1 (m, 1H), 6.35 (d, 1H), 6.45 (s, 1H), 6.95 (m, 3H), 7.05 (m, 1H), 7.2 (d, 1H), 7.3 (m, 3H), 7.55 (d, 1H), 7.7 (s, 1H); MS [M-Br]$^{30}$: 520; mp 173° C.

EXAMPLE 33

1-(3-phenoxypropyl)-3(R)-(2,2-difuran-2-yl-2-hydroxyacetoxy)-1-azonlabicyclo[2.2.2]octane; bromide The title compound was synthesised according to methods f and a. The yield of final step was 200 mg, 60%. $^1$H-NMR (DMSO-d6): δ 1.6-2.20 (m, 6H), 2.3 (m, 1H), 2.95-3.65 (m, 7H), 3.80-4.10 (m, 3H), 5.2 (m, 1H), 6.3-6.6 (m, 4H), 6.8-7.0 (m, 3H), 7.1 (s, OH), 7.3 (m, 2H), 7.7 (m, 2H); MS [M-Br]$^{30}$: 452.

EXAMPLE 34

3(R)-(2,2-Dithien-2-ylacetoxy)-1-(2-phenoxyethyl)-1-azoniabicyclo [2.2.2]octane; bromide The title compound was synthesised according to methods c and a. The yield of final step was 240 mg, 60%. $^1$H-NMR (DMSO-d6): δ 1.85-2.10 (m, 4H), 2.30 (s, 1H), 3.40 (m, 1H), 3.44-3.80 (m, 6H), 4.10 (m, 1H), 4.45 (m, 2H), 5.20 (m, 1H), 5.90 (s, 1H), 6.95-7.05 (m, 5H), 7.05-7.15 (m, 2H), 7.30-7.40 (m, 2H), 7.45 (m, 2H); MS [M-Br]$^{30}$: 454; mp 98° C.

EXAMPLE 35

3(R)-(2,2-Dithien-2-ylacetoxy)-1-(3-phenoxypropyl)-1-azoniabicyclo [2.2.2]octane; bromide The title compound was synthesised according to methods c and a. The yield of final step was 280 mg, 83%. $^1$H-NMR (DMSO-d6): δ 1.80-2.06 (m, 4H), 2.06-2.20 (m, 2H), 2.20-2.30 (m, 1H), 3.20-3.65 (m, 7H), 3.90-4.10 (m, 3H), 5.20

(m, 1H), 5.90 (s, 1H), 6.95-7.05 (m, 5H), 7.05-7.20 (m, 2H), 7.30-7.35 (m, 2H), 7.50 (m, 2H); MS [M-Br]$^{3O}$ : 468; mp 148° C.

EXAMPLE 36

3(R)-(2-Hydroxy-2,2-dithien-2-ylacetoxy)-1-phenethyl-1-azoniabicyclo [2.2.2]octane; bromide The title compound was synthesised according to methods c and a. The yield of final step was 180 mg, 59%. $^1$H-NMR (DMSO-d6): δ 1.65-2.0 (4H, m), 2.35 (m, 1H), 3.0 (m, 2H), 3.2-3.6 (m, 7H), 3.95 (m, 1H), 5.25 (m, 1H), 7.0 (m, 2H), 7.2 (m, 2H), 7.35 (m, 5H), 7.55 (m, 3H); MS [M-Br]$^{3O}$ : 454; mp 216° C.

EXAMPLE 37

3(R)-(2-Hydroxy-2,2-dithien-2-ylacetoxy)-1-(3-phenylpropyl)-1-azoniabicyclo[2.2.2]octane; bromide The title compound was synthesised according to methods c and a. The yield of final step was 450 mg, 58%. $^1$H-NMR (CDCl$_3$): δ 1.8-2.1 (m, 6H), 2.4 (m, 1H), 2.6 (m, 2H), 3.4-3.8 (m, 7H), 4.2 (m, 1H), 5.25 (m, 1H), 6.1 (bs, OH), 6.9 (m, 2H), 7.1-7.3 (m, 9H); MS [M-Br]$^+$: 468; mp 64° C.

EXAMPLE 38

3(R)-(2-Hydroxy-2,2-dithien-2-ylacetoxy)-1-(3-phenylallyl)-1-azoniabicyclo[2.2.2]octane; bromide The title compound was synthesised according to methods c and a. The yield of final step was 260 mg, 34%. $^1$H-NMR (CDCl$_3$): δ 1.8-2.05 (m, 4H), 2.4 (m, 1H), 3.55-3.95 (m, 5H), 4.15-4.5 (m, 3H), 5.25 (m, 1H), 5.9 (s, OH), 6.15 (m, 1H), 6.85 (t, 1H), 6.9-7.05 (m, 3H), 7.15 (m, 1H), 7.2-7.45 (m, 7H); MS [M-Br]$^{3O}$ : 466; mp 124° C.

EXAMPLE 39

3(R)-(2-Hydroxy-2,2-dithien-2-ylacetoxy)-1-(4-phenylbutyl)-1-azoniabicyclo[2.2.2]octane; bromide The title compound was synthesised according to methods c and a. The yield of final step was 320 mg, 40%. $^1$H-NMR (CDCl$_3$): δ 1.6-2.0 (m, 8H), 2.4 (m, 1H), 2.6 (m, 2H), 3.4-3.8 (m, 7H), 4.2 (m, 1H), 5.25 (m, 1H), 6.05 (bs, OH), 6.95 (m, 2H), 7.1-7.3 (m, 9H); MS [M-Br]$^+$: 482; mp 64° C.

EXAMPLE 40

3(R)-(2-Hydroxy-2,2-dithien-2-ylacetoxy)-1-(4-oxo-4-phenylbutyl)-1-azoniabicyclo[2.2.2]octane; trifluoroacetate The title compound was synthesised according to methods c and b. The yield of final step was 16 mg, 15%. $^1$H-NMR (DMSO-d6): δ 1.7-2.0 (m, 6H), 2.15 (m, 1H), 3.1 (t, 2H), 3.15-3.55 (m, 7H), 3.95 (m, 1H), 5.25 (m, 1H), 7.0 (d, 2H), 7.15 (d, 2H), 7.55 (m, 5H), 7.65 (t, 1H), 8.0 (d, 2H); MS [M-CF$_3$COO]$^+$: 496.

EXAMPLE 41

3(R)-(2-Hydroxy-2,2-dithien-2-ylacetoxy)-1-(3-phenylaminopropyl)-1-azonlabicyclo[2.2.2] octane; trifluoroacetate The title compound was synthesised according to methods c and b. The yield of final step was 14 mg, 14%. $^1$H-NMR (DMSO-d6): δ 1.7-2.0 (m, 5H), 2.3 (m, 1H), 3.0-3.5 (m, 9H), 3.9 (m, 1H), 5.25 (m, 1H), 5.65 (t, 1H), 6.55 (m, 3H), 7.0 (d, 2H), 7.1 (t, 2H), 7.15 (m, 2H), 7.5 (m, 3H); MS[M-CF$_3$COO]$^+$: 483.

EXAMPLE 42

3(R)-(2-Hydroxy-2,2-dithien-2-ylacetoxy)-1-[3-(methylphenylamino)propyl]-1-azoniabicyclo[2.2.2] octane; trifluoroacetate The title compound was synthesised according to methods c and b. The yield of final step was 20 mg, 19%. $^1$H-NMR (DMSO-d6): δ 1.65-2.0 (m, 6H), 2.9 (s, 3H), 3.1 (m, 1H), 3.2-3.45 (m, 8H), 3.95 (m, 1H), 5.2 (m, 1H), 6.65 (t, 1H), 6.75 (d, 2H), 7.0 (m, 2H), 7, 2 (m, 4H), 7.5 (m, 3H); MS [M-CF$_3$COO]$^+$: 497.

EXAMPLE 43

3(R)-(2-Hydroxy-2,2-dithien-2-ylacetoxy)-1-(3-phenylsulfanylpropyl)-1-azoniabicyclo[2.2.2] octane; bromide The title compound was synthesised according to methods c and a. The yield of final step was 800 mg, 83%. $^1$H-NMR (DMSO-d6): δ 1.6-1.9 (m, 6H), 2.3 (m, 1H), 2.95 (t, 2H), 3.05 (m, 1H), 3.2-3.5 (m, 6H), 3.9 (m, 1H), 5.2 (m, 1H), 7.0 (m, 2H), 7.15 (m, 2H), 7.2 (m, 1H), 7.35 (m, 4H), 7.5 (m, 2H); MS [M-Br]$^{3O}$ : 500.

EXAMPLE 44

3(R)-(2-Hydroxy-2,2-dithien-2-ylacetoxy)-1-(3-phenoxypropyl)-1-azoniabicyclo[2.2.2] octane; bromide The title compound was synthesised according to methods c and a. The yield of final step was 490 mg, 90%. $^1$H-NMR (DMSO-d6): δ 1.7 (m, 2H), 1.95 (m, 2H), 2.1 (m, 2H), 2.3 (m, 1H), 3.2 (m, 1H), 3.45 (m, 6H), 4.0 (m, 3H), 5.15 (m, 1H), 6.9 (m, 3H), 7.0 (m, 2H), 7.2 (m, 2H), 7.3 (t, 2H), 7.5 (m, 3H); MS [M-Br]$^+$: 484; mp 227° C.

EXAMPLE 45

3(R)-(2-Hydroxy-2,2-dithien-2-ylacetoxy)-1-(3-o-tolyloxypropyl)-1-azonlabicyclo[2.2.2] octane; trifluoroacetate The title compound was synthesised according to methods c and b. The yield of final step was 19 mg, 18%. $^1$H-NMR (DMSO-d6): δ 1.7-2.0 (m, 4H), 2.1-2.2 (m, 5H), 2.3 (m, 1H), 3.15-3.5 (m, 7H), 3.9-4.05 (m, 3H), 5.05 (m, 1H), 6.85 (t, 1H), 6.9 (d, 1H), 7.0 (m, 2H), 7.15 (m, 4H), 7.5 (m, 3H); MS [M-CF$_3$COO]$^+$: 498.

EXAMPLE 46

3(R)-(2-Hydroxy-2,2-dithien-2-ylacetoxy)-1-[3-(2,4,6-trimethylphenoxy)propyl]-1-azoniabicyclo[2.2.2]octane; trifluoroacetate The title compound was synthesised according to methods c and b. The yield of final step was 22 mg, 20%. $^1$H-NMR (DMSO-d6): δ 1.7 (m, 2H), 1.95 (m, 2H), 2.1 (m, 2H), 2.2 (s, 9H), 2.35 (m, 1H), 3.2-3.5 (m, 7H), 3.7 (t, 2H), 3.95 (m, 1H), 5.25 (m, 1H), 6.8 (s, 2H), 7.0 (m, 2H), 7.2 (m, 2H), 7.5 (m, 3H); MS [M-CF$_3$COO]$^+$: 526.

EXAMPLE 47

1-[3-(2-tert-Butyl-6-methylphenoxy)propyl]-3(R)-(2-hydroxy-2,2-dithien-2-ylacetoxy)-1-azonlabicyclo[2.2.2]octane; trifluoroacetate The title compound was synthesised according to methods c and b. The yield of final step was 18 mg, 16%. $^1$H-NMR (DMSO-d6): δ 1.3 (s, 9H), 2.7 (m, 2H), 2.9 (m, 2H), 2.1 (m, 2H), 2.2 (s, 3H), 2.3 (m, 1H), 3.2-3.5 (m, 7H), 3.8 (t, 2H), 3.95 (m, 1H), 5.2 (m, 1H), 6.9-7.15 (m, 7H), 7.5 (m, 3H); MS [M-CF$_3$COO]$^+$: 554.

EXAMPLE 48

1-[3-(Biphenyl-4-yloxy) propyl]-3(R)-(2-hydroxy-2,2-dithien-2-ylacetoxy)-1-azoniabicyclo[2.2.2]-octane; trifluoroacetate The title compound was synthesised according to methods c and b. The yield of final step was 22 mg, 19%. $^1$H-NMR (DMSO-d6): δ 1.7 (m, 2H), 1.9 (m, 2H), 2.15 (m, 2H), 2.3 (m, 1H), 3.2-3.5 (m, 7H), 3.95 (m, 1H), 4.1 (t, 2H), 5.25 (m, 1H), 7.0 (m, 4H), 7.2 (m, 2H), 7.3 (t, 1H), 7.45 (t, 2H), 7.5 (m, 3H), 7.6 (m, 4H); MS [M-CF$_3$COO]$^+$: 560.

EXAMPLE 49

3(R)-(2-Hydroxy-2,2-dithien-2-ylacetoxy)-1-[3-(5,6,7,8-tetrahydronaphthalen-2-yloxy)-propyl]-1-azoniabicyclo[2.2.2]octane; trifluoroacetate The title compound was synthesised according to methods c and b. The yield of final step was 23 mg, 21%. $^1$H-NMR (DMSO-d6): δ 1.7 (m, 6H), 1.9-2.1 (m, 4H), 2.3 (m, 1H), 2.65 (m, 4H), 3.15-3.5 (m, 7H), 3.95 (m, 2H), 5.25 (m, 1H), 6.65 (m, 2H), 6.95 (d, 1H), 7.0 (m, 2H), 7.2 (m, 2H), 7.5 (m, 3H); MS [M-CF$_3$COO]$^+$: 538.

EXAMPLE 50

3(R)-(2-Hydroxy-2,2-dithien-2-ylacetoxy)-1-[3-(naphthalen-2-yloxy) propyl]-1-azoniabicyclo[2.2.2]octane; trifluoroacetate The title compound was synthesised according to methods c and b. The yield of final step was 17 mg, 15%. $^1$H-NMR (DMSO-d6): δ 1.7-2.0 (m, 4H), 2.1 (m, 1H), 2.35 (m, 1H), 3.15-3.35 (m, 7H), 3.95 (m, 1H), 4.17 (t, 2H), 5.25 (m, 1H), 7.0 (m, 2H), 7.15 (m, 3H), 7.35 (m, 2H), 7.5 (m, 4H), 7.85 (m, 3H); MS [M-CF$_3$COO]$^+$: 534.

EXAMPLE 51

3(R)-(2-Hydroxy-2,2-dithien-2-ylacetoxy)-1-[3-(naphthalen-1-yloxy)propyl]-1-azoniabicyclo[2.2.2]octane; trifluoroacetate The title compound has been described in method -b-.

EXAMPLE 52

1-[3-(2-Chlorophenoxy)propyl]-3(R)-(2-hydroxy-2,2-dithien-2-ylacetoxy)-1-azonlabicyclo [2.2.2]octane; trifluoroacetate The title compound was synthesised according to methods c and b. The yield of final step was 20 mg, 18%. $^1$H-NMR (DMSO-d6): δ 1.65-2.0 (m, 6H), 2.35 (m, 1H), 3.2 (m, 1H), 3.3-3.55 (m, 6H), 3.95 (m, 1H), 4.15 (t, 2H), 5.25 (m, 2H), 7.0 (m, 3H), 7.2 (m, 3H), 7.35 (t, 1H), 7.45 (d, 1H), 7.55 (m, 3H); MS [M-CF$_3$COO]$^+$: 519.

EXAMPLE 53

1-[3-(4-Fluorophenoxy)propyl]-3(R)-(2-hydroxy-2,2-dithien-2-ylacetoxy)-1-azoniabicyclo [2.2.2]octane; chloride The title compound was synthesised according to methods c and a. The yield of final step was 180 mg, 59%. $^1$H-NMR (DMSO-d6): δ 1.65-2.15 (m, 6H), 2.25 (m, 1H), 3.2 (m, 1H), 3.25-3.55 (m, 6H), 3.95 (m, 2H), 4.0 (t, 2H), 5.25 (m, 1H), 7.0 (m, 4H), 7.15 (m, 4H), 7.55 (m, 3H); MS [M-Cl]$^+$: 502; mp 160° C.

EXAMPLE 54

1-[3-(2,4-Difluorophenoxy) propyl]-3(R)-(2-hydroxy-2,2-dithien-2-ylacetoxy)-1-azoniabicyclo [2.2.2]octane; trifluoroacetate The title compound was synthesised according to methods c and b. The yield of final step was 14 mg, 13%. $^1$H-NMR (DMSO-d6): δ 1.65-2.0 (m, 4H), 2.15 (m, 2H), 2.35 (m 1H), 3.2 (m, 1H), 3.25-3.35 (m, 6H), 3.95 (m, 1H), 4.1 (t, 2H), 5.15 (m, 1H), 7.05 (m, 3H), 7.2 (d, 2H), 7.25-7.35 (m, 2H), 7.55 (m, 3H); MS [M-CF$_3$COO]$^+$: 520.

EXAMPLE 55

3(R)-(2-Hydroxy-2,2-dithien-2-ylacetoxy)-1-[3-(3-trifluoromethylphenoxy)propyl]-1-azoniabicyclo [2.2.2]octane; trifluoroacetate The title compound was synthesised according to methods c and b. The yield of final step was 19 mg, 17%. $^1$H-NMR (DMSO-d6): δ 1.65-2.1 (m, 6H), 2.35 (m, 1H), 3.2 (m, 1H), 3.3-3.55 (m, 6H), 3.95 (m, 1H), 4.15 (t, 2H), 5.25 (m, 1H), 7.0 (m, 2H), 7.2 (m, 2H), 7.25-7.35 (m, 3H), 7.5-7.6 (m, 4H); MS [M-CF$_3$COO]$^+$: 552.

EXAMPLE 56

1-[3-(3-Cyanophenoxy) propyl]-3(R)-(2-hydroxy-2,2-dithien-2-ylacetoxy)-1-azoniabicyclo[2.2.2]octane; trifluoroacetate The title compound was synthesised according to methods c and b. The yield of final step was 18 mg, 17%. $^1$H-NMR (DMSO-d6): δ 1.65-2.1 (m, 6H), 2.35 (m, 1H), 3.2 (m, 1H), 3.3-3.55 (m, 6H), 3.95 (m, 1H), 4.15 (t, 2H), 5.25 (m, 1H), 7.0 (m, 2H), 7, 18 (m, 2H), 7.3 (d, 1H), 7.45 (m, 2H), 7.55 (m, 4H); MS [M-CF$_3$COO]$^+$: 509.

EXAMPLE 57

1-[3-(4-Cyanophenoxy)propyl]-3(R)-(2-hydroxy-2,2-dithien-2-ylacetoxy)-1-azonlabicyclo [2.2.2]octane; bromide The title compound was synthesised according to methods c and a. The yield of final step was 180 mg, 53%. $^1$H-NMR (DMSO-d6): δ 1.65-2.2 (m, 6H), 2.3 (m, 1H), 3.2 (m, 1H), 3.3-3.55 (m, 6H), 3.95 (m, 1H), 4.15 (t, 2H), 5.25 (m, 1H), 7.0 (m, 2H), 7.1 (d, 2H), 7.15 (m, 2H), 7.5 (m, 2H), 7.8 (d, 2H); MS [M-Br]$^+$: 509; mp 158° C.

EXAMPLE 58

3(R)-(2-Hydroxy-2,2-dithien-2-ylacetoxy)-1-[3-(3-methoxyphenoxy)propyl]-1-azonia bicyclo[2.2.2] octane; trifluoroacetate The title compound was synthesised according to methods c and b. The yield of final step was 19 mg, 18%. $^1$H-NMR (DMSO-d6): δ 1.65-2.15 (m, 6H), 2.15 (m, 1H), 3.2 (m, 1H), 3.3-3.5 (m, 6H), 3.75 (s, 3H), 3.95 (m, 1H), 4.0 (t, 2H), 5.25 (m, 1H), 6.55 (m, 3H), 7.0 (m, 2H), 7.2 (m, 3H), 7.55 (m, 3H); MS [M-CF$_3$COO]$^+$: 514.

EXAMPLE 59

3(R)-(2-Hydroxy-2,2-dithien-2-ylacetoxy)-1-[3-(4-methoxyphenoxy)propyl]-1-azonlabicyclo[2.2.2] octane; trifluoroacetate The title compound was synthesised according to methods c and b. The yield of final step was 14 mg, 13%. $^1$H-NMR (DMSO-d6): δ 1.65-2.15 (m, 6H), 2.35 (m, 1H), 3.2 (m, 1H), 3.3-3.55 (m, 6H), 3.7 (s, 3H), 3.9-4.0 (m, 3H), 5.25 (m, 1H), 6.9 (s, 4H), 7.0 (m, 2H), 7.15 (m, 2H), 7.5 (m, 3H); MS [M-CF$_3$COO]$^+$: 514.

EXAMPLE 60

1-[3-(Benzo[1,3]dioxol-5-yloxy)propyl]-3(R)-(2-hydroxy-2,2-dithien-2-ylacetoxy)-1-azoniabicyclo [2.2.2]octane; trifluoroacetate The title compound was synthesised according to methods c and b. The yield of final step was 19 mg, 17%. $^1$H-NMR (DMSO-d6): δ 1.65-2.15 (m, 7H), 2.3 (m, 1H), 3.15 (m, 1H), 3.25-3.5 (m, 6H), 3.9-4.0 (m, 3H), 5.25 (m, 1H), 5.95 (s, 2H), 6.4 (d, 1H), 6.65 (s, 1H), 6.85 (d, 1H), 7.0 (m, 2H), 7.2 (m, 2H), 7.5 (m, 3H); MS [M-CF$_3$COO]$^+$: 528.

EXAMPLE 61

1-[3-(2-Carbamoylphenoxy)propyl]-3(R)-(2-hydroxy-2,2-dithien-2-ylacetoxy)-1-azoniabicyclo [2.2.2]octane; trifluoroacetate The title compound was synthesised according to methods c and b. The yield of final step was 18 mg, 16%. $^1$H-NMR (DMSO-d6): δ 1.65-2.0 (m, 4H), 2.2 (m, 2H), 2.3 (m, 1H), 3.15 (m, 1H), 3.25-3.55 (m, 6H), 3.95 (m, 1H), 4.15 (t, 2H), 5.25 (m, 1H), 7.0-7.2 (m, 6H), 7.4-7.6 (m, 6H), 7.7 (d, 1H); MS [M-CF$_3$COO]$^+$: 527.

EXAMPLE 62

1-[3-(3-Dimethylaminophenoxy)propyl]-3(R)-(2-hydroxy-2,2-dithien-2-ylacetoxy)-1-azoniabicyclo [2.2.2]octane; trifluoroacetate The title compound was synthesised according to methods c and b. The yield of final step was 19 mg, 17%. $^1$H-NMR (DMSO-d6): δ 1.65-2.15 (m, 6H), 2.3 (m, 1H), 2.85 (s, 6H), 3.1-3.5 (m, 7H), 3.85-4.0 (m, 3H), 5.25 (m, 1H), 6.2 (m, 1H), 6.25 (d, 1H), 6.35 (d, 1H), 7.0 (m, 2H), 7.1 (t, 1H), 7.2 (m, 2H), 7.5 (m, 3H); MS [M-CF$_3$COO]$^+$: 527.

EXAMPLE 63

3(R)-(2-Hydroxy-2,2-dithien-2-ylacetoxy)-1-[3-(4-nitrophenoxy)propyl]-1-azoniabicyclo[2.2.2]octane; trifluoroacetate The title compound was synthesised according to methods c and b. The yield of final step was 22 mg, 20%. $^1$H-NMR (DMSO-d6): δ 1.65-2.0 (m, 4H), 2.2 (m, 2H), 2.3 (m, 1H), 3.2 (m, 1H), 3.3-3.5 (m, 6H), 3.95 (m, 1H), 4.2 (t, 2H), 5.25 (m, 1H), 7.0 (m, 2H), 7.15 (m, 4H), 7.5 (m, 3H), 8.15 (d, 2H); MS [M-CF$_3$COO]$^+$: 529.

EXAMPLE 64

3(R)-(2-Hydroxy-2,2-dithien-2-ylacetoxy)-1-[3-(3-nitrophenoxy)propyl]-1-azoniabicyclo [2.2.2]octane; trifluoroacetate The title compound was synthesised according to methods c and b. The yield of final step was 18 mg, 16%. $^1$H-NMR (DMSO-d6): δ 1.65-2.2 (m, 6H), 2.3 (m, 1H), 3.15-3.55 (m, 7H), 3.95 (m, 1H), 4.2 (t, 2H), 5.25 (m, 1H), 7.0 (m, 2H), 7.2 (m, 2H), 7.45 (dd, 1H), 7.55 (m, 3H), 7.6 (t, 1H), 7.75 (s, 1H), 7.85 (d, 1H); MS [M-CF$_3$COO]$^+$: 529.

EXAMPLE 65

1-[3-(4-Acetylaminophenoxy)propyl]-3(R)-(2-hydroxy-2,2-dithien-2-ylacetoxy)-1-azoniabicyclo [2.2.2]octane; trifluoroacetate The title compound was synthesised according to methods c and b. The yield of final step was 19 mg, 17%. $^1$H-NMR (DMSO-d6): δ 1.65-2.15 (m, 6H), 2.0 (s, 3H), 2.3 (m, 1H), 3.2 (m, 1H), 3.3-3.55 (m, 6H), 3.9-4.0 (m, 3H), 5.25 (m, 1H), 6.85 (d, 2H), 7.0 (m, 2H), 7.2 (m, 2H), 7.5 (m, 5H), 9.8 (s, 1H); MS [M-CF$_3$COO]$^+$: 541.

EXAMPLE 66

3(R)-(2-Hydroxy-2,2-dithien-2-ylacetoxy)-1-[3-(3-methoxycarbonylphenoxy)propyl]-1-azoniabicyclo[2.2.2]octane; trifluoroacetate The title compound was synthesised according to methods c and b. The yield of final step was 18 mg, 16%. $^1$H-NMR (DMSO-d6): δ 1.65-2.2 (m, 6H), 2.3 (m, 1H), 3.2 (m, 1H), 3.3-3.5 (m, 6H), 3.85 (s, 3H), 3.95 (m, 1H), 4.1 (t, 2H), 5.25 (m, 1H), 7.0 (m, 2H), 7.15 (m, 2H), 7.25 (dd, 1H), 7.45-7.6 (m, 6H); MS [M-CF$_3$COO]$^+$: 542.

EXAMPLE 67

3(R)-(2-Hydroxy-2,2-dithien-2-ylacetoxy)-1-{3-[4-(3-hydroxypropyl) phenoxy]propyl}-1-azoniabicyclo[2.2.2]octane; trifluoroacetate The title compound was synthesised according to methods c and b. The yield of final step was 14 mg, 13%. $^1$H-NMR (DMSO-d6): δ 1.6-2.15 (m, 8H), 2.3 (m, 1H), 2.55 (t, 2H), 3.2 (m, 1H), 3.25-3.55 (m, 9H), 3.85-4.0 (m, 3H), 4.45 (t, OH), 5.25 (m, 1H), 7.85 (d, 2H), 7.0 (m, 2H), 7.1 (d, 2H), 7.15 (m, 2H), 7.5 (m, 2H); MS [M-CF$_3$COO]$^+$: 542.

EXAMPLE 68

3(R)-(2-Hydroxy-2,2-dithien-2-ylacetoxy)-1-[3-(2-hydroxymethylphenoxy)propyl]-1-azoniabicyclo[2.2.2]octane; trifluoroacetate The title compound was synthesised according to methods c and b. The yield of final step was 16 mg, 15%. $^1$H-NMR (DMSO-d6): δ 1.7-2.2 (m, 6H), 2.35 (m, 1H), 3.1-3.5 (m, 7H), 3.9-4.05 (m, 3H), 4.5 (m, 2H), 5.0 (t, OH), 5.15 (m, 1H), 6.9-7.05 (m, 4H), 7.2 (m, 2H), 7.4 (d, 1H), 7.5 (m, 3H); MS [M-CF$_3$COO]$^+$: 514.

EXAMPLE 69

3(R)-(2-Hydroxy-2,2-dithien-2-ylacetoxy)-1-[3-(3-hydroxymethylphenoxy) propyl]-1-azoniabicyclo[2.2.2]octane; trifluoroacetate The title compound was synthesised according to methods c and b. The yield of final step was 16 mg, 15%. $^1$H-NMR (DMSO-d6): δ 1.7-2.2 (m, 6H), 2.35 (m, 1H), 3.15-3.5 (m, 7H), 3.9 (m, 1H), 4.05 (t, 2H), 4.45 (d, 2H), 5, 25 (m, 2H), 6.8 (d, 1H), 6.9 (m, 2H), 7.2 (m, 2H), 7.25 (t, 1H), 7.5 (m, 3H); MS [M-CF$_3$COO]$^+$: 514.

EXAMPLE 70

3(R)-(2-Hydroxy-2,2-dithien-2-ylacetoxy)-1-[3-(4-hydroxymethylphenoxy)propyl]-1-azoniabicyclo[2.2.2]octane; trifluoroacetate The title compound was synthesised according to methods c and b. The yield of final step was 17 mg, 16%. $^1$H-NMR (DMSO-d6): δ 1.65-2.2 (m, 6H), 2.3 (m, 1H), 3.15-3.55 (m, 7H), 3.9-4.05 (m, 3H), 4.4 (d, 2H), 5.1 (t, OH), 5.25 (t, 1H), 6.9 (d, 2H), 7.0 (m, 2H), 7.2 (m, 2H), 7.25 (d, 2H), 7.5 (m, 3H); MS [M-CF$_3$COO]$^+$: 514.

EXAMPLE 71

3(R)-(2-Hydroxy-2,2-dithien-2-ylacetoxy)-1-[3-(2-hydroxyphenoxy)propyl]-1-azoniabicyclo[2.2.2]octane; trifluoroacetate The title compound was synthesised according to methods c and b. The yield of final step was 24 mg, 19%. $^1$H-NMR (DMSO-d6): δ 1.65-2.15 (m, 6H), 2.35 (m, 1H), 3.2 (m, 1H), 3.25-3.55 (m, 6H), 3.95 (m, 1H), 4.0 (t, 2H), 5.25 (m, 1H), 6.7-6.85 (m, 3H), 6.95 (d, 1H), 7.0 (m, 2H), 7.2 (m, 2H), 7.5 (m, 3H), 8.85 (s, OH); MS [M-CF$_3$COO]$^+$: 500.

EXAMPLE 72

3(R)-(2-Hydroxy-2,2-dithien-2-ylacetoxy)-1-[3-(4-hydroxyphenoxy)propyl]-1-azoniabicyclo[2.2.2]octane; trifluoroacetate The title compound was synthesised according to methods c and b. The yield of final step was 16 mg, 15%. $^1$H-NMR (DMSO-d6): δ 1.65-2.1 (m, 6H), 2.3 (m, 1H), 3.2 (m, 1H), 3.25-3.5 (m, 6H), 3.95 (m, 3H), 5.25 (m, 1H), 6.7 (d, 2H), 6.75 (d, 2H), 7.0 (m, 2H), 7.2 (m, 2H), 7.5 (t, 3H), 9.0 (s, OH); MS [M-CF$_3$COO]$^+$: 500.

EXAMPLE 73

3(R)-(2-Hydroxy-2,2-dithien-2-ylacetoxy)-1-[3-(3-hydroxyphenoxy)propyl]-1-azoniabicyclo[2.2.2]octane; trifluoroacetate The title compound was synthesised according to methods c and b. The yield of final step was 16 mg, 15%. $^1$H-NMR (DMSO-d6): δ 1.65-2.15 (m, 6H), 2.3 (m, 1H), 3.2 (m, 1H), 3.3-3.55 (m, 6H), 3.9-4.0 (m, 3H), 5.25 (m, 1H), 6.9-6.0 (m, 3H), 7.0-7.1 (m, 3H), 7.2 (m, 2H), 7.5 (m, 3H), 9.45 (s, OH); MS [M-CF$_3$COO]$^+$: 500.

EXAMPLE 74

3(R)-(2-Hydroxy-2,2-dithien-2-ylacetoxy)-1-(3-pyrrol-1-ylpropyl)-1-azoniabicyclo[2.2.2]octane; trifluoroacetate The title compound was synthesised according to methods c and b. The yield of final step was 21 mg, 22%. $^1$H-NMR (DMSO-d6): δ 1.65-1.8 (m, 2H), 1.8-2.0 (m, 2H), 2.0-2.15 (m, 2H), 2.3 (m, 1H), 3.05-3.2 (m, 3H), 3.2-3.5 (m, 4H), 3.8-3.95 (m, 3H), 5.2 (m, 1H), 6.05 (t, 2H), 6.75 (t, 2H), 7.0 (t, 2H), 7.15 (d, 2H), 7.55 (m, 3H); MS [M-CF$_3$COO]$^+$: 457.

EXAMPLE 75

3(R)-(2-Hydroxy-2,2-dithien-2-ylacetoxy)-1-(4-oxo-4-thien-2-ylbutyl)-1-azoniabicyclo[2.2.2]octane; trifluoroacetate The title compound was synthesised according to methods c and b. The yield of final step was 18 mg, 17%. $^1$H-NMR (DMSO-d6): δ 1.7-1.85 (m, 2H), 1.9-2.1 (m, 4H), 2.3 (m, 1H), 3.1 (t, 2H), 3.15-3.55 (m, 7H), 3.95 (m, 1H), 5.25 (m, 1H), 7.0 (t, 2H), 7.4 (d, 2H), 7.25 (t, 1H), 7.55 (m, 3H), 7.95 (d, 1H), 8.05 (d, 1H); MS [M-CF$_3$COO]$^+$: 502.

EXAMPLE 76

3(R)-(2-Hydroxy-2,2-dithien-2-ylacetoxy)-1-[3-(1-methyl-[1H]-imidazol-2-ylsulfanyl)propyl]-1-azoniabicyclo[2.2.2]octane; trifluoroacetate The title compound was synthesised according to methods c and b. The yield of final step was 26 mg, 25%. $^1$H-NMR (DMSO-d6): δ 1.7 (m, 2H), 1.85-2.05 (m, 4H), 2.3 (m, 1H), 3.25-3.5 (m, 7H), 3.6 (s, 3H), 3.9 (m, 1H), 4.2 (t, 2H), 5.2 (m, 1H), 7.0 (m, 3H), 7.15 (m, 2H), 7.3 (m, 1H), 7.5 (m, 3H); MS [M-CF$_3$COO]$^+$: 504.

EXAMPLE 77

3(R)-(2-Hydroxy-2,2-dithien-2-ylacetoxy)-1-(2-thien-2-ylethyl)-1-azoniabicyclo[2.2.2]octane; bromide The title compound was synthesised according to methods c and a. The yield of final step was 430 mg, 54%. $^1$H-NMR (DMSO-d6): δ 1.6-1.8 (m, 2H), 2.3 (m, 1H), 3.15-3.3 (m, 4H), 3.35-3.55 (m, 5H), 3.95 (m, 1H), 5.25 (m, 1H), 7.0 (m, 4H), 7.15 (m, 2H), 7.4-7.5 (m, 4H); MS [M-Br]$^+$: 460; mp 206° C.

EXAMPLE 78

3(R)-(2-Hydroxy-2,2-dithien-2-ylacetoxy)-1-(3-thien-2-ylpropyl)-1-azoniabicyclo[2.2.2]octane; bromide The title compound was synthesised according to methods c and a. The yield of final step was 600 mg, 77%. $^1$H-NMR (DMSO-d6): δ 1.6-1.8 (m, 2H), 1.85-2.1 (m, 4H), 2.3 (m, 1H), 2.8 (t, 2H), 3.1-3.5 (m, 7H), 3.9 (m, 1H), 5.2 (m, 1H), 6.9-7.05 (m, 4H), 7.15 (m, 2H), 7.4 (d, 1H), 7.5 (m, 3H); MS [M-Br]$^+$: 474; mp 138° C.

EXAMPLE 79

1-[3-(Benzothiazol-2-yloxy) propyl]-3(R)-(2-hydroxy-2,2-dithien-2-ylacetoxy)-1-azoniabicyclo[2.2.2]octane; trifluoroacetate The title compound was synthesised according to methods c and b. The yield of final step was 23 mg, 21%. $^1$H-NMR (DMSO-d6): δ 1.65-2.1 (m, 6H), 2.3 (m, 1H), 3.15 (m, 1H), 3.25-3.5 (m, 6H), 3.85 (m, 1H), 4.0 (t, 2H), 5.2 (m, 1H), 7.0 (t, 2H), 7.15 (m, 2H), 7.25 (m, 1H), 7.45 (m, 5H), 7.7 (d, 1H); MS [M-CF$_3$COO]$^+$: 541.

EXAMPLE 80

1-(3-Benzyloxypropyl)-3(R)-(2-hydroxy-2,2-dithien-2-ylacetoxy)-1-azoniabicyclo[2.2.2]octane; trifluoroacetate The title compound was synthesised according to methods c and b. The yield of final step was 16 mg, 15%. $^1$H-NMR (DMSO-d6): δ 1.65 (m, 2H), 1.9 (m, 4H), 2.3 (m, 1H), 3.1-3.4 (m, 7H), 3.5 (t, 2H), 3.9 (m, 1H), 3.9 (s, 2H), 5.2 (m, 1H), 7.0 (m, 2H), 7.15 (m, 2H), 7.35 (m, 5H), 7.5 (m, 3H); MS [M-CF$_3$COO]$^+$: 498.

EXAMPLE 81

3(R)-(2-Hydroxy-2,2-dithien-2-ylacetoxy)-1-[6-(4-phenylbutoxy)hexyl]-1-azoniabicyclo [2.2.2]octane; bromide The title compound was synthesised according to methods c and a. The yield of final step was 560 mg, 60%. $^1$H-NMR (CDCl$_3$): δ 1.2-1.75 (m, 16H), 1.8-2.1 (m, 4H), 2.4 (m, 1H), 2.6 (t, 2H), 3.3-3.75 (m, 11H), 4.2 (m, 1H), 5.3 (m, 1H), 6.0 (bs, OH), 6.95 (m, 2H), 7.15-7.3 (m, 9H); MS [M-Br]$^+$: 582.

EXAMPLE 82

3(R)-(2-Hydroxy-2,2-dithien-2-ylacetoxy)-1-(4-phenoxybutyl)-1-azoniabicyclo[2.2.2]octane; bromide The title compound was synthesised according to methods c and a. The yield of final step was 240 mg, 30%. $^1$H-NMR (DMSO-d6/CDCl$_3$): δ 1.8-1.95 (m, 6H), 2.1 (m, 2H), 2.45 (m, 1H), 3.18 (m, 1H), 3.5-3.8 (m, 6H), 4.0 (t, 2H), 4.15 (m, 1H), 5.15 (m, 1H), 6.7 (s, OH), 6.9 (m, 5H), 7.15 (d, 1H), 7.25 (m, 5H); MS [M-Br]$^{3O}$ : 498; mp 161° C.

EXAMPLE 83

3(R)-(2-Hydroxy-2,2-dithien-2-ylacetoxy)-1-(2-phenoxyethyl)-1-azoniabicyclo[2.2.2]octane; bromide The title compound was synthesised according to methods c and a. The yield of final step was 380 mg, 50%. $^1$H-NMR (DMSO-d6): δ 1.85 (m, 2H), 2.05 (m, 2H), 2.4 (m, 1H), 3.6-4.1 (m, 7H), 4.35 (m, 3H), 5.25 (m, 1H), 6.0 (bs, OH), 6.9 (m, 4H), 7.0 (t, 1H), 7.1 (dd, 2H), 7.2 (dd, 2H), 7.3 (t, 2H); MS [M-Br]$^{3O}$ : 470; mp 48° C.

EXAMPLE 84

1-(2-Benzyloxyethyl)-3(R)-(2-hydroxy-2,2-dithien-2-ylacetoxy)-1-azoniabicyclo[2.2.2]octane; trifluoroacetate The title compound was synthesised according to methods c and b. The yield of final step was 17 mg, 17%. $^1$H-NMR (DMSO-d6): δ 1.65-2.0 (m, 4H), 2.3 (m, 1H), 3.2-3.55 (m, 7H), 3.85 (m, 2H), 4.5 (s, 2H), 5.25 (m, 1H), 7.0 (t, 2H), 7.15 (t, 2H), 7.3-7.4 (m, 4H), 7.5 (m, 3H); MS [M-CF$_3$COO]$^+$: 484.

EXAMPLE 85

3(S)-(2-Hydroxy-2,2-di thien-2-ylacetoxy)-1-(3-phenoxypropyl)-1-azoniabicyclo[2.2.2] octane; bromide The title compound was synthesised according to methods c and a. The yield of final step was 600 mg, 54%. $^1$H-NMR (DMSO-d6/CDCl$_3$): δ 1.85-2.3 (m, 6H), 2.5 (m, 1H), 3.3 (m, 1H), 3.4 (d, 1H), 3.5-3.7 (m, 5H), 4.05 (t, 2H), 4.2 (m, 1H), 5.25 (m, 1H), 6.85 (d, 2H), 7.0 (m, 3H), 7.15 (m, 2H), 7.2 (d, 1H), 7.3 (m, 4H); MS [M-Br]$^+$: 484; mp 230° C.

EXAMPLE 86

4-(2-Hydroxy-2,2-dithien-2-ylacetoxy)-1-(3-phenoxypropyl)-1-azoniabicyclo[2.2.2]octane; bromide The title compound was synthesised according to methods f and a. The yield of final step was 290 mg, 60%. $^1$H-NMR (DMSO-d6): δ 2.15 (m, 2H), 2.35 (m, 6H), 3.35 (m, 2H), 3.65 (m, 6H), 4.05 (t, 2H), 6.9-7.05 (m, 5H), 7.1 (m, 2H), 7.3 (m, 3H), 7.55 (m, 2H); MS [M-Br]$^+$:484 mp 168° C.

EXAMPLE 87

4-(2-Hydroxy-2,2-dithien-2-yl-acetoxy)-1-phenethyl-1-azoniabicyclo[2.2.2]octane; bromide The title compound was synthesised according to methods f and a. The yield of final step was 260 mg, 57%. $^1$H-NMR (DMSO-d6): δ 2.35 (m, 6H), 3.0 (m, 2H), 3.4 (m, 2H), 3.75 (m, 6H), 7.0 (m, 2H), 7.3-7.5 (m, 6H), 7.55 (m, 2H); MS [M-Br]$^+$: 454; mp 195° C.

EXAMPLE 88

1-(3-phenoxypropyl)-3(R)-(2,2-dithien-2-ylpropionyloxy)-1-azoniabicyclo[2.2.2]octane; bromide The title compound was synthesised according to methods c and a. The yield of final step was 390 mg, 92%. $^1$H-NMR (DMSO-d6): δ 1.65-2.20 (m, 6H), 2.10 (s, 3H), 2.30 (bs, 1H), 3.10 (m, 1H), 3.30-3.60 (m, 6H), 3.95-4.10 (m, 3H), 5.20 (m, 1H), 6.90-7.05 (m, 5H), 7.05-7.10 (m, 2H), 7.25-7.35 (m, 2H), 7.50 (m, 2H); MS [M-Br]$^{30}$ : 482; mp 170° C.

EXAMPLE 89

3(R)-(2-Hydroxy-2,2-dithien-3-ylacetoxy)-1-(3-phenoxypropyl)-1-azoniabicyclo[2.2.2]octane; bromide The title compound was synthesised according to methods c and a. The yield of final step was 300 mg, 76%. $^1$H-NMR (DMSO-d6): δ 1.6 (m, 1H), 1.75 (m, 1H), 1.8-2.0 (m, 2H), 2.0-2.2 (m, 2H), 2.3 (m, 1H), 3.15 (m, 1H), 3.3-3.6 (m, 6H), 3.9 (m, 1H), 4.05 (t, 2H), 5.2 (m, 1H), 6.75 (s, OH), 6.95 (m, 3H), 7.15 (m, 2H), 7.3 (t, 2H), 7.4-7.5 (m, 4H); MS [M-Br]$^{30}$ : 484; mp 219° C.

EXAMPLE 90

3(R)-(2-Hydroxy-2,2-dithienyl-3-ylacetoxy)-1-(3-thien-2-ylpropyl)-1-azoniabicyclo[2.2.2]octane; bromide The title compound was synthesised according to methods c and a. The yield of final step was 300 mg, 77%. $^1$H-NMR (DMSO-d6): δ 1.5-1.6 (m, 1H), 1.6-1.75 (m, 1H), 1.8-2.1 (m, 4H), 2.25 (m, 1H), 2.8 (t, 2H), 3.05-3.5 (m, 7H), 3.8-3.95 (m, 1H), 5.15 (m, 1H), 6.75 (s, OH), 6.9-7.0 (m, 2H), 7.1 (m, 2H), 7.35-7.55 (m, 5H); MS [M-Br]$^{30}$ : 474; mp 192° C.

EXAMPLE 91

3(R)-(2-Hydroxy-2,2-dithien-3-yl-acetoxy)-1-phenethyl-1-azoniabicyclo[2.2.2]octane; trifluoroacetate The title compound was synthesised according to methods c and b. The yield of final step was 63 mg, 48%. $^1$H-NMR (DMSO-d6): δ 1.5-1.7 (m, 1H), 1.7-1.85 (m, 1H), 1.9-2.1 (m, 2H), 2.3 (m, 1H), 2.9-3.1 (m, 2H), 3.15-3.6 (m, 7H), 3.9-4.0 (m, 1H), 5.2 (m, 1H), 6.8 (s, OH), 7.1 (m, 2H), 7.25-7.35 (m, 5H), 7.4 (m, 2H), 7.5 (m, 2H); MS [M-CF3COO]$^+$: 454.

EXAMPLE 92

3(R)-(2-Hydroxy-2,2-dithien-3-yl-acetoxy)-1-(3-phenylpropyl)-1-azoniabicyclo[2.2.2]octane; trifluoroacetate The title compound was synthesised according to methods c and b. The yield of final step was 75 mg, 55%. $^1$H-NMR (DMSO-d6): δ 1.5-2.0 (m, 6H), 2.25 (m, 1H), 2.5-2.6 (m, 2H), 3.05-3.6 (m, 8H), 3.8-3.9 (m, 1H), 5.15 (m, 1H), 6.75 (s, OH), 7.1 (d, 2H), 7.2-7.35 (m, 5H), 7.4 (m, 2H), 7.5 (m, 2H); MS [M-CF3COO]$^+$: 468.

EXAMPLE 93

3(R)-(2-Hydroxy-2,2-dithien-3-ylacetoxy)-1-(4-phenylbutyl)-1-azoniabicyclo[2.2.2]octane; trifluoroacetate The title compound was synthesised according to methods c and b. The yield of final step was 68 mg, 48%. $^1$H-NMR (DMSO-d6): δ 1.5-1.8 (m, 6H), 1.8-2.0 (m, 2H), 2.25 (m, 1H), 2.6 (m, 2H), 3.05 (m, 1H), 3.15-3.45 (m, 6H), 3.85 (m, 1H), 5.15 (m, 1H), 6.75 (s, OH), 7.1 (d, 2H), 7.2 (m, 2H), 7.3 (m, 3H), 7.4 (m, 2H), 7.5 (m, 2H); MS [M-CF3COO]$^+$: 482.

EXAMPLE 94

3(R)-(2-Hydroxy-2,2-dithien-3-ylacetoxy)-1-(2-thien-2-ylethyl)-1-azoniabicyclo[2.2.2]octane; trifluoroacetate The title compound was synthesised according to methods c and b. The yield of final step was 65 mg, 49%. $^1$H-NMR (DMSO-d6): δ 1.5-1.65 (m, 1H), 1.65-1.78 (m, 1H), 1.85-2.05 (m, 2H), 2.3 (m, 1H), 3.1-3.6 (m, 9H), 3.95 (m, 1H), 5.2 (m, 1H), 6.75 (s, OH), 7.0 (m, 2H), 7.15 (m, 2H), 7.45 (m, 3H), 7.5 (m, 2H); MS [M-CF3COO]$^+$: 460.

EXAMPLE 95

3(R)-(2-Hydroxy-2,2-dithien-3-ylacetoxy)-1-(4-phenoxybutyl)-1-azoniabicyclo[2.2.2]octane; trifluoroacetate The title compound was synthesised according to methods c and b. The yield of final step was 63 mg, 43%. $^1$H-NMR (DMSO-d6): δ 1.5-2.0 (m, 8H), 2.3 (m, 1H), 3.1 (m, 1H), 3.2-3.5 (m, 6H), 3.85 (m, 1H), 4.0 (m, 2H), 5.2 (m, 1H), 6.75 (s, OH), 6.95 (m, 3H), 7.1 (d, 2H), 7.2 (m, 2H), 7.3 (t, 2H), 7.45 (m, 2H), 7.5 (m, 2H); MS [M-CF3COO]$^+$: 498.

EXAMPLE 96

3(R)-(2-Hydroxy-2,2-dithien-3-ylacetoxy)-1-(2-phenoxyethyl)-1-azoniabicyclo[2.2.2]octane; trifluoroacetate The title compound was synthesised according to methods c and b. The yield of final step was 72 mg, 52%. $^1$H-NMR (DMSO-d6): δ 1.55-1.65 (m, 1H), 1.7-1.8 (m, 1H), 1.85-2.05 (m, 2H), 2.3 (m, 1H), 3.2-3.6 (m, 5H), 3.7 (m, 2H), 4.05 (m, 1H), 4.4 (m, 2H), 5.2 (m, 1H), 6.75 (s, OH), 6.95-7.05 (m, 3H), 7.1 (d, 2H), 7.3-7.5 (m, 6H); MS [M-CF3COO]$^+$: 470.

EXAMPLE 97

1-[3-(4-Fluorophenoxy)propyl]-3(R)-(2-hydroxy-2,2-dithien-3-ylacetoxy)-1-azoniabicyclo[2.2.2]octane; trifluoroacetate The title compound was synthesised according to methods c and b. The yield of final step was 79 mg, 54%. $^1$H-NMR (DMSO-d6): δ 1.55-1.65 (m, 1H), 1.7-1.8 (m, 1H), 1.85-2.0 (m, 2H), 2.05-2.2 (m, 2H), 2.3 (m, 1H), 3.1-3.2 (m, 1H), 3.25-3.55 (m, 6H), 3.85-3.95 (m, 1H), 4.0 (t, 2H), 5.2 (m, 1H), 6.75 (s, OH), 6.95 (m, 2H), 7.15 (m, 4H), 7.4 (m, 2H), 7.5 (m, 2H); MS [M-CF3COO]$^+$: 502.

EXAMPLE 98

3(R)-(2-Hydroxy-2,2-dithien-3-ylacetoxy)-1-(3-phenylallyl)-1-azoniabicyclo[2.2.2]octane; trifluoroacetate The title compound was synthesised according to methods c and b. The yield of final step was 24 mg, 17%. $^1$H-NMR (DMSO-d6): δ 1.8-2.05 (m, 4H), 2.3 (m, 1H), 3.15 (m, 1H), 3.3-3.5 (m, 4H), 3.9 (m, 1H), 4.05 (m 2H), 5.25 (m, 1H), 6.35 (m, 1H), 6.75 (s, OH), 6.85 (t, 1H), 7.1 (m, 2H), 7.3-7.5 (m, 5H), 7.55 (m, 4H); MS [M-CF3COO]$^+$: 502.

EXAMPLE 99

1-(3-phenylallyl)-3(R)-(9-Hydroxy-9[H]-fluorene-9-carbonyloxy)-1-azoniabicyclo[2.2.2]octane; bromide The title compound was synthesised according to methods c and a. The yield of final step was 400 mg, 93%. $^1$H-NMR (DMSO-d6): δ 1.35-1.50 (m, 1H), 1.60-1.75 (m, 1H), 1.75-1.95 (m, 2H), 2.10 (m, 1H), 2.85 (m, 1H), 3.10 (d, 1H), 3.20-3.50 (m, 3H), 3.85 (m, 1H), 4.0 (dd, 2H), 5.05 (m, 1H), 6.40 (dd, 1H), 6.80-6.90 (d, 1H), 6.85 (s, OH), 7.20-7.50 (m, 7H), 7.60 (m, 4H), 7.80 (m, 2H); MS [M-Br]$^{30}$: 452; mp 146° C.

EXAMPLE 100

3(R)-(9-Hydroxy-9[H]-fluorene-9-carbonyloxy)-1-(3-phenoxy-propyl)-1-azoniabicyclo[2.2.2]octane; bromide The title compound was synthesised according to methods c and a. The yield of final step was 690 mg, 83%. $^1$H-NMR (DMSO-d6): δ 1.47 (m, 1H), 1.68 (m, 1H), 1.87 (m, 2H), 2.1 (m, 3H), 2.89 (m, 1H), 3.15 (d, 1H), 3.4 (m, 5H), 3.9 (m, 1H), 4.0 (m, 2H), 5.04 (m, 1H), 6.85 (s, OH), 6.97 (m, 3H), 7.35 (m, 4H), 7.45 (m, 2H), 7.65 (m, 2H), 7.85 (m, 2H); MS [M-Br]$^{30}$: 470; mp 108° C.

EXAMPLE 101

3(R)-(9-Hydroxy-9 [H]-fluorene-9-carbonyloxy)-1-phenethyl-1-azoniabicyclo[2.2.2]octane; bromide The title compound was synthesised according to methods c and a. The yield of final step was 170 mg, 74%. $^1$H-NMR (DMSO-d6): δ 1.45 (m, 1H), 1.65 (m, 1H), 1.85 (m, 2H), 2.1 (m, 1H), 2.9 (m, 1H), 3.15 (m, 1H), 3.3-3.5 (m, 5H), 3.85 (m, 1H), 5.05 (m, 1H), 6.85 (s, OH), 7.2-7.4 (m, 7H), 7.45 (t, 2H), 7.55 (d, 1H), 7.65 (d, 1H), 7.85 (d, 2H); MS [M-Br]$^{30}$: 440; mp 118° C.

EXAMPLE 102

3(R)-(9-Hydroxy-9[H]-fluorene-9-carbonyloxy)-1-(2-phenoxyethyl)-1-azoniabicyclo[2.2.2]octane; bromide The title compound was synthesised according to methods c and a. The yield of final step was 460 mg, 96%. $^1$H-NMR (DMSO-d6): δ 1.42 (m, 1H), 1.66 (m, 1H), 1.80-1.88 (m, 2H), 2.08 (m, 1H), 2.93 (m, 1H), 3.25-3.60 (m, 4H), 3.65 (m, 2H), 3.95 (m, 1H), 4.35 (m, 2H), 5.02 (m, 1H), 6.85 (s, 1H, OH), 6.97 (d, 2H), 7.04 (t, 1H), 7.20-7.45 (m, 6H), 7.55-7.60 (t, 2H), 7.80 (d, 2H); MS [M-Br]$^{30}$: 456; mp 140° C.

EXAMPLE 103

3(R)-(9-Hydroxy-9[H]-fluorene-9-carbonyloxy)-1-(4-oxo-4-phenylbutyl)-1-azoniabicyclo[2.2.2]octane; trifluoroacetate The title compound was synthesised according to methods c and b. The yield of final step was 15 mg, 15%. $^1$H-NMR (DMSO-d6): δ 1.45 (m, 1H), 1.65 (m, 1H), 1.7-2.0 (m, 4H), 2.1 (m, 1H), 2.75 (m, 1H), 3.0-3.2 (m 4H), 3.25-3.4 (m, 4H), 3.85 (m, 1H), 5.05 (m, 1H), 6.85 (s, OH), 7.35 (t, 2H), 7.45 (t, 2H), 7.55-7.7 (m, 5H), 7.85 (d, 2H), 8.0 (d, 2H); MS [M-CF$_3$COO]$^+$: 482.

EXAMPLE 104

1-[3-(4-Fluorophenoxy)propyl]-3(R)-(9-hydroxy-9[H]-fluorene-9-carbonyloxy)-1-azoniabicyclo[2.2.2]octane; chloride The title compound was synthesised according to methods c and a. The yield of final step was 440 mg, 94%. $^1$H-NMR (DMSO-d6): δ 1.4 (m, 1H), 1.65 (m, 2H), 1.7-1.95 (m, 2H), 2.0-2.1 (m, 3H), 2.8 (m, 1H), 3.1 (d, 1H), 3.2-3.4 (m, 5H), 3.8 (m, 1H), 4.0 (t, 2H), 5.0 (m, 1H), 6.85 (s, OH), 6.95 (m, 2H), 7.15 (t, 2H), 7.35 (t, 2H), 7.45 (t, 2H), 7.55 (d, 1H), 7.65 (d, 1H), 7.85 (d, 2H); MS [M-Br]$^{30}$: 488; mp 142° C.

EXAMPLE 105

1-[3-(2,4-Difluorophenoxy)propyl]-3(R)-(9-hydroxy-9[H]-fluorene-9-carbonyloxy)-1-azoniabicyclo[2.2.2]octane; trifluoroacetate The title compound was synthesised according to methods c and b. The yield of final step was 14 mg, 13%. $^1$H-NMR (DMSO-d6): δ 1.4 (m, 1H), 1.6-1.9 (m, 3H), 2.1 (m, 3H), 2.8 (m, 1H), 3.1 (d, 1H), 3.2-3.4 (m, 5H), 3.85 (m, 1H), 4.05 (t, 2H), 5.0 (m, 1H), 6.85 (s, OH), 7.05 (t, 1H), 7.15-7.4 (m, 4H), 7.45 (t, 2H), 7.55 (d, 1H), 7.65 (d, 1H), 7.85 (d, 2H); MS [M-CF$_3$COO]$^+$: 506.

EXAMPLE 106

3(R)-(9-Hydroxy-9[H]-fluorene-9-carbonyloxy)-1-(3-phenylaminopropyl)-1-azoniabicyclo[2.2.2]octane; trifluoroacetate The title compound was synthesised according to methods c and b. The yield of final step was 14 mg, 15%. $^1$H-NMR (DMSO-d6): δ 1.4 (m, 1H), 1.6 (m, 1H), 1.8 (m, 4H), 2.05 (m, 1H), 2.7 (m, 1H), 3, 0 (m, 3H), 3.2-3.4 (m, 6H), 3.8 (m, 1H), 5.0 (m, 1H), 5.6 (t, NH), 6.55 (m, 3H), 6.85 (s, OH),

EXAMPLE 107

3(R)-(9-Hydroxy-9[H]-fluorene-9-carbonyloxy)-1-[3-(4-hydroxyphenoxy)propyl]-1-azoniabicyclo[2.2.2]octane; trifluoroacetate The title compound was synthesised according to methods c and b. The yield of final step was 15 mg, 15%. $^1$H-NMR (DMSO-d6): δ 1.4 (m, 1H), 1.6 (m, 1H), 1.7-1.9 (m, 2H), 1.95-2.05 (m, 2H), 2.1 (m, 1H), 2.8 (m, 1H), 3.1 (d, 1H), 3.25-3.4 (m, 5H), 3.8-3.9 (m, 3H), 5.0 (m, 1H), 6.7 (d, 2H), 6.75 (d, 2H), 6.85 (s, OH), 7.35 (t, 2H), 7.45 (t, 2H), 7.55 (d, 1H), 7.65 (d, 1H), 7.85 (d, 2H), 9.0 (s, OH); MS [M-CF$_3$COO]$^+$: 486.

EXAMPLE 108

1-(2-Benzyloxyethyl)-3(R)-(9-hydroxy-9[H]-fluorene-9-carbonyloxy)-1-azoniabicyclo[2.2.2]octane; bromide The title compound was synthesised according to methods c and a. The yield of final step was 470 mg, 96%. $^1$H-NMR (DMSO-d6): δ 1.4 (m, 1H), 1.65 (m, 1H), 1.7-1.9 (m, 2H), 2.1 (m, 1H), 2.9 (m, 1H), 3.15-3.5 (m, 6H), 3.75 (m, 2H), 3.85 (m, 1H), 4.5 (s, 2H), 5.0 (m, 1H), 6.85 (s, OH), 7.3-7.5 (m, 9H), 7.55 (m, 2H), 7.8 (d, 2H); MS [M-Br]$^+$: 470; mp 86° C.

EXAMPLE 109

3(R)-(9-Hydroxy-9H-fluorene-9-carbonyloxy)-1-(3-thienyl-2-ylpropyl)-1-azoniabicyclo[2.2.2]octane; bromide The title compound was synthesised according to methods c and a. The yield of final step was 180 mg, 70%. $^1$H-NMR (DMSO-d6): δ 1.37 (m, 1H), 1.62 (m, 1H), 1.75-1.95 (m, 4H), 2.06 (m, 1H), 2.72 (m, 1H), 2.80 (m, 2H), 3.02-3.06 (m, 1H), 3.15-3.20 (m, 2H), 3.25-3.40 (m, 3H), 3.80 (m, 1H), 5.0 (m, 1H), 6.85 (s, 1H, OH), 6.95-7.0 (m, 2H), 7.25-7.50 (m, 5H), 7.55-7.65 (m, 2H), 7.85 (d, 2H); MS [M-Br]$^+$: 460; mp 140° C.

EXAMPLE 110

3(R)-(9-Hydroxy-9H-fluorene-9-carbonyloxy)-1-(3-phenylpropyl)-1-azoniabicyclo[2.2.2]octane; trifluoroacetate The title compound was synthesised according to methods c and b. The yield of final step was 80 mg, 40%. $^1$H-NMR (DMSO-d6): δ 1.35 (m, 1H), 1.6 (m, 1H), 1.7-1.90 (m, 2H), 2.05 (m, 1H), 2.5 (m, 2H), 2.7 (m, 1H), 3.0 (m, 1H), 3.15 (m, 2H), 3.2-3.4 (m, 3H), 3.75 (m, 1H), 5.0 (m, 1H), 6.85 (s, OH), 7.20-7.50 (m, 9H), 7.55 (dd, 2H), 7.85 (d, 2H); MS [M-CF3COO]$^+$: 454.

EXAMPLE 111

3(R)-(9-Hydroxy-9H-fluorene-9-carbonyloxy)-1-(4-phenylbutyl)-1-azoniabicyclo[2.2.2]octane; trifluoroacetate The title compound was synthesised according to methods c and b. The yield of final step was 74 mg, 35%. $^1$H-NMR (DMSO-d6): δ 1.35 (m, 1H), 1.45-1.65 (m, 5H), 1.7-1.90 (m, 2H), 2.05 (m, 1H), 2.55-2.75 (m, 3H), 3.0 (m, 1H), 3.15-3.45 (m, 5H), 3.75 (m, 1H), 5.0 (m, 1H), 6.85 (s, OH), 7.20 (m, 3H), 7.25-7.35 (m, 4H), 7.45-7.5 (m, 2H), 7.55-7.6 (dd, 2H), 7.85 (d, 2H); MS [M-CF3COO]$^+$: 468.

EXAMPLE 112

3(R)-(9-Hydroxy-9H-fluorene-9-carbonyloxy-1-(2-thienyl-2-ylethyl)-1-azoniabicyclo[2.2.2]octane; trifluoroacetate The title compound was synthesised according to methods c and b. The yield of final step was 79 mg, 39%. $^1$H-NMR (DMSO-d6): δ 1.4 (m, 1H), 1.65 (m, 1H), 1.8-1.95 (m, 2H), 2.1 (m, 1H), 2.9 (m, 1H), 3.1-3.25 (m, 4H), 3.15-3.45 (m, 5H), 3.85 (m, 1H), 5.05 (m, 1H), 6.85 (s, OH), 7.0 (m, 2H), 7.35 (t, 2H), 7.45-7.5 (m, 3H), 7.55 (d, 1H), 7.65 (d, 1H), 7.85 (d, 2H); MS[M-CF3COO]$^+$: 446.

EXAMPLE 113

3(R)-(9-Hydroxy-9H-fluorene-9-carbonyloxy)-1-(4-phenoxybutyl)-1-azoniabicyclo[2.2.2]octane; trifluoroacetate The title compound was synthesised according to methods c and b. The yield of final step was 72 mg, 33%. $^1$H-NMR (DMSO-d6): δ 1.4 (m, 1H), 1.55-1.9 (m, 7H), 2.05 (m, 1H), 2.7 (m, 1H), 3.0 (in, 1H), 3.15-3.5 (m, 7H), 3.8 (m, 1H), 4.0 (m, 2H), 5.05 (m, 1H), 6.85 (s, OH), 6.95 (m, 3H), 7.25-7.35 (m, 4H), 7.4-7.45 (m, 2H), 7.6 (dd, 2H), 7.85 (d, 2H); MS [M-CF3COO]$^+$: 484.

EXAMPLE 114

3(R)-(9-Methyl-9[H]-fluorene-9-carbonyloxy)-1-(3-phenylallyl)-1-azoniabicyclo[2.2.2]octane; bromide The title compound was synthesised according to methods c and a. The yield of final step was 200 mg, 76%. $^1$H-NMR (DMSO-d6): δ 1.54 (m, 1H), 1.70-1.86 (m, 3H), 1.76 (s, 3H), 2.13 (m, 1H), 3.06 (m, 1H), 3.20-3.50 (m, 4H), 3.86 (m, 1H), 4.05 (dd, 2H), 5.02 (m, 1H), 6.43 (dd, 1H), 6.86 (d, 1H), 7.26-7.46 (m, 7H), 7.58-7.65 (m, 3H), 7.70-7.72 (m, 1H), 7.87-7.90 (m, 2H); MS [M-Br]$^{30}$: 450; mp 234° C.

EXAMPLE 115

3(R)-(9-Methyl-9[H]-fluorene-9-carbonyloxy)-1-(2-phenoxyethyl)-1-azoniabicyclo[2.2.2]octane; bromide The title compound was synthesised according to methods c and a. The yield of final step was 210 mg, 66%. $^1$H-NMR (DMSO-d6): δ 1.55 (m, 1H), 1.60-2.0 (m, 3H), 1.76 (s, 3H), 2.12 (m, 1H), 3.10-3.25 (m, 1H), 3.40-3.80 (m, 6H), 4.0 (m, 1H), 4.41 (m, 2H), 4.98 (m, 1H), 6.98-7.05 (m, 3H), 7.27-7.46 (m, 6H), 7.63-7.71 (m, 2H), 7.87-7.90 (m, 2H); MS [M-Br]$^{30}$: 454; mp 202° C.

EXAMPLE 116

3(R)-(9-Methyl-9[H]-fluorene-9-carbonyloxy)-1-(3-phenoxypropyl)-1-azoniabicyclo[2.2.2] octane; bromide The title compound was synthesised according to methods c and a. The yield of final step was 210 mg, 61%. $^1$H-NMR (DMSO-d6): δ 1.55 (m, 1H), 1.60-2.0 (m, 3H), 1.78 (s, 3H), 2.0-2.20 (m, 3H), 3.0-3.10 (m, 1H), 3.25-3.53 (m, 6H), 3.86 (m, 1H), 4.03 (m, 2H), 4.98 (m, 1H), 6.95-7.0 (m, 3H), 7.30-7.48 (m, 6H), 7.65-7.92 (m, 4H); MS [M-Br]$^{30}$: 468; mp 204° C.

EXAMPLE 117

3(R)-(9-Methyl-9 [H]-fluorene-9-carbonyloxy)-1-phenethyl-1-azoniabicyclo[2.2.2]octane; trifluoroacetate The title compound was synthesised according to methods c and b. The yield of final step was 18 mg, 19%. $^1$H-NMR (DMSO-d6): δ 1.55 (m, 1H), 1.65-1.95 (m, 3H), 1.75 (s, 3H), 2.15 (m, 1H), 2.9-3.1 (m, 4H), 3.25-3.55 (m, 5H), 3.85 (m, 1H), 5.05 (m, 1H), 7.25-7.55 (m, 9H), 7.65 (d, 1H), 7.75 (d, 1H), 7.95 (d, 2H); MS [M-CF$_3$COO]$^+$: 438.

EXAMPLE 118

3(R)-(9-Methyl-9[H]-fluorene-9-carbonyloxy)-1-(4-oxo-4-phenylbutyl)-1-azoniabicyclo[2.2.2]octane; trifluoroacetate The title compound was synthesised according to methods c and b. The yield of final step was 19 mg, 19%. $^1$H-NMR (DMSO-d6): δ 1.55 (m, 1H), 1.65-2.05 (m, 5H), 1.75 (s, 3H), 2.1 (m, 1H) 3.0 (m, 1H), 3.1-3.5 (m, 8H), 3.85 (m, 1H), 7.35-7.5 (m, 4H), 7.55 (t, 2H), 7.65 (t, 2H), 7.7 (d, 1H), 7.9 (d, 2H), 8.0 (d, 2H); MS [M-CF$_3$COO]$^+$: 480.

EXAMPLE 119

1-[3-(4-Fluorophenoxy) propyl]-3(R)-(9-methyl-9 [H]-fluorene-9-carbonyloxy)-1-azoniabicyclo[2.2.2] octane; trifluoroacetate The title compound was synthesised according to methods c and b. The yield of final step was 23 mg, 23%. $^1$H-NMR (DMSO-d6): δ 1.55 (m, 1H), 1.65-1.95 (m, 3H), 1.75 (s, 3H), 2.05-2.15 (m, 3H), 3.0 (m, 1H), 3.25-3.5 (m, 6H), 3.85 (m, 1H), 4.0 (t, 2H), 5.0 (m, 1H), 6.95 (m, 2H), 7.15 (t, 2H), 7.35-7.5 (m, 4H), 7.65 (d, 1H), 7.75 (d, 1H), 7.9 (d, 2H); MS [M-CF$_3$COO]$^+$: 486.

EXAMPLE 120

1-[3-(2,4-Difluorophenoxy) propyl]-3(R)-(9-methyl-9H-fluorene-9-carbonyloxy)-1-azoniabicyclo[2.2.2] octane; trifluoroacetate The title compound was synthesised according to methods c and b. The yield of final step was 20 mg, 19%. $^1$H-NMR (DMSO-d6): δ 1.55 (m, 1H), 1.65-1.95 (m, 3H), 1.75 (s, 3H), 2.05-2.2 (m, 3H), 3.0 (m, 1H), 3.25-3.55 (m, 6H), 3.85 (m, 1H), 4.1 (t, 2H), 5.0 (m, 1H), 7.05 (t, 1H), 7.2-7.5 (m, 6H), 7.65 (d, 1H), 7.75/d, 1H), 7.9 (d, 2H); MS [M-CF$_3$COO]$^+$: 504.

EXAMPLE 121

3(R)-(9-Methyl-9[H]-fluorene-9-carbonyloxy)-1-(3-phenylaminopropyl)-1-azoniabicyclo[2.2.2]octane; trifluoroacetate The title compound was synthesised according to methods c and b. The yield of final step was 19 mg, 19%. $^1$H-NMR (DMSO-d6): δ 1.55 (m, 1H), 1.65-1.95 (m, 5H), 1.75 (s, 3H), 2.1 (m, 1H), 2.95 (m, 1H), 3.05 (m, 2H), 3.15-3.45 (m, 6H), 3.8 (m, 1H), 5.0 (m, 1H), 5.65 (t, NH), 6.6 (m, 3H), 7.1 (t, 2H), 7.35-7.55 (m, 4H), 7.65 (d, 1H), 7.75 (d, 1H), 7.9 (d, 2H); MS [M-CF$_3$COO]$^+$: 467.

EXAMPLE 122

1-[3-(4-Hydroxyphenoxy) propyl]-3(R)-(9-methyl-9 [H]-fluorene-9-carbonyloxy)-1-azoniabicyclo[2.2.2] octane; trifluoroacetate The title compound was synthesised according to methods c and b. The yield of final step was 22 mg, 22%. $^1$H-NMR (DMSO-d6): δ 1.55 (m, 1H), 1.65-1.9 (m, 3H), 1.75 (s, 3H), 2.0-2.15 (m, 3H), 3.0 (m, 1H), 3.25-3.5 (m, 6H), 3.8-3.95 (m, 3H), 5.0 (m, 1H), 6.7 (d, 1H), 6.75 (d, 1H), 7.35-7.45 (m, 4H), 7.65 (d, 1H), 7.75 (d, 1H), 7.9 (d, 2H), 9.0 (s, OH); MS [M-CF$_3$COO]$^+$: 484.

EXAMPLE 123

1-(2-Benzyloxyethyl)-3(R)-(9-methyl-9[H]-fluorene-9-carbonyloxy)-1-azoniabicyclo[2.2.2]octane; trifluoroacetate The title compound was synthesised according to methods c and b. The yield of final step was 17 mg, 17%. $^1$H-NMR (DMSO-d6): δ 1.55 (m, 1H), 1.65-1.95 (m, 4H), 1.75 (s, 3H), 2.15 (m, 1H), 3.1 (m, 1H), 3.3-3.55 (m, 6H), 3.8-3.95 (m, 3H), 4.5 (s, 2H), 5.0 (m, 1H), 7.3-7.5 (m, 9H), 7.6-7.7 (m, 2H), 7.9 (d, 2H); MS [M-CF$_3$COO]$^+$: 468.

EXAMPLE 124

3(R)-(9,10-Dihydroanthracene-9-carbonyloxy)-1-phenethyl-1-azoniabicyclo[2.2.2]octane; bromide The title compound was synthesised according to methods d and a. The yield of final step was 420 mg, 89%. $^1$H-NMR (DMSO-d6): δ 1.55 (m, 1H), 1.65-1.95 (m, 3H), 2.15 (m, 1H), 2.95 (m, 2H), 3.15 (m, 1H), 3.25-3.60 (m, 6H), 3.85 (m, 1H), 3.95-4.15 (dd, 2H, J1=1.8 Hz, J2=4.2 Hz), 5.02 (m, 1H), 5.25 (s, 1H), 7.25-7.43 (m, 11H), 7.48-7.55 (m, 2H); MS [M-Br]$^+$: 438; mp 216° C.

EXAMPLE 125

3(R)-(9,10-Dihydroanthracene-9-carbonyloxy)-1-(3-phenoxypropyl)-1-azoniabicyclo[2.2.2]octane; bromide The title compound was synthesised according to methods d and a. The yield of final step was 450 mg, 82%. $^1$H-NMR (DMSO-d6): δ 1.56 (m, 1H), 1.65-1.95 (m, 3H), 2.05-2.15 (m, 3H), 3.10 (m, 1H), 3.20-3.50 (m, 6H), 3.80 (m, 1H), 3.94-4.14 (m, 4H), 5.0 (m, 1H), 5.22 (s, 1H), 6.94-7.0 (m, 3H), 7.25-7.35 (m, 6H), 7.40 (m, 2H), 7.54-7.47 (m, 2H); MS [M-Br]$^{30}$: 468; mp 157° C.

EXAMPLE 126

1-(4-Phenylbutyl)-3(R)-(9[H]-xanthene-9-carbonyloxy)-azoniabicyclo[2.2.2]octane; bromide The title compound was synthesised according to methods d and a. The yield of final step was 83 mg, 21%. $^1$H-NMR (DMSO-d6): δ 1.50-2.0 (m, 8H), 2.15 (m, 1H), 2.65 (m, 2H), 3.05-3.65 (m, 7H), 3.80 (m, 1H), 5.0 (m, 1H), 5.30 (s, 1H), 7.10-7.45 (m, 11H), 7.45-7.60 (m, 2H); MS [M-Br]$^{30}$: 468; mp 95° C.

EXAMPLE 127

1-(2-Phenoxyethyl)-3(R)-(9[H]-xanthene-9-carbonyloxy)-1-azoniabicyclo[2.2.2]octane; bromide The title compound was synthesised according to methods d and a. The yield of final step was 300 mg, 73%. $^1$H-NMR (DMSO-d6): δ 1.70-2.0 (m, 4H), 2.2 (m, 1H), 3.20-3.80 (m, 7H), 4.0 (m, 1H), 4.40 (m, 2H), 5.05 (m, 1H), 5.30 (s, 1H), 7.0-7.10 (m, 7H), 7.30-7.45 (m, 4H), 7.45-7.55 (m, 2H); MS [M-Br]$^{30}$: 456; mp 200° C.

EXAMPLE 128

1-(3-Phenoxypropyl)-3(R)-(9[H]-xanthene-9-carbonyloxy)-1-azoniabicyclo[2.2.2]octane; bromide The title compound was synthesised according to methods d and a. The yield of final step was 350 mg, 83%. $^1$H-NMR (DMSO-d6): δ 1.70-2.0 (m, 4H), 2.0-2.25 (m, 3H), 3.15-3.65 (m, 7H), 3.85-3.95 (m, 1H), 3.95-4.10 (m, 2H), 5.0 (m, 1H), 5.30 (s, 1H), 6.90-7.0 (m, 3H), 7.10-7.25 (m, 4H), 7.25-7.40 (m, 4H), 7.40-7.60 (m, 2H); MS [M-Br]$^{30}$: 470; mp 184° C.

EXAMPLE 129

1-Phenethyl-3(R)-(9[H]-xanthene-9-carbonyloxy)-1-azoniabicyclo[2.2.2]octane; bromide The title compound was synthesised according to methods d and a. The yield of final step was 100 mg, 44%. $^1$H-NMR (DMSO-d6): δ 1.65-2.0 (m, 4H), 2.1 (m, 1H), 2.9-3.05 (m, 2H), 3.15-3.6 (m, 7H), 3.85 (m, 1H), 5.05 (m, 1H), 5.3 (s, 1H)), 7.15-7.55 (m, 13H); MS [M-Br]$^+$: 440.

EXAMPLE 130

1-(4-Oxo-4-phenylbutyl)-3(R)-(9[H]-xanthene-9-carbonyloxy)-1-azoniabicyclo[2.2.2]octane; trifluoroacetate The title compound was synthesised according to methods d and b. The yield of final step was 16 mg, 15%. $^1$H-NMR (DMSO-d6): δ 1.65-2.05 (m, 6H), 2.1 (m, 1H), 3.1-3.55 (m, 9H), 3.8 (m, 1H), 5.05 (m, 1H), 5.25 (s, 1H), 7.1-7.3 (m, 4H), 7.35 (t, 2H), 7.45-7.6 (m, 4H), 7.7 (d, 1H), 8.0 (d, 1H); MS [M-CF$_3$COO]$^+$: 482.

EXAMPLE 131

1-[3-(4-Fluorophenoxy)propyl]-3(R)-(9[H]-xanthene-9-carbonyloxy)-1-azoniabicyclo[2.2.2]octane, trifluoroacetate The title compound was synthesised according to methods d and b. The yield of final step was 18 mg, 18%. $^1$H-NMR (DMSO-d6): δ 1.7-2.1 (m, 6H), 2.15 (m, 1H), 3.1-3.5 (m, 7H), 3.8 (m, 1H), 4.0 (t, 2H), 5.0 (m, 1H), 5.3 (s, 1H), 6.95 (m, 2H), 7.1-7.3 (m, 6H), 7.4 (t, 2H), 7.5 (dd, 2H); MS [M-CF$_3$COO]$^+$: 488.

EXAMPLE 132

1-[3-(2,4-Difluorophenoxy)propyl]-3(R)-(9[H]-xanthene-9-carbonyloxy)-1-azoniabicyclo[2.2.2]octane; trifluoroacetate The title compound was synthesised according to methods d and b. The yield of final step was 14 mg, 14%. $^1$H-NMR (DMSO-d6): δ 1.65-1.95 (m, 4H), 2.05-2.2 (m, 3H), 3.1-3.55 (M, 7H), 3.8 (m, 1H), 4.05 (t, 2H), 5.0 (m, 1H), 5.3 (s, 1H), 7.05 (t, 1H), 7.1-7.55 (m, 10H); MS [M-CF$_3$COO]$^+$: 506.

EXAMPLE 133

1-(3-Phenylaminopropyl)-3(R)-(9[H]-xanthene-9-carbonyloxy)-1-azoniabicyclo[2.2.2]octane; trifluoroacetate The title compound was synthesised according to methods d and b. The yield of final step was 17 mg, 17%. $^1$H-NMR (DMSO-d6): δ 1.65-2.0 (m, 6H), 2.15 (m, 1H), 3.0-3.5 (m, 9H), 1.75 (m, 1H), 5.0 (m, 1H), 5.3 (s, 1H), 6.65 (t, NH), 6.55 (m, 3H), 7.05-7.3 (m, 6H), 7.35-7.55 (m, 4H); MS [M-CF$_3$COO]$^+$: 469.

EXAMPLE 134

1-[3-(4-Hydroxyphenoxy)propyl]-3(R)-(9[H]-xanthene-9-carbonyloxy)-1-azoniabicyclo[2.2.2]octane; trifluoroacetate The title compound was synthesised according to methods d and b. The yield of final step was 21 mg, 20%. $^1$H-NMR (DMSO-d6): δ 1.7-2.1 (m, 6H), 2.15 (m, 1H), 3.1-3.5 (m, 7H), 3.7-3.95 (m, 3H), 5.0 (m, 1H), 5.3 (s, 1H), 6.7 (d, 2H), 6.75 (d, 2H), 7.1-7.3 (m, 4H), 7.35-7.55 (m, 4H), 9.0 (s, OH); MS [M-CF$_3$COO]$^+$: 486.

EXAMPLE 135

1-(2-Benzyloxyethyl)-3(R)-(9 [H]-xanthene-9-carbonyloxy)-1-azoniabicyclo[2.2.2]octane; trifluoroacetate The title compound was synthesised according to methods d and b. The yield of final step was 16 mg, 16%. $^1$H-NMR (DMSO-d6): δ 1.65-1.95 (m, 4H), 2.1 (m, 1H), 3.1-3.9 (m, 10H), 4.5 (s, 2H), 5.0 (m, 1H), 5.3 (s, 1H), 7.15 (m, 4H), 7.3-7.5 (m, 7H), 7.55 (t, 2H); MS [M-CF$_3$COO]$^+$: 470.

EXAMPLE 136

3(R)-(9-Hydroxy-9[H]-xanthene-9-carbonyloxy)-1-(3-phenoxypropyl)-1-azoniabicyclo[2.2.2]octane; bromide The title compound was synthesised according to methods c and a. The yield of final step was 340 mg, 71%. $^1$H-NMR (DMSO-d6): δ 1.30 (m, 1H), 1.65 (m, 1H), 1.70-1.95 (m, 2H), 1.95-2.10 (m, 3H), 2.70 (m, 1H), 2.90 (m, 1H), 3.2-3.5 (m, 5H), 3.80 (m, 1H), 4.0 (t, 2H), 5.05 (m, 1H), 6.90-7.0 (m, 3H), 7.20-7.35 (m, 7H), 7.40-7.46 (m, 2H), 7.65-7.70 (m, 2H); MS [M-Br]³⁰ : 486; mp 219° C.

EXAMPLE 137

3(R)-(9-Hydroxy-9[H]-xanthene-9-carbonyloxy)-1-phenethyl-1-azoniabicyclo[2.2.2]octane; bromide The title compound was synthesised according to methods c and a. The yield of final step was 290 mg, 64%. ¹H-NMR (DMSO-d6): δ 1.32 (m, 1H), 1.65 (m, 1H), 1.70-1.95 (m, 2H), 2.1 (m, 1H), 2.75-2.90 (m, 3H), 3.05 (m, 1H), 3.30-3.50 (m, 5H), 3.82 (m, 1H), 5.05 (m, 1H), 7.20-7.40 (m, 10H), 7.40-7.50 (m, 2H), 7.65-7.70 (m, 2H); MS [M-Br]³⁰ : 456; mp 221° C.

EXAMPLE 138

3(R)-(9-Hydroxy-9H-xanthene-9-carbonyloxy)-1-(3-thien-2-ylpropyl)-1-azoniabicyclo[2.2.2]octane; bromide The title compound was synthesised according to methods c and a. The yield of final step was 310 mg, 97%. ¹H-NMR (DMSO-d6): δ 1.30 (m, 1H), 1.62 (m, 1H), 1.70-1.90 (m, 4H), 2.05 (m, 1H), 2.60 (m, 1H), 2.75-2.85 (m, 4H), 3.15 (m, 2H), 3.25-3.40 (m, 2H), 3.75 (m, 1H), 5.0 (m, 1H), 6.93 (m, 1H), 7.0 (m, 1H), 7.14-7.26 (m, 5H), 7.36-7.45 (m, 3H), 7.63-7.67 (m, 2H); MS [M-Br]⁺: 476; mp 111° C.

EXAMPLE 139

3(R)-(9-Hydroxy-9H-xanthene-9-carbonyloxy)-1-(3-phenylpropyl)-1-azoniabicyclo[2.2.2]octane; trifluoroacetate The title compound was synthesised according to methods c and b. The yield of final step was 85 mg, 41%. ¹H-NMR (DMSO-d6): δ 1.30 (m, 1H), 1.65 (m, 1H), 1.70-1.95 (m, 2H), 2.05 (m, 1H), 2.5-2.6 (m, 2H), 2.80 (m, 1H), 3.05-3.75 (m, 7H), 5.05 (m, 1H), 7.1-7.45 (m, 12H), 7.65-7.70 (m, 2H); MS [M-CF3COO]⁺: 470.

EXAMPLE 140

3(R)-(9-Hydroxy-9H-xanthene-9-carbonyloxy)-1-(4-phenylbutyl)-1-azoniabicyclo[2.2.2]octane; trifluoroacetate The title compound was synthesised according to methods c and b. The yield of final step was 84 mg, 38%. ¹H-NMR (DMSO-d6): δ 1.30 (m, 1H), 1.4-1.85 (m, 7H), 2.05 (m, 1H), 2.5-2.6 (m, 2H), 2.80 (m, 1H), 3.05-3.4 (m, 6H), 3.7 (m, 1H), 5.05 (m, 1H), 7.15-7.35 (m, 10H), 7.4 (m, 1H), 7.65 (m, 2H); MS [M-CF3COO]⁺: 484.

EXAMPLE 141

3(R)-(9-Hydroxy-9H-xanthene-9-carbonyloxy)-1-(2-thien-2-ylethyl)-1-azoniabicyclo[2.2.2]octane; trifluoroacetate The title compound was synthesised according to methods c and b. The yield of final step was 81 mg, 39%. ¹H-NMR (DMSO-d6): δ 1.30 (m, 1H), 1.6 (m, 1H), 1.7-1.9 (m, 2H), 2.05 (m, 1H), 2.75 (m, 1H), 3.0 (m, 1H), 3.1-3.2 (m, 2H), 3.3-3.6 (m, 5H), 3.8 (m, 1H), 5.05 (m, 1H), 6.95-7.0 (m, 2H), 7.15-7.3 (m, 5H), 7.45 (m, 3H), 7.65 (m, 2H); MS [M-CF3COO]⁺: 462.

EXAMPLE 142

3(R)-(9-Hydroxy-9H-xanthene-9-carbonyloxy)-1-(4-phenoxybutyl)-1-azoniabicyclo[2.2.2]octane; trifluoroacetate The title compound was synthesised according to methods c and b. The yield of final step was 83 mg, 37%. ¹H-NMR (DMSO-d6): δ 1.3 (m, 1H), 1.5-1.9 (m, 7H), 2.05 (m, 1H), 2.6 (m, 1H), 2.8 (m, 1H), 3.1-3.45 (m, 7H), 3.75 (m, 1H), 4.0 (m, 2H), 5.05 (m, 1H), 6.95-7.0 (m, 3H), 7.15-7.45 (m, 9H), 7.65 (m, 2H); MS [M-CF3COO]⁺: 500.

EXAMPLE 143

3(R)-(9-Hydroxy-9H-xanthene-9-carbonyloxy)-1-(2-phenoxyethyl)-1-azoniabicyclo[2.2.2]octane; trifluoroacetate The title compound was synthesised according to methods c and b. The yield of final step was 102 mg, 48%. ¹H-NMR (DMSO-d6): δ 1.3 (m, 1H), 1.55-1.95 (m, 3H), 2.05 (m, 1H), 2.8 (m, 1H), 3.1 (m, 1H), 3.35-3.65 (m, 5H), 3.9 (m, 1H), 4.35 (m, 2H), 5.05 (m, 1H), 6.95 (d, 2H), 7.0-7.1 (m, 2H), 7.2 (m, 4H), 7.3-7.45 (m, 4H), 7.6 (t, 2H); MS [M-CF3COO]⁺: 472.

EXAMPLE 144

1-[3-(4-Fluorophenoxy)propyl]-3(R)-(9-hydroxy-9H-xanthene-9-carbonyl oxy)-1-azoniabicyclo[2.2.2]octane; trifluoroacetate The title compound was synthesised according to methods c and b. The yield of final step was 99 mg, 44%. ¹H-NMR (DMSO-d6): δ 1.3 (m, 1H), 1.6 (m, 1H), 1.7-2.0 (m, 4H), 2.05 (m, 1H), 2.7 (m, 1H), 2.9 (m, 1H), 3.2-3.5 (m, 5H), 3.75-3.85 (m, 1H), 3.95 (m, 2H), 5.0 (m, 1H), 6.95 (m, 2H), 7.1-7.3 (m, 7H), 7.45 (t, 2H), 7.65 (t, 2H); MS [M-CF3COO]⁺: 504.

EXAMPLE 145

3(R)-(9-Hydroxy-9H-xanthene-9-carbonyloxy)-1-(3-phenylallyl)-1-azoniabicyclo[2.2.2]octane; trifluoroacetate The title compound was synthesised according to methods c and b. The yield of final step was 25 mg, 12%. ¹H-NMR (DMSO-d6): δ 1.25-1.30 (m, 1H), 1.55-1.95 (m, 3H), 2.10 (m, 1H), 2.65-2.75 (m, 1H), 2.9 (m, 1H), 3.25-3.50 (m, 2H), 3.75-3.8 (m, 1H), 3.95 (m, 2H), 4.2 (d, 1H), 5.0 (m, 1H), 6.35 (m, 1H), 6.80 (d, 1H), 7.05-7.50 (m, 8H), 7.60 (m, 4H); MS [M-CF3COO]⁺: 468.

EXAMPLE 146

3(R)-(9-Methyl-9[H]-xanthene-9-carbonyloxy)-1-(3-phenoxypropyl)-1-azoniabicyclo[2.2.2]octane; bromide The title compound was synthesised according to methods c and a. The yield of final step was 110 mg. ¹H-NMR (DMSO-d6): δ 1.4 (m, 1H), 1.65 (m, 1H), 1.75-1.95 (m, 2H), 1.9 (s, 3H), 2.05-2.15 (m, 3H), 1.8 (m, 1H), 3.15 (m, 2H), 3.25-3.5 (m, 5H), 3.85 (m, 1H), 4.0 (t, 2H), 5.05 (m, 1H), 6.95-7.0 (m, 3H), 7.15-7.2 (m, 4H), 7.3-7.4 (m, 4H), 7.45 (d, 1H), 7.55 (d, 1H); MS [M-Br]$^{30}$ : 484; mp 195° C.

EXAMPLE 147

3(R)-(9-Methyl-9[H]-xanthene-9-carbonyloxy)-1-phenethyl-1-azoniabicyclo[2.2.2]octane; trifluoroacetate The title compound was synthesised according to methods c and b. The yield of final step was 19 mg, 20%. $^1$H-NMR (DMSO-d6): δ 1.4 (m, 1H), 1.65 (m, 1H), 1.8-1.95 (m, 2H), 1.9 (s, 3H), 2.15 (m, 1H), 2.8-2.95 (m, 3H), 3.15 (d, 1H), 3.3-3.5 (m, 5H), 4.9 (m, 1H), 5.1 (m, 1H), 7.15 (m, 4H), 7.25-7.4 (m, 7H), 7.45 (d, 1H), 7.55 (d, 1H); MS [M-CF$_3$COO]$^+$: 454.

EXAMPLE 148

3(R)-(9-Methyl-9[H]-xanthene-9-carbonyloxy)-1-(2-phenoxyethyl)-1-azoniabicyclo[2.2.2]octane; trifluoroacetate The title compound was synthesised according to methods c and b. The yield of final step was 24 mg, 24%. $^1$H-NMR (DMSO-d6): δ 1.4 (m, 1H), 1.65 (m, 1H), 1.8-1.95 (m, 2H), 1.9 (s, 3H), 2.15 (m, 1H), 2.95 (m, 1H), 3.25 (m, 1H), 3.4-3.65 (m, 5H), 3.85 (m, 1H), 4.35 (t, 2H), 5.05 (m, 1H), 6.95 (d, 2H), 7.05 (t, 2H), 7.15 (m, 3H), 7.25-7.45 (m, 6H); MS [M-CF$_3$COO]$^+$: 470.

EXAMPLE 149

3(R)-(9-Methyl-9[H]-xanthene-9-carbonyloxy)-1-(4-oxo-4-phenylbutyl)-1-azoniabicyclo[2.2.2]octane; trifluoroacetate The title compound was synthesised according to methods c and b. The yield of final step was 19 mg, 19%. $^1$H-NMR (DMSO-d6): δ 1.4 (m, 1H), 1.65 (m, 1H), 1.75-1.95 (m, 7H), 2.15 (m, 1H), 2.8 (m, 1H), 3.05-3.25 (m, 4H), 3.3-3.5 (m, 4H), 3.85 (m, 1H), 5.05 (m, 1H), 7.15 (m, 4H), 7.35 (t, 2H), 7.45-7.6 (m, 4H), 7.7 (t, 1H), 8.0 (d, 2H); MS [M-CF$_3$COO]$^+$: 496.

EXAMPLE 150

1-[3-(4-Fluorophenoxy) propyl]-3(R)-(9-methyl-9[H]-xanthene-9-carbonyloxy)-1-azoniabicyclo[2.2.2]octane; trifluoroacetate The title compound was synthesised according to methods c and b. The yield of final step was 25 mg, 24%. $^1$H-NMR (DMSO-d6): δ 1.4 (m, 1H), 1.65 (m, 1H), 1.75-1.95 (m, 2H), 1.9 (s, 3H), 1.95-2.1 (m, 2H), 2.15 (m, 1H), 2.8 (m, 1H), 3.1 (d, 1H), 3.25-3.5 (m, 5H), 3.8 (m, 1H), 4.0 (t, 2H), 5.05 (m, 1H), 6.95 (m, 2H), 7.15 (m, 6H), 7.35 (t, 2H), 7.5 (dd, 2H); MS [M-CF$_3$COO]$^+$: 502.

EXAMPLE 151

1-[3-(2,4-Difluorophenoxy)propyl]-3(R)-(9-methyl-9[H]-xanthene-9-carbonyloxy)-1-azoniabicyclo[2.2.2]octane; trifluoroacetate The title compound was synthesised according to methods c and b. The yield of final step was 16 mg, 15%. $^1$H-NMR (DMSO-d6): δ 1.4 (m, 1H), 1.65 (m, 1H), 1.75-1.95 (m, 2H), 1.9 (s, 3H), 2.0-2.15 (m, 3H), 2.8 (m, 1H), 3.1 (d, 1H), 7.05 (t, 1H), 7.1-7.4 (m, 8H), 7.5 (dd, 2H); MS [M-CF$_3$COO]$^+$: 520.

EXAMPLE 152

3(R)-(9-Methyl-9[H]-xanthene-9-carbonyloxy)-1-(3-phenylaminopropyl)-1-azoniabicyclo[2.2.2]octane; trifluoroacetate The title compound was synthesised according to methods c and b. The yield of final step was 16 mg, 15%. $^1$H-NMR (DMSO-d6): δ 1.35 (m, 1H), 1.6 (m, 1H), 1.7-1.9 (m, 4H), 1.9 (s, 3H), 2.1 (m, 1H), 2.7 (m, 1H), 2.95-3.05 (m, 3H), 3.1-3.4 (m, 6H), 3.75 (m, 1H), 5.0 (m, 1H), 5.6 (m, 1H), 6.55 (m, 3H), 7.05-7.15 (m, 6H), 7.3 (m, 2H), 7.45 (t, 2H); MS [M-CF$_3$COO]$^+$: 483.

EXAMPLE 153

1-[3-(4-Hydroxyphenoxy) propyl]-3(R)-(9-methyl-9[H]-xanthene-9-carbonyloxy)-1-azoniabicyclo[2.2.2]octane; trifluoroacetate The title compound was synthesised according to methods c and b. The yield of final step was 19 mg, 18%. $^1$H-NMR (DMSO-d6): δ 1.4 (m, 1H), 1.65 (m, 1H), 2.75-2.05 (m, 4H), 1.9 (s, 3H), 2.15 (m, 1H), 2.8 (m, 1H), 3.1 (d, 1H), 3.25-3.5 (m, 5H), 3.8-3.95 (m, 3H), 5.05 (m, 1H), 6.65-6.8 (m, 4H), 7.2 (m, 4H), 7.35 (t, 2H), 7.5 (m, 2H), 9.0 (s, OH); MS [M-CF$_3$COO]$^+$: 500.

EXAMPLE 154

1-(2-Benzyloxyethyl)-3(R)-(9-methyl-9[H]-xanthene-9-carbonyloxy)-1-azoniabicyclo[2.2.2]octane; trifluoroacetate The title compound was synthesised according to methods c and b. The yield of final step was 14 mg, 14%. $^1$H-NMR (DMSO-d6): δ 1.4 (m, 1H), 1.65 (m, 1H), 1.75-1.95 (m, 2H), 1.9 (s, 3H), 2.1 (m, 1H), 2.9 (m, 1H), 3.2-3.5 (m, 6H), 3.75-3.95 (m, 3H), 4.5 (s, 2H), 5.05 (m, 1H), 7.15 (m, 4H), 7.3-7.5 (m, 9H); MS [M-CF$_3$COO]$^+$: 484.

EXAMPLE 155

1-(3-Phenoxypropyl)-3(R)-(9[H]-thioxanthene-9-carbonyloxy)-1-azoniabicyclo[2.2.2]octane; bromide The title compound was synthesised according to methods d and a. The yield of final step was 323 mg, 50%. $^1$H-NMR (DMSO-d6): δ 1.35 (m, 1H), 1.65 (m, 1H), 1.70-1.95 (m, 2H), 2.0-2.2 (m, 3H), 2.75-2.90 (m, 1H), 3.12 (m, 1H), 3.25-3.50 (m, 5H), 3.80 (m, 1H), 4.0 (t, 2H), 5.0 (m, 1H), 5.6 (s, 1H), 6.94-7.0 (m, 3H), 7.22-7.41 (m, 6H), 7.45-7.64 (m, 4H); MS [M-Br]$^+$: 486; mp 157° C.

EXAMPLE 156

1-(3-phenylallyl)-3(R)-(10,11-Dihydro-5H-dibenzo[a,d]cycloheptene-5-carbonyloxy)-1-azoniabicyclo[2.2.2]octane; bromide The title compound was synthesised according to methods d and a. The yield of final step was 250 mg, 94%. $^1$H-NMR (CDCl$_3$): δ 1.50-1.60 (m, 1H), 1.60-1.80 (m, 1H), 1.90 (m, 2H), 2.30 (m, 1H), 2.65-2.80 (m, 2H), 2.90-3.20 (m, 3H), 3.50 (d, 1H), 3.60-3.90 (m, 3H), 4.20 (m, 1H), 4.35-4.60 (doble dd, 2H), 5.10 (m, 1H), 5.15 (s, 1H), 6.05 (dd, 1H), 6.90-7.0 (m, 2H), 7.0-7.5 (m, 11H); MS [M-Br]$^{30}$ : 464; mp 132° C.

EXAMPLE 157

1-(3-phenoxypropyl)-3(R)-(10,11-Dihydro-5H-dibenzo[a,d]cycloheptene-5-carbonyloxy)-1-azoniabicyclo[2.2.2]octane; bromide The title compound was synthesised according to methods d and a. The yield of final step was 290 mg, 94%. $^1$H-NMR (CDCl$_3$): δ 1.45-1.60 (m, 1H), 1.65-1.80 (m, 1H), 1.80-2.0 (m, 2H), 2.0-2.20 (m, 3H), 2.80-3.0 (m, 3H), 3.15-3.30 (m, 2H), 3.30-3.45 (d, 1H), 3.45-3.80 (m, 5H), 3.85-4.0 (m, 2H), 4.20 (m, 1H), 5.10 (m, 1H), 5.20 (s, 1H), 6.80-6.90 (d, 2H), 6.90-7.0 (t, 1H), 7.10-7.30 (m, 8H), 7.40 (m, 2H); MS [M-Br]$^{30}$ : 482; mp 182° C.

EXAMPLE 158

3(R)-(5[H]-Dibenzo[a,d]cycloheptene-5-carbonyloxy)-1-(3-phenoxypropyl)-1-azoniabicyclo[2.2.2]octane; bromide The title compound was synthesised according to methods d and a. The yield of final step was 180 mg, 56%. $^1$H-NMR (DMSO-d6): δ 1.2 (m, 1H), 1.6 (m, 1H), 1.7-1.9 (m, 2H), 1.95 (m, 1H), 2.1 (m, 2H), 2.8 (m, 1H), 2.95 (d, 1H), 3.25-3.45 (m, 5H), 3.8 (m, 1H), 4.05 (t, 2H), 4.9 (m, 1H), 5.45 (s, 1H), 6.9-7.1 (m, 5H), 7.3-7.5 (m, 9H), 7.55 (d, 2H); MS [M-Br]$^{30}$ : 480; mp 111° C.

EXAMPLE 159

3(R)-(5[H]-Dibenzo[a,d]cycloheptene-5-carbonyloxy)-1-phenethyl-1-azoniabicyclo[2.2.2]octane; bromide The title compound was synthesised according to methods d and a. The yield of final step was 210 mg, 68%. $^1$H-NMR (DMSO-d6): δ 1.2 (m, 1H), 1.7-1.9 (m, 2H), 2.0 (m, 1H), 2.85-3.1 (m, 4H), 3.3-3.5 (m, 5H), 3.85 (m, 1H), 4.95 (m, 1H), 5.45 (s, 1H), 7.05 (m, 2H), 7.25-7.5 (m, 11H), 7.55 (m, 2H); MS [M-Br]$^+$: 450; mp 248° C.

The Examples 160 to 164 illustrate pharmaceutical compositions according to the present invention and procedure for their preparation.

EXAMPLE 160

Preparation of a Pharmaceutical Composition: Tablets

Formulation:

| | |
|---|---|
| Compound of the present invention | 5.0 mg |
| Lactose | 113.6 mg |
| Microcrystalline cellulose | 28.4 mg |
| Light silicic anhydride | 1.5 mg |
| Magnesium stearate | 1.5 mg |

Using a mixer machine, 15 g of the compound of the present invention was mixed with 340.8 g of lactose and 85.2 g of microcrystalline cellulose. The mixture was subjected to compression moulding using a roller compactor to give a flake-like compressed material. The flake-like compressed material was pulverized using a hammer mill, and the pulverized material was screened through a 20 mesh screen. A 4.5 g portion of light silicic anhydride and 4.5 g of magnesium stearate were added to the screened material and mixed. The mixer product was subjected to a tablets making machine equipped with a die/punch system of 7.5 mm in diameter, thereby obtaining 3,000 tablets each having 150 mg in weight.

EXAMPLE 161

Preparation of a Pharmaceutical Composition: Tablets Coated

Formulation:

| | |
|---|---|
| Compound of the present invention | 5.0 mg |
| Lactose | 95.2 mg |
| Corn starch | 40.8 mg |
| Polyvinylpyrrolidone K25 | 7.5 mg |
| Magnesium stearate | 1.5 mg |
| Hydroxypropylcellulose | 2.3 mg |
| Polyethylene glycol 6000 | 0.4 mg |
| Titanium dioxide | 1.1 mg |
| Purified talc | 0.7 mg |

Using a fluidized bed granulating machine, 15 g of the compound of the present invention was mixed with 285.6 g of lactose and 122.4 g of corn starch. Separately, 22.5 g of polyvinylpyrrolidone was dissolved in 127.5 g of water to prepare a binding solution. Using a fluidized bed granulating machine, the binding solution was sprayed on the above mixture to give granulates. A 4.5 g portion of magnesium stearate was added to the obtained granulates and mixed. The obtained mixture was subjected to a tablet making machine equipped with a die/punch biconcave system of 6.5 mm in diameter, thereby obtaining 3,000 tablets, each having 150 mg in weight.

Separately, a coating solution was prepared by suspending 6.9 g of hydroxypropylmethylcellulose 2910, 1.2 g of polyethylene glycol 6000, 3.3 g of titanium dioxide and 2.1 g of purified talc in 72.6 g of water. Using a High Coated, the 3,000 tablets prepared above were coated with the coating solution to give film-coated tablets, each having 154.5 mg in weight.

EXAMPLE 162

Preparation of a Pharmaceutical Composition: Liquid Inhalant

Formulation:

| | |
|---|---|
| Compound of the present invention | 400 µg |
| Physiological saline | 1 ml |

A 40 mg portion of the compound of the present invention was dissolved in 90 ml of physiological saline, and the solution was adjusted to a total volume of 100 ml with the same saline solution, dispensed in 1 ml portions into 1 ml capacity ampoule and then sterilized at 115° for 30 minutes to give liquid inhalant.

EXAMPLE 163

Preparation of a Pharmaceutical Composition: Powder Inhalant

Formulation:

| | |
|---|---|
| Compound of the present invention | 200 μg |
| Lactose | 4,000 μg |

A 20 g portion of the compound of the present invention was uniformly mixed with 400 g of lactose, and a 200 mg portion of the mixture was packed in a powder inhaler for exclusive use to produce a powder inhalant.

EXAMPLE 164

Preparation of a Pharmaceutical Composition: Inhalation Aerosol

Formulation:

| | |
|---|---|
| Compound of the present invention | 200 μg |
| Dehydrated (Absolute) ethyl alcohol USP | 8,400 μg |
| 1,1,1,2-Tetrafluoroethane (HFC-134A) | 46,810 μg |

The active ingredient concentrate is prepared by dissolving 0.0480 g of the compound of the present invention in 2.0160 g of ethyl alcohol. The concentrate is added to an appropriate filling apparatus. The active ingredient concentrate is dispensed into aerosol container, the headspace of the container is purged with Nitrogen or HFC-134A vapor (purging ingredients should not contain more than 1 ppm oxygen) and is sealed with valve. 11.2344 g of HFC-134A propellant is then pressure filled into the sealed container.

The invention claimed is:

1. A method for treating chronic obstructive pulmonary disease or chronic bronchitis, or inhibiting bronchospasm, which method comprises use of a powder inhaler to administer to a human patient in need of such treatment an effective amount of a powder inhalant, wherein the powder inhalant comprises 3(R)-(2-hydroxy-2,2-dithien-2-ylacetoxy)-1-(3-phenoxypropyl)-1-azoniabicyclo[2.2.2]octane bromide.

2. The method of claim 1, wherein the powder inhalant further comprises a pharmaceutically acceptable carrier or diluent.

3. The powder inhaler of claim 2, wherein the pharmaceutically acceptable carrier or diluent of the powder inhalant is lactose.

4. The method of claim 1, wherein the powder inhalant further comprises a $\beta_2$ agonist.

5. The method of claim 4, wherein the powder inhalant further comprises a steroid or a phosphodiesterase IV inhibitor.

6. The method of claim 1, wherein the powder inhalant further comprises a steroid.

7. The method of claim 6, wherein the powder inhalant further comprises a phosphodiesterase IV inhibitor.

8. The method of claim 1, wherein the powder inhalant further comprises a phosphodiesterase IV inhibitor.

9. The method of claim 1 further comprising administering an effective amount of a $\beta_2$ agonist.

10. The method of claim 9 further comprising administering an effective amount of a steroid or a phosphodiesterase IV inhibitor.

11. The method of claim 1 further comprising administering an effective amount of a steroid.

12. The method of claim 11 further comprising administering an effective amount of a phosphodiesterase IV inhibitor.

13. The method of claim 1 further comprising administering an effective amount of a phosphodiesterase IV inhibitor.

* * * * *